US012723084B2

(12) United States Patent
Claus et al.

(10) Patent No.: US 12,723,084 B2

(45) Date of Patent: Sep. 1, 2026

(54) 4-1BBL TRIMER-CONTAINING ANTIGEN BINDING MOLECULES

(71) Applicant: Hoffmann-La Roche Inc., Little Falls, NJ (US)

(72) Inventors: Christina Claus, Ennetebaden (CH); Claudia Ferrara Koller, Zug (CH); Christian Klein, Bonstetten (CH); Pablo Umana, Wollerau (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 921 days.

(21) Appl. No.: 17/811,376

(22) Filed: Jul. 8, 2022

(65) Prior Publication Data

US 2023/0086210 A1 Mar. 23, 2023

Related U.S. Application Data

(63) Continuation of application No. PCT/EP2021/050145, filed on Jan. 7, 2021.

(30) Foreign Application Priority Data

Jan. 9, 2020 (EP) .................................... 20151043

(51) Int. Cl.

*C07K 16/28* (2006.01)
*A61P 35/00* (2006.01)
*A61K 39/00* (2006.01)

(52) U.S. Cl.

CPC .......... *C07K 16/2827* (2013.01); *A61P 35/00* (2018.01); *A61K 2039/505* (2013.01); *C07K 2317/52* (2013.01); *C07K 2317/55* (2013.01); *C07K 2317/565* (2013.01); *C07K 2317/624* (2013.01)

(58) Field of Classification Search

None

See application file for complete search history.

(56) References Cited

U.S. PATENT DOCUMENTS

| | | | |
|---|---|---|---|
| 5,571,894 | A | 11/1996 | Wels et al. |
| 5,587,458 | A | 12/1996 | King et al. |
| 5,869,046 | A | 2/1999 | Presta et al. |
| 7,288,638 | B2 | 10/2007 | Jure-Kunkel et al. |
| 7,659,384 | B2 | 2/2010 | Jure-Kunkel et al. |

(Continued)

FOREIGN PATENT DOCUMENTS

| | | | |
|---|---|---|---|
| EP | 3243832 | A1 | 11/2017 |
| EP | 3470426 | A1 | 4/2019 |

(Continued)

OTHER PUBLICATIONS

Bartkowiak, T., et al., "4-1BB Agonists: Multi-Potent Potentiators of Tumor Immunity" Front Oncol 5(117):1-16 (Jun. 8, 2015).

(Continued)

*Primary Examiner* — Maria Marvich

(74) *Attorney, Agent, or Firm* — Lawrence S. Graham; Genentech, Inc.

(57) ABSTRACT

The invention relates to 4-1BBL trimer-containing antigen binding molecules comprising at least one antigen binding domain capable of specific binding to PD-L1 and their use in the treatment of cancer.

17 Claims, 6 Drawing Sheets

Specification includes a Sequence Listing.

(56) References Cited

U.S. PATENT DOCUMENTS

| | | | | |
|---|---|---|---|---|
| 10,392,445 | B2 | 8/2019 | Amann et al. | |
| 10,464,981 | B2 | 11/2019 | Amann et al. | |
| 10,526,413 | B2 | 1/2020 | Amann et al. | |
| 11,149,083 | B2 | 10/2021 | Amann et al. | |
| 11,267,903 | B2 | 3/2022 | Amann et al. | |
| 11,306,154 | B2 | 4/2022 | Amann et al. | |
| 2016/0200833 | A1* | 7/2016 | Amann | C07K 16/40 |
| 2017/0247467 | A1 | 8/2017 | Amann et al. | |
| 2018/0002436 | A1 | 1/2018 | Lo et al. | |
| 2018/0326010 | A1* | 11/2018 | Codarri Deak | A61P 35/00 |
| 2019/0016771 | A1 | 1/2019 | Amann et al. | |
| 2019/0107537 | A1* | 4/2019 | Chaudhary | G01N 33/536 |
| 2019/0185566 | A1 | 6/2019 | Koller et al. | |
| 2019/0194291 | A1 | 6/2019 | Bruenker et al. | |
| 2019/0211113 | A1 | 7/2019 | Amann et al. | |
| 2020/0071411 | A1 | 3/2020 | Amann et al. | |
| 2020/0190206 | A1 | 6/2020 | Koller et al. | |
| 2020/0270321 | A1 | 8/2020 | Amann et al. | |
| 2020/0325225 | A1 | 10/2020 | Bacac et al. | |
| 2020/0325238 | A1 | 10/2020 | Bacac et al. | |
| 2020/0347115 | A1 | 11/2020 | Duerr et al. | |
| 2021/0024610 | A1 | 1/2021 | Koller et al. | |
| 2021/0054071 | A1* | 2/2021 | Zhang | A61P 35/00 |
| 2021/0095002 | A1 | 4/2021 | Claus et al. | |
| 2021/0163562 | A1* | 6/2021 | Lu | C07K 14/54 |
| 2021/0163617 | A1 | 6/2021 | Ferrara et al. | |
| 2021/0253724 | A1 | 8/2021 | Claus et al. | |
| 2021/0324108 | A1 | 10/2021 | Amann et al. | |
| 2022/0025069 | A1 | 1/2022 | Claus et al. | |
| 2022/0073646 | A1 | 3/2022 | Amann et al. | |
| 2022/0267395 | A1 | 8/2022 | Amann et al. | |
| 2023/0123178 | A1 | 4/2023 | Koller et al. | |

FOREIGN PATENT DOCUMENTS

| | | | |
|---|---|---|---|
| JP | 2019-524053 | A | 9/2019 |
| KR | 2019-0004802 | A | 1/2019 |
| WO | 2010/077634 | A1 | 7/2010 |
| WO | 2020/260329 | A1 | 12/2010 |
| WO | 2012/130831 | A1 | 10/2012 |
| WO | 2015/150447 | A1 | 10/2015 |
| WO | 2016/200835 | A1 | 12/2016 |
| WO | 2017/123650 | A2 | 7/2017 |
| WO | 2017/194641 | A1 | 11/2017 |
| WO | 2018/127917 | A1 | 7/2018 |
| WO | WO 2018144514 | * | 9/2018 |
| WO | 2019/072868 | A1 | 4/2019 |
| WO | 2019/094574 | A1 | 5/2019 |
| WO | 2019/108755 | A1 | 6/2019 |
| WO | 2020/007817 | A1 | 1/2020 |
| WO | 2021/140130 | A1 | 7/2021 |

OTHER PUBLICATIONS

Diehl, L., et al., "In Vivo Triggering Through 4-1BB Enables Th-Independent Priming of CTL in the Presence of an Intact CD28 Costimulatory Pathway" J Immunol 168(8):3755-3762 (Apr. 15, 2002).

Dubrot, J., et al., "Treatment with anti-CD137 mAbs causes intense accumulations of liver T cells without selective antitumor immunotherapeutic effects in this organ" Cancer Immunol Immun 59(8):1223-1233 (Aug. 1, 2010).

Goodwin, R., et al., "Molecular cloning of a ligand for the inducible T cell gene 4-1BB: a member of an emerging family of cytokines with homology to tumor necrosis factor" Eur J Immunol 23(10):2631-2641 (Oct. 1, 1993).

Ho, S.K., et al., "Epitope and Fc-Mediated Cross-linking, but Not High Affinity, are Critical for Antitumor Activity of CD137 Agonist Antibody with Reduced Liver Toxicity" Mol Cancer Ther 19(4):1040-1051 (Apr. 1, 2020).

Kwon, B., et al., "cDNA sequences of two inducible T-cell genes" PNAS USA 86(6):1963-1967 (Mar. 1, 1989).

Lee, H.W., et al., "4-1BB promotes the survival of CD8+ T lymphocytes by increasing expression of Bcl-xL and Bfl-1" J Immunol 169(9):4882-4888 (Nov. 1, 2002).

Li, F., et al., "Innhibitory Fcy receptor engagement drives adjuvant and anti-tumor activities of agonistic CD40 antibodies" Science 333(6045):1030-1034 (Aug. 19, 2011).

Liljeblad, M., et al., "Analysis of agalacto-IgG in rheumatoid arthritis using surface plasmon resonance" Glycoconjugate J 17:323-329 (Jul. 14, 2000).

Melero, I. et al., "Monoclonal Antibodies Against the 4-1BB T-cell Activation Molecule Eradicate Established Tumors" Nat Med 3(6):682-685 (Jun. 1, 1997).

Shao, Z., et al., "Mini-Review: CD137 ligand, a member of the tumor necrosis factor family, regulates immune responses via reverse signal transduction" J Leukocyte Biol 89(1):21-29 (Jan. 1, 2011).

Simeone, E. et al., "Immunomodulating antibodies in the treatment of metastatic melanoma: The experience with anti-CTLA-4, anti-CD137, and anti-PD1" J Immunotoxcity 9(3):241-247 (Jul. 1, 2012).

Snell, L., et al., "T-cell intrinsic effects of GITR and 4-1BB during viral infection and cancer immunotherapy" Immunol Rev 244(1):197-217 (Nov. 1, 2011).

US clinicaltrials.gov et al., "Phase II, 2nd Line Melanoma—RAND Monotherapy" (Clinical Trials Identifier—NCT00612664-Urelumab),:1-6 (Oct. 12, 2015).

US clinicaltrials.gov et al., "Study of BMS-663513 in Patients With Advanced Cancer" (Clinical Trials Identifier—NCT00309023-Urelumab),:1-6 (Oct. 12, 2015).

Vinay, D. et al., "4-1BB signaling beyond T cells" Cell Mol Immunol 8(4):281-284 (Jul. 1, 2011).

Zhang, N., et al., "Targeted and untargeted CD137L fusion proteins for the immunotherapy of experimental solid tumors" Clin Cancer Res 13(9):2758-2767 (May 1, 2007).

* cited by examiner

Fig. 3A huPD-L1-Fc (Analyte 2)

Bispecific construct (Analyte 1)

Hu4-1BB Fc(kih)

Fig. 3B

Response (0 = dual_baseline)

RU

Time (0 = dual_baseline)

s

MKN45
Geo Mean of Fluorescence
goat F(ab')2 anti-human Fcγ-PE
[baseline corrected]
40000
30000
20000
10000
0
0.001
0.01
0.1
1
10
100
Concentration [nM]

MKN45-huPD-L1
40000
30000
20000
10000
0
0.001
0.01
0.1
1
10
100
Concentration [nM]
P1AD4309 DP47-4-1BBL
P1AE8516 PDL1-4-1BBL
P1AE9315 4-1BB x PDL1 2+1
P1AE9316 4-1BB x PDL1 1+1
P1AD5108 DP47 IgG1
P1AD1946 4-1BB IgG1

No target cells
URLs [0.5s/well]
(Luciferase activity)
[baseline corrected]
80000
60000
40000
20000
0
0.0001
0.001
0.01
0.1
1
10
Concentration [nM]
P1AE8516 PDL1-4-1BBL
P1AD4309 DP47-4-1BBL MKN45
80000
60000
40000
20000
0
0.0001
0.001
0.01
0.1
1
10
Concentration [nM]
P1AE9315 4-1BB x PDL1 2+1
P1AE9316 4-1BB x PDL1 1+1
P1AD1946 4-1BB IgG MKN45-huPD-L1
80000
60000
40000
20000
0
0.0001
0.001
0.01
0.1
1
10
Concentration [nM]

SEQUENCE LISTING

```
Sequence total quantity: 60
SEQ ID NO: 1            moltype = AA  length = 184
FEATURE                 Location/Qualifiers
source                  1..184
                        mol_type = protein
                        organism = Homo sapiens
SEQUENCE: 1
REGPELSPDD PAGLLDLRQG MFAQLVAQNV LLIDGPLSWY SDPGLAGVSL TGGLSYKEDT  60
KELVVAKAGV YYVFFQLELR RVVAGEGSGS VSLALHLQPL RSAAGAAALA LTVDLPPASS  120
EARNSAFGFQ GRLLHLSAGQ RLGVHLHTEA RARHAWQLTQ GATVLGLFRV TPEIPAGLPS  180
PRSE                                                              184

SEQ ID NO: 2            moltype = AA  length = 170
FEATURE                 Location/Qualifiers
source                  1..170
                        mol_type = protein
                        organism = Homo sapiens
SEQUENCE: 2
LDLRQGMFAQ LVAQNVLLID GPLSWYSDPG LAGVSLTGGL SYKEDTKELV VAKAGVYYVF  60
FQLELRRVVA GEGSGSVSLA LHLQPLRSAA GAAALALTVD LPPASSEARN SAFGFQGRLL  120
HLSAGQRLGV HLHTEARARH AWQLTQGATV LGLFRVTPEI PAGLPSPRSE            170

SEQ ID NO: 3            moltype = AA  length = 175
FEATURE                 Location/Qualifiers
source                  1..175
                        mol_type = protein
                        organism = Homo sapiens
SEQUENCE: 3
DPAGLLDLRQ GMFAQLVAQN VLLIDGPLSW YSDPGLAGVS LTGGLSYKED TKELVVAKAG  60
VYYVFFQLEL RRVVAGEGSG SVSLALHLQP LRSAAGAAAL ALTVDLPPAS SEARNSAFGF  120
QGRLLHLSAG QRLGVHLHTE ARARHAWQLT QGATVLGLFR VTPEIPAGLP SPRSE       175

SEQ ID NO: 4            moltype = AA  length = 203
FEATURE                 Location/Qualifiers
source                  1..203
                        mol_type = protein
                        organism = Homo sapiens
SEQUENCE: 4
PWAVSGARAS PGSAASPRLR EGPELSPDDP AGLLDLRQGM FAQLVAQNVL LIDGPLSWYS  60
DPGLAGVSLT GGLSYKEDTK ELVVAKAGVY YVFFQLELRR VVAGEGSGSV SLALHLQPLR  120
SAAGAAALAL TVDLPPASSE ARNSAFGFQG RLLHLSAGQR LGVHLHTEAR ARHAWQLTQG  180
ATVLGLFRVT PEIPAGLPSP RSE                                         203

SEQ ID NO: 5            moltype = AA  length = 178
FEATURE                 Location/Qualifiers
source                  1..178
                        mol_type = protein
                        organism = Homo sapiens
SEQUENCE: 5
REGPELSPDD PAGLLDLRQG MFAQLVAQNV LLIDGPLSWY SDPGLAGVSL TGGLSYKEDT  60
KELVVAKAGV YYVFFQLELR RVVAGEGSGS VSLALHLQPL RSAAGAAALA LTVDLPPASS  120
EARNSAFGFQ GRLLHLSAGQ RLGVHLHTEA RARHAWQLTQ GATVLGLFRV TPEIPAGL    178

SEQ ID NO: 6            moltype = AA  length = 164
FEATURE                 Location/Qualifiers
source                  1..164
                        mol_type = protein
                        organism = Homo sapiens
SEQUENCE: 6
LDLRQGMFAQ LVAQNVLLID GPLSWYSDPG LAGVSLTGGL SYKEDTKELV VAKAGVYYVF  60
FQLELRRVVA GEGSGSVSLA LHLQPLRSAA GAAALALTVD LPPASSEARN SAFGFQGRLL  120
HLSAGQRLGV HLHTEARARH AWQLTQGATV LGLFRVTPEI PAGL                  164

SEQ ID NO: 7            moltype = AA  length = 169
FEATURE                 Location/Qualifiers
source                  1..169
                        mol_type = protein
                        organism = Homo sapiens
SEQUENCE: 7
DPAGLLDLRQ GMFAQLVAQN VLLIDGPLSW YSDPGLAGVS LTGGLSYKED TKELVVAKAG  60
VYYVFFQLEL RRVVAGEGSG SVSLALHLQP LRSAAGAAAL ALTVDLPPAS SEARNSAFGF  120
QGRLLHLSAG QRLGVHLHTE ARARHAWQLT QGATVLGLFR VTPEIPAGL             169

SEQ ID NO: 8            moltype = AA  length = 197
FEATURE                 Location/Qualifiers
source                  1..197
                        mol_type = protein
                        organism = Homo sapiens
```

```
SEQUENCE: 8
PWAVSGARAS PGSAASPRLR EGPELSPDDP AGLLDLRQGM FAQLVAQNVL LIDGPLSWYS  60
DPGLAGVSLT GGLSYKEDTK ELVVAKAGVY YVFFQLELRR VVAGEGSGSV SLALHLQPLR  120
SAAGAAALAL TVDLPPASSE ARNSAFGFQG RLLHLSAGQR LGVHLHTEAR ARHAWQLTQG  180
ATVLGLFRVT PEIPAGL                                                 197

SEQ ID NO: 9           moltype = AA  length = 378
FEATURE                Location/Qualifiers
REGION                 1..378
                       note = dimeric hu 4-1BBL (71-254) connected by (G4S)2 linker
source                 1..378
                       mol_type = protein
                       organism = synthetic construct
SEQUENCE: 9
REGPELSPDD PAGLLDLRQG MFAQLVAQNV LLIDGPLSWY SDPGLAGVSL TGGLSYKEDT  60
KELVVAKAGV YYVFFQLELR RVVAGEGSGS VSLALHLQPL RSAAGAAALA LTVDLPPASS  120
EARNSAFGFQ GRLLHLSAGQ RLGVHLHTEA RARHAWQLTQ GATVLGLFRV TPEIPAGLPS  180
PRSEGGGGSG GGGSREGPEL SPDDPAGLLD LRQGMFAQLV AQNVLLIDGP LSWYSDPGLA  240
GVSLTGGLSY KEDTKELVVA KAGVYYVFFQ LELRRVVAGE GSGSVSLALH LQPLRSAAGA  300
AALALTVDLP PASSEARNSA FGFQGRLLHL SAGQRLGVHL HTEARARHAW QLTQGATVLG  360
LFRVTPEIPA GLPSPRSE                                                378

SEQ ID NO: 10          moltype = AA  length = 366
FEATURE                Location/Qualifiers
REGION                 1..366
                       note = dimeric hu 4-1BBL (71-248) connected by (G4S)2 linker
source                 1..366
                       mol_type = protein
                       organism = synthetic construct
SEQUENCE: 10
REGPELSPDD PAGLLDLRQG MFAQLVAQNV LLIDGPLSWY SDPGLAGVSL TGGLSYKEDT  60
KELVVAKAGV YYVFFQLELR RVVAGEGSGS VSLALHLQPL RSAAGAAALA LTVDLPPASS  120
EARNSAFGFQ GRLLHLSAGQ RLGVHLHTEA RARHAWQLTQ GATVLGLFRV TPEIPAGLGG  180
GGSGGGGSRE GPELSPDDPA GLLDLRQGMF AQLVAQNVLL IDGPLSWYSD PGLAGVSLTG  240
GLSYKEDTKE LVVAKAGVYY VFFQLELRRV VAGEGSGSVS LALHLQPLRS AAGAAALALT  300
VDLPPASSEA RNSAFGFQGR LLHLSAGQRL GVHLHTEARA RHAWQLTQGA TVLGLFRVTP  360
EIPAGL                                                             366

SEQ ID NO: 11          moltype = AA  length = 360
FEATURE                Location/Qualifiers
REGION                 1..360
                       note = dimeric hu 4-1BBL (80-254) connected by (G4S)2 linker
source                 1..360
                       mol_type = protein
                       organism = synthetic construct
SEQUENCE: 11
DPAGLLDLRQ GMFAQLVAQN VLLIDGPLSW YSDPGLAGVS LTGGLSYKED TKELVVAKAG  60
VYYVFFQLEL RRVVAGEGSG SVSLALHLQP LRSAAGAAAL ALTVDLPPAS SEARNSAFGF  120
QGRLLHLSAG QRLGVHLHTE ARARHAWQLT QGATVLGLFR VTPEIPAGLP SPRSEGGGGS  180
GGGGSDPAGL LDLRQGMFAQ LVAQNVLLID GPLSWYSDPG LAGVSLTGGL SYKEDTKELV  240
VAKAGVYYVF FQLELRRVVA GEGSGSVSLA LHLQPLRSAA GAAALALTVD LPPASSEARN  300
SAFGFQGRLL HLSAGQRLGV HLHTEARARH AWQLTQGATV LGLFRVTPEI PAGLPSPRSE  360

SEQ ID NO: 12          moltype = AA  length = 416
FEATURE                Location/Qualifiers
REGION                 1..416
                       note = dimeric hu 4-1BBL (52-254) connected by (G4S)2 linker
source                 1..416
                       mol_type = protein
                       organism = synthetic construct
SEQUENCE: 12
PWAVSGARAS PGSAASPRLR EGPELSPDDP AGLLDLRQGM FAQLVAQNVL LIDGPLSWYS  60
DPGLAGVSLT GGLSYKEDTK ELVVAKAGVY YVFFQLELRR VVAGEGSGSV SLALHLQPLR  120
SAAGAAALAL TVDLPPASSE ARNSAFGFQG RLLHLSAGQR LGVHLHTEAR ARHAWQLTQG  180
ATVLGLFRVT PEIPAGLPSP RSEGGGGSGG GGSPWAVSGA RASPGSAASP RLREGPELSP  240
DDPAGLLDLR QGMFAQLVAQ NVLLIDGPLS WYSDPGLAGV SLTGGLSYKE DTKELVVAKA  300
GVYYVFFQLE LRRVVAGEGS GSVSLALHLQ PLRSAAGAAA LALTVDLPPA SSEARNSAFG  360
FQGRLLHLSA GQRLGVHLHT EARARHAWQL TQGATVLGLF RVTPEIPAGL PSPRSE      416

SEQ ID NO: 13          moltype = AA  length = 5
FEATURE                Location/Qualifiers
REGION                 1..5
                       note = PD-L1 CDR-H1
source                 1..5
                       mol_type = protein
                       organism = synthetic construct
SEQUENCE: 13
DSWIH                                                              5
```

```
SEQ ID NO: 14           moltype = AA  length = 17
FEATURE                 Location/Qualifiers
REGION                  1..17
                        note = PD-L1 CDR-H2
source                  1..17
                        mol_type = protein
                        organism = synthetic construct
SEQUENCE: 14
WISPYGGSTY YADSVKG                                                17

SEQ ID NO: 15           moltype = AA  length = 9
FEATURE                 Location/Qualifiers
REGION                  1..9
                        note = PD-L1 CDR-H3
source                  1..9
                        mol_type = protein
                        organism = synthetic construct
SEQUENCE: 15
RHWPGGFDY                                                         9

SEQ ID NO: 16           moltype = AA  length = 11
FEATURE                 Location/Qualifiers
REGION                  1..11
                        note = PD-L1 CDR-L1
source                  1..11
                        mol_type = protein
                        organism = synthetic construct
SEQUENCE: 16
RASQDVSTAV A                                                      11

SEQ ID NO: 17           moltype = AA  length = 7
FEATURE                 Location/Qualifiers
REGION                  1..7
                        note = PD-L1 CDR-L2
source                  1..7
                        mol_type = protein
                        organism = synthetic construct
SEQUENCE: 17
SASFLYS                                                           7

SEQ ID NO: 18           moltype = AA  length = 9
FEATURE                 Location/Qualifiers
REGION                  1..9
                        note = PD-L1 CDR-L3
source                  1..9
                        mol_type = protein
                        organism = synthetic construct
SEQUENCE: 18
QQYLYHPAT                                                         9

SEQ ID NO: 19           moltype = AA  length = 118
FEATURE                 Location/Qualifiers
REGION                  1..118
                        note = PD-L1 VH
source                  1..118
                        mol_type = protein
                        organism = synthetic construct
SEQUENCE: 19
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSS    118

SEQ ID NO: 20           moltype = AA  length = 107
FEATURE                 Location/Qualifiers
REGION                  1..107
                        note = PD-L1 VL
source                  1..107
                        mol_type = protein
                        organism = synthetic construct
SEQUENCE: 20
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIK                107

SEQ ID NO: 21           moltype = AA  length = 708
FEATURE                 Location/Qualifiers
REGION                  1..708
                        note = Dimeric 4-1BB ligand (71-248) - CL* Fc knob chain
source                  1..708
                        mol_type = protein
                        organism = synthetic construct
```

```
SEQUENCE: 21
REGPELSPDD PAGLLDLRQG MFAQLVAQNV LLIDGPLSWY SDPGLAGVSL TGGLSYKEDT  60
KELVVAKAGV YYVFFQLELR RVVAGEGSGS VSLALHLQPL RSAAGAAALA LTVDLPPASS  120
EARNSAFGFQ GRLLHLSAGQ RLGVHLHTEA RARHAWQLTQ GATVLGLFRV TPEIPAGLGG  180
GGSGGGGSRE GPELSPDDPA GLLDLRQGMF AQLVAQNVLL IDGPLSWYSD PGLAGVSLTG  240
GLSYKEDTKE LVVAKAGVYY VFFQLELRRV VAGEGSGSVS LALHLQPLRS AAGAAALALT  300
VDLPPASSEA RNSAFGFQGR LLHLSAGQRL GVHLHTEARA RHAWQLTQGA TVLGLFRVTP  360
EIPAGLGGGG SGGGGSRTVA APSVFIFPPS DRKLKSGTAS VVCLLNNFYP REAKVQWKVD  420
NALQSGNSQE SVTEQDSKDS TYSLSSTLTL SKADYEKHKV YACEVTHQGL SSPVTKSFNR  480
GECDKTHTCP PCPAPEAAGG PSVFLFPPKP KDTLMISRTP EVTCVVVDVS HEDPEVKFNW  540
YVDGVEVHNA KTKPREEQYN STYRVVSVLT VLHQDWLNGK EYKCKVSNKA LGAPIEKTIS  600
KAKGQPREPQ VYTLPPCRDE LTKNQVSLWC LVKGFYPSDI AVEWESNGQP ENNYKTTPPV  660
LDSDGSFFLY SKLTVDKSRW QQGNVFSCSV MHEALHNHYT QKSLSLSP              708

SEQ ID NO: 22          moltype = AA  length = 291
FEATURE                Location/Qualifiers
REGION                 1..291
                       note = Monomeric 4-1BB ligand (71-248)-CH1*
source                 1..291
                       mol_type = protein
                       organism = synthetic construct
SEQUENCE: 22
REGPELSPDD PAGLLDLRQG MFAQLVAQNV LLIDGPLSWY SDPGLAGVSL TGGLSYKEDT  60
KELVVAKAGV YYVFFQLELR RVVAGEGSGS VSLALHLQPL RSAAGAAALA LTVDLPPASS  120
EARNSAFGFQ GRLLHLSAGQ RLGVHLHTEA RARHAWQLTQ GATVLGLFRV TPEIPAGLGG  180
GGSGGGGSAS TKGPSVFPLA PSSKSTSGGT AALGCLVEDY FPEPVTVSWN SGALTSGVHT  240
FPAVLQSSGL YSLSSVVTVP SSSLGTQTYI CNVNHKPSNT KVDEKVEPKS C           291

SEQ ID NO: 23          moltype = AA  length = 708
FEATURE                Location/Qualifiers
REGION                 1..708
                       note = Dimeric 4-1BB ligand (71-248) - CL Fc knob chain
source                 1..708
                       mol_type = protein
                       organism = synthetic construct
SEQUENCE: 23
REGPELSPDD PAGLLDLRQG MFAQLVAQNV LLIDGPLSWY SDPGLAGVSL TGGLSYKEDT  60
KELVVAKAGV YYVFFQLELR RVVAGEGSGS VSLALHLQPL RSAAGAAALA LTVDLPPASS  120
EARNSAFGFQ GRLLHLSAGQ RLGVHLHTEA RARHAWQLTQ GATVLGLFRV TPEIPAGLGG  180
GGSGGGGSRE GPELSPDDPA GLLDLRQGMF AQLVAQNVLL IDGPLSWYSD PGLAGVSLTG  240
GLSYKEDTKE LVVAKAGVYY VFFQLELRRV VAGEGSGSVS LALHLQPLRS AAGAAALALT  300
VDLPPASSEA RNSAFGFQGR LLHLSAGQRL GVHLHTEARA RHAWQLTQGA TVLGLFRVTP  360
EIPAGLGGGG SGGGGSRTVA APSVFIFPPS DEQLKSGTAS VVCLLNNFYP REAKVQWKVD  420
NALQSGNSQE SVTEQDSKDS TYSLSSTLTL SKADYEKHKV YACEVTHQGL SSPVTKSFNR  480
GECDKTHTCP PCPAPEAAGG PSVFLFPPKP KDTLMISRTP EVTCVVVDVS HEDPEVKFNW  540
YVDGVEVHNA KTKPREEQYN STYRVVSVLT VLHQDWLNGK EYKCKVSNKA LGAPIEKTIS  600
KAKGQPREPQ VYTLPPCRDE LTKNQVSLWC LVKGFYPSDI AVEWESNGQP ENNYKTTPPV  660
LDSDGSFFLY SKLTVDKSRW QQGNVFSCSV MHEALHNHYT QKSLSLSP              708

SEQ ID NO: 24          moltype = AA  length = 291
FEATURE                Location/Qualifiers
REGION                 1..291
                       note = Monomeric 4-1BB ligand (71-248)-CH1
source                 1..291
                       mol_type = protein
                       organism = synthetic construct
SEQUENCE: 24
REGPELSPDD PAGLLDLRQG MFAQLVAQNV LLIDGPLSWY SDPGLAGVSL TGGLSYKEDT  60
KELVVAKAGV YYVFFQLELR RVVAGEGSGS VSLALHLQPL RSAAGAAALA LTVDLPPASS  120
EARNSAFGFQ GRLLHLSAGQ RLGVHLHTEA RARHAWQLTQ GATVLGLFRV TPEIPAGLGG  180
GGSGGGGSAS TKGPSVFPLA PSSKSTSGGT AALGCLVKDY FPEPVTVSWN SGALTSGVHT  240
FPAVLQSSGL YSLSSVVTVP SSSLGTQTYI CNVNHKPSNT KVDKKVEPKS C           291

SEQ ID NO: 25          moltype = AA  length = 720
FEATURE                Location/Qualifiers
REGION                 1..720
                       note = Dimeric 4-1BB ligand (71-254) - CL* Fc knob chain
source                 1..720
                       mol_type = protein
                       organism = synthetic construct
SEQUENCE: 25
REGPELSPDD PAGLLDLRQG MFAQLVAQNV LLIDGPLSWY SDPGLAGVSL TGGLSYKEDT  60
KELVVAKAGV YYVFFQLELR RVVAGEGSGS VSLALHLQPL RSAAGAAALA LTVDLPPASS  120
EARNSAFGFQ GRLLHLSAGQ RLGVHLHTEA RARHAWQLTQ GATVLGLFRV TPEIPAGLPS  180
PRSEGGGGSG GGGSREGPEL SPDDPAGLLD LRQGMFAQLV AQNVLLIDGP LSWYSDPGLA  240
GVSLTGGLSY KEDTKELVVA KAGVYYVFFQ LELRRVVAGE GSGSVSLALH LQPLRSAAGA  300
AALALTVDLP PASSEARNSA FGFQGRLLHL SAGQRLGVHL HTEARARHAW QLTQGATVLG  360
LFRVTPEIPA GLPSPRSEGG GGSGGGGSRT VAAPSVFIFP PSDRKLKSGT ASVVCLLNNF  420
YPREAKVQWK VDNALQSGNS QESVTEQDSK DSTYSLSSTL TLSKADYEKH KVYACEVTHQ  480
```

```
GLSSPVTKSF NRGECDKTHT CPPCPAPEAA GGPSVFLFPP KPKDTLMISR TPEVTCVVVD  540
VSHEDPEVKF NWYVDGVEVH NAKTKPREEQ YNSTYRVVSV LTVLHQDWLN GKEYKCKVSN  600
KALGAPIEKT ISKAKGQPRE PQVYTLPPCR DELTKNQVSL WCLVKGFYPS DIAVEWESNG  660
QPENNYKTTP PVLDSDGSFF LYSKLTVDKS RWQQGNVFSC SVMHEALHNH YTQKSLSLSP  720

SEQ ID NO: 26          moltype = AA  length = 297
FEATURE                Location/Qualifiers
REGION                 1..297
                       note = Monomeric 4-1BB ligand (71-254)-CH1*
source                 1..297
                       mol_type = protein
                       organism = synthetic construct
SEQUENCE: 26
REGPELSPDD PAGLLDLRQG MFAQLVAQNV LLIDGPLSWY SDPGLAGVSL TGGLSYKEDT  60
KELVVAKAGV YYVFFQLELR RVVAGEGSGS VSLALHLQPL RSAAGAAALA LTVDLPPASS  120
EARNSAFGFQ GRLLHLSAGQ RLGVHLHTEA RARHAWQLTQ GATVLGLFRV TPEIPAGLPS  180
PRSEGGGGSG GGGSASTKGP SVFPLAPSSK STSGGTAALG CLVEDYFPEP VTVSWNSGAL  240
TSGVHTFPAV LQSSGLYSLS SVVTVPSSSL GTQTYICNVN HKPSNTKVDE KVEPKSC     297

SEQ ID NO: 27          moltype = AA  length = 720
FEATURE                Location/Qualifiers
REGION                 1..720
                       note = Dimeric 4-1BB ligand (71-254) - CL Fc knob chain
source                 1..720
                       mol_type = protein
                       organism = synthetic construct
SEQUENCE: 27
REGPELSPDD PAGLLDLRQG MFAQLVAQNV LLIDGPLSWY SDPGLAGVSL TGGLSYKEDT  60
KELVVAKAGV YYVFFQLELR RVVAGEGSGS VSLALHLQPL RSAAGAAALA LTVDLPPASS  120
EARNSAFGFQ GRLLHLSAGQ RLGVHLHTEA RARHAWQLTQ GATVLGLFRV TPEIPAGLPS  180
PRSEGGGGSG GGGSREGPEL SPDDPAGLLD LRQGMFAQLV AQNVLLIDGP LSWYSDPGLA  240
GVSLTGGLSY KEDTKELVVA KAGVYYVFFQ LELRRVVAGE GSGSVSLALH LQPLRSAAGA  300
AALALTVDLP PASSEARNSA FGFQGRLLHL SAGQRLGVHL HTEARARHAW QLTQGATVLG  360
LFRVTPEIPA GLPSPRSEGG GGSGGGGSRT VAAPSVFIFP PSDEQLKSGT ASVVCLLNNF  420
YPREAKVQWK VDNALQSGNS QESVTEQDSK DSTYSLSSTL TLSKADYEKH KVYACEVTHQ  480
GLSSPVTKSF NRGECDKTHT CPPCPAPEAA GGPSVFLFPP KPKDTLMISR TPEVTCVVVD  540
VSHEDPEVKF NWYVDGVEVH NAKTKPREEQ YNSTYRVVSV LTVLHQDWLN GKEYKCKVSN  600
KALGAPIEKT ISKAKGQPRE PQVYTLPPCR DELTKNQVSL WCLVKGFYPS DIAVEWESNG  660
QPENNYKTTP PVLDSDGSFF LYSKLTVDKS RWQQGNVFSC SVMHEALHNH YTQKSLSLSP  720

SEQ ID NO: 28          moltype = AA  length = 297
FEATURE                Location/Qualifiers
REGION                 1..297
                       note = Monomeric 4-1BB ligand (71-254) -CH1
source                 1..297
                       mol_type = protein
                       organism = synthetic construct
SEQUENCE: 28
REGPELSPDD PAGLLDLRQG MFAQLVAQNV LLIDGPLSWY SDPGLAGVSL TGGLSYKEDT  60
KELVVAKAGV YYVFFQLELR RVVAGEGSGS VSLALHLQPL RSAAGAAALA LTVDLPPASS  120
EARNSAFGFQ GRLLHLSAGQ RLGVHLHTEA RARHAWQLTQ GATVLGLFRV TPEIPAGLPS  180
PRSEGGGGSG GGGSASTKGP SVFPLAPSSK STSGGTAALG CLVKDYFPEP VTVSWNSGAL  240
TSGVHTFPAV LQSSGLYSLS SVVTVPSSSL GTQTYICNVN HKPSNTKVDK KVEPKSC     297

SEQ ID NO: 29          moltype = AA  length = 446
FEATURE                Location/Qualifiers
REGION                 1..446
                       note = anti-PD-L1 Fc hole chain
source                 1..446
                       mol_type = protein
                       organism = synthetic construct
SEQUENCE: 29
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALG APIEKTISKA KGQPREPQVC TLPPSRDELT  360
KNQVSLSCAV KGFYPSDIAV EWESNGQPEN NYKTTPPVLD SDGSFFLVSK LTVDKSRWQQ  420
GNVFSCSVMH EALHNHYTQK SLSLSP                                      446

SEQ ID NO: 30          moltype = AA  length = 214
FEATURE                Location/Qualifiers
REGION                 1..214
                       note = anti-PD-L1 light chain
source                 1..214
                       mol_type = protein
                       organism = synthetic construct
SEQUENCE: 30
```

```
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 31          moltype = AA  length = 443
FEATURE                Location/Qualifiers
REGION                 1..443
                       note = DP47 Fc hole chain
source                 1..443
                       mol_type = protein
                       organism = synthetic construct
SEQUENCE: 31
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAKGS GFDYWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSCDK THTCPPCPAP EAAGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALGAPI EKTISKAKGQ PREPQVCTLP PSRDELTKNQ  360
VSLSCAVKGF YPSDIAVEWE SNGQPENNYK TTPPVLDSDG SFFLVSKLTV DKSRWQQGNV  420
FSCSVMHEAL HNHYTQKSLS LSP                                          443

SEQ ID NO: 32          moltype = AA  length = 215
FEATURE                Location/Qualifiers
REGION                 1..215
                       note = DP47 light chain
source                 1..215
                       mol_type = protein
                       organism = synthetic construct
SEQUENCE: 32
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPLTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 33          moltype = AA  length = 163
FEATURE                Location/Qualifiers
source                 1..163
                       mol_type = protein
                       organism = Homo sapiens
SEQUENCE: 33
LQDPCSNCPA GTFCDNNRNQ ICSPCPPNSF SSAGGQRTCD ICRQCKGVFR TRKECSSTSN  60
AECDCTPGFH CLGAGCSMCE QDCKQGQELT KKGCKDCCFG TFNDQKRGIC RPWTNCSLDG  120
KSVLVNGTKE RDVVCGPSPA DLSPGASSVT PPAPAREPGH SPQ                    163

SEQ ID NO: 34          moltype = AA  length = 225
FEATURE                Location/Qualifiers
REGION                 1..225
                       note = Fc hole chain
source                 1..225
                       mol_type = protein
                       organism = synthetic construct
SEQUENCE: 34
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSP                  225

SEQ ID NO: 35          moltype = AA  length = 422
FEATURE                Location/Qualifiers
REGION                 1..422
                       note = human 4-1BB antigen Fc knob chain
source                 1..422
                       mol_type = protein
                       organism = synthetic construct
SEQUENCE: 35
LQDPCSNCPA GTFCDNNRNQ ICSPCPPNSF SSAGGQRTCD ICRQCKGVFR TRKECSSTSN  60
AECDCTPGFH CLGAGCSMCE QDCKQGQELT KKGCKDCCFG TFNDQKRGIC RPWTNCSLDG  120
KSVLVNGTKE RDVVCGPSPA DLSPGASSVT PPAPAREPGH SPQVDEQLYF QGGSPKSADK  180
THTCPPCPAP ELLGGPSVFL FPPKPKDTLM ISRTPEVTCV VVDVSHEDPE VKFNWYVDGV  240
EVHNAKTKPR EEQYNSTYRV VSVLTVLHQD WLNGKEYKCK VSNKALPAPI EKTISKAKGQ  300
PREPQVYTLP PCRDELTKNQ VSLWCLVKGF YPSDIAVEWE SNGQPENNYK TTPPVLDSDG  360
SFFLYSKLTV DKSRWQQGNV FSCSVMHEAL HNHYTQKSLS LSPGKSGGLN DIFEAQKIEW  420
HE                                                                 422

SEQ ID NO: 36          moltype = AA  length = 10
FEATURE                Location/Qualifiers
REGION                 1..10
                       note = (G4S)2 peptide linker
```

```
source                  1..10
                        mol_type = protein
                        organism = synthetic construct
SEQUENCE: 36
GGGGSGGGGS                                                          10

SEQ ID NO: 37           moltype = AA  length = 290
FEATURE                 Location/Qualifiers
source                  1..290
                        mol_type = protein
                        organism = Homo sapiens
SEQUENCE: 37
MRIFAVFIFM TYWHLLNAFT VTVPKDLYVV EYGSNMTIEC KFPVEKQLDL AALIVYWEME  60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL FNVTSTLRIN TTTNEIFYCT FRRLDPEENH TAELVIPELP LAHPPNERTH  240
LVILGAILLC LGVALTFIFR LRKGRMMDVK KCGIQDTNSK KQSDTHLEET              290

SEQ ID NO: 38           moltype = AA  length = 254
FEATURE                 Location/Qualifiers
source                  1..254
                        mol_type = protein
                        organism = Homo sapiens
SEQUENCE: 38
MEYASDASLD PEAPWPPAPR ARACRVLPWA LVAGLLLLLL LAAACAVFLA CPWAVSGARA  60
SPGSAASPRL REGPELSPDD PAGLLDLRQG MFAQLVAQNV LLIDGPLSWY SDPGLAGVSL  120
TGGLSYKEDT KELVVAKAGV YYVFFQLELR RVVAGEGSGS VSLALHLQPL RSAAGAAALA  180
LTVDLPPASS EARNSAFGFQ GRLLHLSAGQ RLGVHLHTEA RARHAWQLTQ GATVLGLFRV  240
TPEIPAGLPS PRSE                                                     254

SEQ ID NO: 39           moltype = AA  length = 205
FEATURE                 Location/Qualifiers
source                  1..205
                        mol_type = protein
                        organism = Homo sapiens
SEQUENCE: 39
ACPWAVSGAR ASPGSAASPR LREGPELSPD DPAGLLDLRQ GMFAQLVAQN VLLIDGPLSW  60
YSDPGLAGVS LTGGLSYKED TKELVVAKAG VYYVFFQLEL RRVVAGEGSG SVSLALHLQP  120
LRSAAGAAAL ALTVDLPPAS SEARNSAFGF QGRLLHLSAG QRLGVHLHTE ARARHAWQLT  180
QGATVLGLFR VTPEIPAGLP SPRSE                                         205

SEQ ID NO: 40           moltype = AA  length = 5
FEATURE                 Location/Qualifiers
REGION                  1..5
                        note = Peptide linker
source                  1..5
                        mol_type = protein
                        organism = synthetic construct
SEQUENCE: 40
GGGGS                                                               5

SEQ ID NO: 41           moltype = AA  length = 10
FEATURE                 Location/Qualifiers
REGION                  1..10
                        note = Peptide linker
source                  1..10
                        mol_type = protein
                        organism = synthetic construct
SEQUENCE: 41
SGGGGSGGGG                                                          10

SEQ ID NO: 42           moltype = AA  length = 15
FEATURE                 Location/Qualifiers
REGION                  1..15
                        note = Peptide linker
source                  1..15
                        mol_type = protein
                        organism = synthetic construct
SEQUENCE: 42
GGGGSGGGGS GGGGS                                                    15

SEQ ID NO: 43           moltype = AA  length = 14
FEATURE                 Location/Qualifiers
REGION                  1..14
                        note = Peptide linker
source                  1..14
                        mol_type = protein
                        organism = synthetic construct
SEQUENCE: 43
```

```
GGGGSGGGGS GGGG                                              14

SEQ ID NO: 44           moltype = AA  length = 20
FEATURE                 Location/Qualifiers
REGION                  1..20
                        note = Peptide linker
source                  1..20
                        mol_type = protein
                        organism = synthetic construct
SEQUENCE: 44
GGGGSGGGGS GGGGSGGGGS                                        20

SEQ ID NO: 45           moltype = AA  length = 10
FEATURE                 Location/Qualifiers
REGION                  1..10
                        note = Peptide linker
source                  1..10
                        mol_type = protein
                        organism = synthetic construct
SEQUENCE: 45
GSPGSSSSGS                                                   10

SEQ ID NO: 46           moltype = AA  length = 8
FEATURE                 Location/Qualifiers
REGION                  1..8
                        note = Peptide linker
source                  1..8
                        mol_type = protein
                        organism = synthetic construct
SEQUENCE: 46
GSGSGSGS                                                     8

SEQ ID NO: 47           moltype = AA  length = 8
FEATURE                 Location/Qualifiers
REGION                  1..8
                        note = Peptide linker
source                  1..8
                        mol_type = protein
                        organism = synthetic construct
SEQUENCE: 47
GSGSGNGS                                                     8

SEQ ID NO: 48           moltype = AA  length = 8
FEATURE                 Location/Qualifiers
REGION                  1..8
                        note = Peptide linker
source                  1..8
                        mol_type = protein
                        organism = synthetic construct
SEQUENCE: 48
GGSGSGSG                                                     8

SEQ ID NO: 49           moltype = AA  length = 6
FEATURE                 Location/Qualifiers
REGION                  1..6
                        note = Peptide linker
source                  1..6
                        mol_type = protein
                        organism = synthetic construct
SEQUENCE: 49
GGSGSG                                                       6

SEQ ID NO: 50           moltype = AA  length = 4
FEATURE                 Location/Qualifiers
REGION                  1..4
                        note = Peptide linker
source                  1..4
                        mol_type = protein
                        organism = synthetic construct
SEQUENCE: 50
GGSG                                                         4

SEQ ID NO: 51           moltype = AA  length = 8
FEATURE                 Location/Qualifiers
REGION                  1..8
                        note = Peptide linker
source                  1..8
                        mol_type = protein
                        organism = synthetic construct
```

```
SEQUENCE: 51
GGSGNGSG                                                                  8

SEQ ID NO: 52          moltype = AA  length = 8
FEATURE                Location/Qualifiers
REGION                 1..8
                       note = Peptide linker
source                 1..8
                       mol_type = protein
                       organism = synthetic construct
SEQUENCE: 52
GGNGSGSG                                                                  8

SEQ ID NO: 53          moltype = AA  length = 6
FEATURE                Location/Qualifiers
REGION                 1..6
                       note = Peptide linker
source                 1..6
                       mol_type = protein
                       organism = synthetic construct
SEQUENCE: 53
GGNGSG                                                                    6

SEQ ID NO: 54          moltype = AA  length = 449
FEATURE                Location/Qualifiers
REGION                 1..449
                       note = VHCH1(EE) (20H4.9)-Heavy chain HC1 (Fc hole)
source                 1..449
                       mol_type = protein
                       organism = synthetic construct
SEQUENCE: 54
QVQLQQWGAG LLKPSETLSL TCAVYGGSFS GYYWSWIRQS PEKGLEWIGE INHGGYVTYN  60
PSLESRVTIS VDTSKNQFSL KLSSVTAADT AVYYCARDYG PGNYDWYFDL WGRGTLVTVS  120
SASTKGPSVF PLAPSSKSTS GGTAALGCLV EDYFPEPVTV SWNSGALTSG VHTFPAVLQS  180
SGLYSLSSVV TVPSSSLGTQ TYICNVNHKP SNTKVDEKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALGAPIEKTI SKAKGQPREP QVCTLPPSRD  360
ELTKNQVSLS CAVKGFYPSD IAVEWESNGQ PENNYKTTPP VLDSDGSFFL VSKLTVDKSR  420
WQQGNVFSCS VMHEALHNHY TQKSLSLSP                                   449

SEQ ID NO: 55          moltype = AA  length = 672
FEATURE                Location/Qualifiers
REGION                 1..672
                       note = VLCH1 (PD-L1) VHCH1(EE) (20H4.9) -Heavy chain HC2
                        (Fc knob)
source                 1..672
                       mol_type = protein
                       organism = synthetic construct
SEQUENCE: 55
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIKSSA STKGPSVFPL  120
APSSKSTSGG TAALGCLVKD YFPEPVTVSW NSGALTSGVH TFPAVLQSSG LYSLSSVVTV  180
PSSSLGTQTY ICNVNHKPSN TKVDKKVEPK SCDGGGGSGG GGSQVQLQQW GAGLLKPSET  240
LSLTCAVYGG SFSGYYWSWI RQSPEKGLEW IGEINHGGYV TYNPSLESRV TISVDTSKNQ  300
FSLKLSSVTA ADTAVYYCAR DYGPGNYDWY FDLWGRGTLV TVSSASTKGP SVFPLAPSSK  360
STSGGTAALG CLVEDYFPEP VTVSWNSGAL TSGVHTFPAV LQSSGLYSLS SVVTVPSSSL  420
GTQTYICNVN HKPSNTKVDE KVEPKSCDKT HTCPPCPAPE AAGGPSVFLF PPKPKDTLMI  480
SRTPEVTCVV VDVSHEDPEV KFNWYVDGVE VHNAKTKPRE EQYNSTYRVV SVLTVLHQDW  540
LNGKEYKCKV SNKALGAPIE KTISKAKGQP REPQVYTLPP CRDELTKNQV SLWCLVKGFY  600
PSDIAVEWES NGQPENNYKT TPPVLDSDGS FFLYSKLTVD KSRWQQGNVF SCSVMHEALH  660
NHYTQKSLSL SP                                                     672

SEQ ID NO: 56          moltype = AA  length = 216
FEATURE                Location/Qualifiers
REGION                 1..216
                       note = VLCL(RK)-Light chain (20H4.9)
source                 1..216
                       mol_type = protein
                       organism = synthetic construct
SEQUENCE: 56
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPPALTF GGGTKVEIKR TVAAPSVFIF  120
PPSDRKLKSG TASVVCLLNN FYPREAKVQW KVDNALQSGN SQESVTEQDS KDSTYSLSST  180
LTLSKADYEK HKVYACEVTH QGLSSPVTKS FNRGEC                           216

SEQ ID NO: 57          moltype = AA  length = 225
FEATURE                Location/Qualifiers
REGION                 1..225
                       note = VHCL-Light chain (PD-L1)
```

-continued

```
source                  1..225
                        mol_type = protein
                        organism = synthetic construct
SEQUENCE: 57
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSSAS  120
VAAPSVFIFP PSDEQLKSGT ASVVCLLNNF YPREAKVQWK VDNALQSGNS QESVTEQDSK  180
DSTYSLSSTL TLSKADYEKH KVYACEVTHQ GLSSPVTKSF NRGEC                  225

SEQ ID NO: 58           moltype = AA  length = 437
FEATURE                 Location/Qualifiers
REGION                  1..437
                        note = VLCH1 (PD-L1) -Heavy chain HC2 (Fc knob)
source                  1..437
                        mol_type = protein
                        organism = synthetic construct
SEQUENCE: 58
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIKSSA STKGPSVFPL  120
APSSKSTSGG TAALGCLVKD YFPEPVTVSW NSGALTSGVH TFPAVLQSSG LYSLSSVVTV  180
PSSSLGTQTY ICNVNHKPSN TKVDKKVEPK SCDKTHTCPP CPAPEAAGGP SVFLFPPKPK  240
DTLMISRTPE VTCVVVDVSH EDPEVKFNWY VDGVEVHNAK TKPREEQYNS TYRVVSVLTV  300
LHQDWLNGKE YKCKVSNKAL GAPIEKTISK AKGQPREPQV YTLPPCRDEL TKNQVSLWCL  360
VKGFYPSDIA VEWESNGQPE NNYKTTPPVL DSDGSFFLYS KLTVDKSRWQ QGNVFSCSVM  420
HEALHNHYTQ KSLSLSP                                                 437

SEQ ID NO: 59           moltype = AA  length = 207
FEATURE                 Location/Qualifiers
source                  1..207
                        mol_type = protein
                        organism = Homo sapiens
SEQUENCE: 59
MQSGTHWRVL GLCLLSVGVW GQDGNEEMGG ITQTPYKVSI SGTTVILTCP QYPGSEILWQ  60
HNDKNIGGDE DDKNIGSDED HLSLKEFSEL EQSGYYVCYP RGSKPEDANF YLYLRARVCE  120
NCMEMDVMSV ATIVIVDICI TGGLLLLVYY WSKNRKAKAK PVTRGAGAGG RQRGQNKERP  180
PPVPNPDYEP IRKGQRDLYS GLNQRRI                                      207

SEQ ID NO: 60           moltype = AA  length = 198
FEATURE                 Location/Qualifiers
source                  1..198
                        mol_type = protein
                        organism = Macaca fascicularis
SEQUENCE: 60
MQSGTRWRVL GLCLLSIGVW GQDGNEEMGS ITQTPYQVSI SGTTVILTCS QHLGSEAQWQ  60
HNGKNKEDSG DRLFLPEFSE MEQSGYYVCY PRGSNPEDAS HHLYLKARVC ENCMEMDVMA  120
VATIVIVDIC ITLGLLLLVY YWSKNRKAKA KPVTRGAGAG GRQRGQNKER PPPVPNPDYE  180
PIRKGQQDLY SGLNQRRI                                                198
```

4-1BBL TRIMER-CONTAINING ANTIGEN BINDING MOLECULES

CROSS-REFERENCE TO RELATED APPLICATIONS

This application is a Continuation of International Application No. PCT/EP2021/050145, filed Jan. 7, 2021, which claims the benefit of and priority to European Application No. 20151043.5, filed Jan. 9, 2020, each of which is incorporated herein by reference in its entirety.

SEQUENCE LISTING

This application contains a Sequence Listing which has been submitted electronically in XML format and is hereby incorporated by reference in its entirety. Said XML copy, created on Jul. 5, 2022, is named P35883-US.xml, and is 82,554 bytes in size.

FIELD OF THE INVENTION

The invention relates to 4-1BBL trimer-containing antigen binding molecules comprising an antigen binding domain capable of specific binding to PD-L1 and their use in the treatment of cancer. The invention further relates to methods of producing these molecules and to methods of using the same.

BACKGROUND 4-1BB (CD137), a member of the TNF receptor superfamily, was first identified as an inducible molecule expressed by activated T cells (Kwon and Weissman, 1989, Proc Natl Acad Sci USA 86, 1963-1967). Subsequent studies demonstrated that many other immune cells also express 4-1BB, including NK cells, B cells, NKT cells, monocytes, neutrophils, mast cells, dendritic cells (DCs) and cells of non-hematopoietic origin such as endothelial and smooth muscle cells (Vinay and Kwon, 2011, Cell Mol Immunol 8, 281-284). Expression of 4-1BB in different cell types is mostly inducible and driven by various stimulatory signals, such as T-cell receptor (TCR) or B-cell receptor triggering, as well as signaling induced through co-stimulatory molecules or receptors of pro-inflammatory cytokines (Diehl et al., 2002, J Immunol 168, 3755-3762; Zhang et al., 2010, Clin Cancer Res 13, 2758-2767).

4-1BB ligand (4-1BBL or CD137L) was identified in 1993 (Goodwin et al., 1993, Eur J Immunol 23, 2631-2641). It has been shown that expression of 4-1BBL was restricted on professional antigen presenting cells (APC) such as B-cells, DCs and macrophages. Inducible expression of 4-1BBL is characteristic for T-cells, including both αβ and γδ T-cell subsets, and endothelial cells (Shao and Schwarz, 2011, J Leukoc Biol 89, 21-29).

Co-stimulation through the 4-1BB receptor (for example by 4-1BBL ligation) activates multiple signaling cascades within the T cell (both $CD4^+$ and $CD8^+$ subsets), powerfully augmenting T cell activation (Bartkowiak and Curran, 2015). In combination with TCR triggering, agonistic 4-1BB-specific antibodies enhance proliferation of T-cells, stimulate lymphokine secretion and decrease sensitivity of T-lymphocytes to activation-induced cells death (Snell et al., 2011, Immunol Rev 244, 197-217). This mechanism was further advanced as the first proof of concept in cancer immunotherapy. In a preclinical model administration of an agonistic antibody against 4-1BB in tumor bearing mice led to potent anti-tumor effect (Melero et al., 1997, Nat Med 3, 682-685). Later, accumulating evidence indicated that 4-1BB usually exhibits its potency as an anti-tumor agent only when administered in combination with other immunomodulatory compounds, chemotherapeutic reagents, tumor-specific vaccination or radiotherapy (Bartkowiak and Curran, 2015, Front Oncol 5, 117).

Signaling of the TNFR-superfamily needs cross-linking of the trimerized ligands to engage with the receptors, so does the 4-1BB agonistic antibodies which require wild type Fc-binding (Li and Ravetch, 2011, Science 333, 1030-1034). However, systemic administration of 4-1BB-specific agonistic antibodies with the functionally active Fc domain resulted in influx of $CD8^+$ T-cells associated with liver toxicity (Dubrot et al., 2010, Cancer Immunol Immunother 59, 1223-1233) that is diminished or significantly ameliorated in the absence of functional Fc-receptors in mice. In the clinic, an Fc-competent 4-1BB agonistic Ab (BMS-663513) (NCI00612664) caused a grade 4 hepatitis leading to termination of the trial (Simeone and Ascierto, 2012, J Immunotoxicol 9, 241-247). Therefore, there is a need for effective and safer 4-1BB agonists.

Programmed death-ligand 1 (PD-L1) is a protein that has been implicated in the suppression of immune system responses during chronic infections, pregnancy, tissue allografts, autoimmune diseases, and cancer. PD-L1 regulates the immune response by binding to an inhibitory receptor, known as programmed death 1 (PD-1), which is expressed on the surface of T-cells, B-cells, and monocytes. PD-L1 negatively regulates T-cell function also through interaction with another receptor, B7-1. Formation of the PD-L1/PD-1 and PD-L1/B7-1 complexes negatively regulates T-cell receptor signaling, resulting in the subsequent downregulation of T-cell activation and suppression of anti-tumor immune activity. Currently, several PD-1 and PD-L1 antibodies are in clinical use for the treatment of various solid cancers and lymphomas, and blocking of the PD-1 pathway was shown to induce impressive response rates across a broad spectrum of tumor types. The marketed PD-L1 antibodies Atezolizumab (Tecentriq), Avelumab (Bavencio) and Durvalumab (Imfinzi) are meanwhile approved for different types of cancer such as urothelial carcinoma, non-small cell lung cancer, and merkel-cell carcinoma. Although immunotherapeutics targeting PD-1 or PD-L1 have made substantial clinical progress in cancer, a considerable proportion of patients remain unresponsive to treatment. Thus, there is still a need for new drug candidates that combine PD-L1 with co-stimulatory targets in order overcome immune resistance in the tumor environment.

SUMMARY OF THE INVENTION

The new antigen binding molecules of the present invention combine an anti-PD-L1 antigen binding domain with a moiety that is capable of forming a costimulatory 4-1BBL trimer and that is sufficiently stable to be pharmaceutically useful. Antigen binding molecules of the invention provide a trimeric and thus biologically active human 4-1BB ligand, although one of the trimerizing 4-1BBL ectodomains is located on another polypeptide than the other two 4-1BBL ectodomains of the molecule. Targeted by the anti-PD-L1 antigen binding domain the antigen binding molecules of the present invention have an increased activity on the tumor site, comprise the natural human 4-1BB ligand and should thus impose less safety issues compared to conventional 4-1BB agonistic antibodies or more artificial fusion proteins.

In one aspect, the invention provides a 4-1BBL trimer-containing antigen binding molecule comprising (a) an antigen binding domain capable of specific binding to PD-L1, (b) a first and a second polypeptide that are linked to each other by a disulfide bond, wherein the antigen binding molecule is characterized in that the first polypeptide comprises two ectodomains of 4-1BBL or a fragment thereof that are connected to each other by a peptide linker and in that the second polypeptide comprises one ectodomain of 4-1BBL or a fragment thereof, and (c) an Fc domain composed of a first and a second subunit capable of stable association.

In a particular aspect, the invention provides a 4-1BBL trimer-containing antigen binding molecule, wherein the ectodomain of 4-1BBL or a fragment thereof comprises the amino acid sequence selected from the group consisting of SEQ ID NO:1, SEQ ID NO: 2, SEQ ID NO:3, SEQ ID NO:4, SEQ ID NO:5, SEQ ID NO: 6, SEQ ID NO:7 and SEQ ID NO:8, particularly the amino acid sequence of SEQ ID NO:1 or SEQ ID NO:5.

In a further aspect, the invention provides a 4-1BBL trimer-containing antigen binding molecule, comprising (a) an antigen binding domain capable of specific binding to PD-L1, (b) a first and a second polypeptide that are linked to each other by a disulfide bond, wherein the antigen binding molecule is characterized in that the first polypeptide comprises the amino acid sequence selected from the group consisting of SEQ ID NO:9, SEQ ID NO:10, SEQ ID NO:11 and SEQ ID NO:12 and in that the second polypeptide comprises the amino acid sequence selected from the group consisting of SEQ ID NO:1, SEQ ID NO:5, SEQ ID NO:3 and SEQ ID NO:4, and (c) an Fc domain composed of a first and a second subunit capable of stable association.

In one aspect, the Fc domain is an IgG, particularly an IgG1 Fc domain or an IgG4 Fc domain. More particularly, the Fc domain is an IgG1 Fc domain. In a particular aspect, the Fc domain comprises a modification promoting the association of the first and second subunit of the Fc domain. In a particular aspect, the invention provides a 4-1BBL trimer-containing antigen binding molecule, wherein the Fc domain comprises knob-into-hole modifications promoting association of the first and the second subunit of the Fc domain. In a specific aspect, the invention provides a 4-1BBL trimer-containing antigen binding molecule, wherein the first subunit of the Fc domain comprises the amino acid substitutions S354C and T366W (numbering according to Kabat EU index) and the second subunit of the Fc domain comprises the amino acid substitutions Y349C, T366S, L368A and Y407V (numbering according to Kabat EU index).

In another aspect, the invention is concerned with a 4-1BBL trimer-containing antigen binding molecule as defined herein before, comprising (c) an Fc domain composed of a first and a second subunit capable of stable association, wherein the Fc domain comprises one or more amino acid substitution that reduces binding to an Fc receptor, in particular towards Fcγ receptor. In particular, the Fc domain comprises amino acid substitutions at positions 234 and 235 (EU numbering according to Kabat) and/or 329 (EU numbering according to Kabat) of the IgG heavy chains. Particularly, provided is a 4-1BBL trimer-containing antigen binding molecule, wherein the Fc domain is an IgG1 Fc domain comprising the amino acid substitutions the amino acid substitutions L234A, L235A and P329G (numbering according to Kabat EU index).

In one aspect, the 4-1BBL trimer-containing antigen binding molecule is one, wherein wherein the antigen binding domain capable of specific binding to PD-L1 is a Fab molecule capable of specific binding to PD-L1. In another aspect, the antigen binding domain capable of specific binding to PD-L1 is a cross-over Fab molecule or a scFV molecule capable of specific binding to PD-L1.

In one aspect, the invention provides a 4-1BBL trimer-containing antigen binding molecule as described herein before, wherein the 4-1BBL trimer-containing antigen binding molecule comprises one Fab domain capable of specific binding to PD-L1, meaning that it comprises monovalent binding towards PD-L1.

In a further aspect, provided is a 4-1BBL trimer-containing antigen binding molecule, wherein the antigen binding domain capable of specific binding to PD-L1 comprises a heavy chain variable region ($V_H$PD-L1) comprising (i) CDR-H1 comprising the amino acid sequence of SEQ ID NO:13, (ii) CDR-H2 comprising the amino acid sequence of SEQ ID NO:14, and (iii) CDR-H3 comprising the amino acid sequence of SEQ ID NO:15, and a light chain variable region ($V_L$PD-L1) comprising (iv) CDR-L1 comprising the amino acid sequence of SEQ ID NO:16, (v) CDR-L2 comprising the amino acid sequence of SEQ ID NO:17, and (vi) CDR-L3 comprising the amino acid sequence of SEQ ID NO:18.

In a further aspect, the 4-1BBL trimer-containing antigen binding molecule of the invention comprises a heavy chain variable region ($V_H$PD-L1) comprising an amino acid sequence that is at least about 95%, 96%, 97%, 98%, 99% or 100% identical to the amino acid sequence of SEQ ID NO:19, and a light chain variable region ($V_L$PD-L1) comprising an amino acid sequence that is at least about 95%, 96%, 97%, 98%, 99% or 100% identical to the amino acid sequence of SEQ ID NO:20. In one particular aspect, the 4-1BBL trimer-containing antigen binding molecule of the invention comprises a heavy chain variable region ($V_H$PD-L1) comprising an amino acid of SEQ ID NO:19, and a light chain variable region ($V_L$PD-L1) comprising an amino acid sequence of SEQ ID NO:20.

In a further aspect, provided is a 4-1BBL trimer-containing antigen binding molecule, wherein the antigen binding molecule comprises a first heavy chain and a first light chain, both comprising a Fab molecule capable of specific binding to PD-L1, a second heavy chain comprising the constant domains and two ectodomains of a 4-1BBL or a fragment thereof connected to each other by a first peptide linker fused at its C-terminus by a second peptide linker to a second heavy or light chain, and a second light chain comprising a constant domain and one ectodomain of 4-1BBL or a fragment thereof fused at its C-terminus by a third peptide linker to a second light or heavy chain, respectively. More particularly, provided is a 4-1BBL trimer-containing antigen binding molecule, wherein the first peptide comprising two ectodomains of 4-1BBL or a fragment thereof connected to each other by a first peptide linker is fused at its C-terminus by a second peptide linker to a CL domain that is part of a heavy chain, and the second peptide comprising one ectodomain of said 4-1BBL or a fragment thereof is fused at its C-terminus by a third peptide linker to a CH1 domain that is part of a light chain.

In a particular aspect, the invention relates to a 4-1BBL trimer-containing antigen binding molecule as defined above, wherein the peptide linker is $(G4S)_2$, i.e. a peptide linker of SEQ ID NO:36. In one aspect, the peptide linker in all instances is $(G4S)_2$.

Provided is further a 4-1BBL trimer-containing antigen binding molecule, wherein in the CL domain adjacent to 4-1BBL the amino acid at position 123 (EU numbering) has been replaced by arginine (R) and the amino acid at position 124 (EU numbering) has been substituted by lysine (K), and wherein in the CH1 domain adjacent to the 4-1BBL the amino acids at position 147 (EU numbering) and at position 213 (EU numbering) have been substituted by glutamic acid (E).

In another aspect, provided is a 4-1BBL trimer-containing antigen binding molecule, wherein the antigen binding molecule comprises (i) a first heavy chain comprising the VH domain comprising the amino acid sequence of SEQ ID NO:19 and a first light chain comprising the VL domain comprising the amino acid sequence of SEQ ID NO:20, (ii) a second heavy chain comprising the amino acid sequence selected from the group consisting of SEQ ID NO:21, SEQ ID NO:23, SEQ ID NO:25 and SEQ ID NO:27, and (iii) a second light chain comprising the amino acid sequence selected from the group consisting of SEQ ID NO:22, SEQ ID NO:24, SEQ ID NO:26 and SEQ ID NO:28.

In one particular aspect, provided is a 4-1BBL trimer-containing antigen binding molecule comprising a first heavy chain comprising an amino acid sequence that is at least about 95%, 96%, 97%, 98%, 99% or 100% identical to the amino acid sequence of SEQ ID NO:29, a first light chain comprising an amino acid sequence that is at least about 95%, 96%, 97%, 98%, 99% or 100% identical to the amino acid sequence of SEQ ID NO:30, a second heavy chain comprising an amino acid sequence that is at least about 95%, 96%, 97%, 98%, 99% or 100% identical to the amino acid sequence of SEQ ID NO:21 and a second light chain comprising an amino acid sequence that is at least about 95%, 96%, 97%, 98%, 99% or 100% identical to the amino acid sequence of SEQ ID NO:22. In a further particular aspect, provided is a 4-1BBL trimer-containing antigen binding molecule comprising a first heavy chain comprising an amino acid sequence of SEQ ID NO:29, a first light chain comprising an amino acid sequence of SEQ ID NO:30, a second heavy chain comprising an amino acid sequence of SEQ ID NO:21 and a second light chain comprising an amino acid sequence of SEQ ID NO:22.

According to another aspect of the invention, there is provided an isolated nucleic acid molecule encoding a 4-1BBL trimer-containing antigen binding molecule as defined herein before. The invention further provides a vector, particularly an expression vector, comprising the isolated nucleic acid molecule of the invention and a host cell comprising the isolated nucleic acid or the vector of the invention. In some embodiments the host cell is an eukaryotic cell, particularly a mammalian cell.

In another aspect, provided is a method for producing the 4-1BBL trimer-containing antigen binding molecule of the invention, comprising culturing the host cell of the invention under conditions suitable for expression of the 4-1BBL trimer-containing antigen binding molecule, and isolating the 4-1BBL trimer-containing antigen binding molecule. The invention also encompasses a 4-1BBL trimer-containing antigen binding molecule produced by the method of the invention.

The invention further provides a pharmaceutical composition comprising the 4-1BBL trimer-containing antigen binding molecule of the invention and at least one pharmaceutically acceptable excipient. In another aspect, a pharmaceutical composition is provided comprising the 4-1BBL trimer-containing antigen binding molecule of the invention and at least one pharmaceutically acceptable excipient, further comprising an additional therapeutic agent, e.g. a chemotherapeutic agent and/or other agents for use in cancer immunotherapy. In a further aspect, provided is a pharmaceutical composition further comprising a T-cell activating anti-CD3 bispecific antibody.

Also encompassed by the invention is the 4-1BBL trimer-containing antigen binding molecule of the invention, or the pharmaceutical composition of the invention, for use as a medicament. In one aspect is provided the 4-1BBL trimer-containing antigen binding molecule of the invention, or the pharmaceutical composition of the invention, for use in the treatment of a disease in an individual in need thereof. In a specific embodiment, provided is the 4-1BBL trimer-containing antigen binding molecule of the invention, or the pharmaceutical composition of the invention, for use in the treatment of cancer. In another aspect, provided is the 4-1BBL trimer-containing antigen binding molecule of the invention, or the pharmaceutical composition of the invention, for use in up-regulating or prolonging cytotoxic T cell activity. In another aspect, provided is the 4-1BBL trimer-containing antigen binding molecule of the invention, or the pharmaceutical composition of the invention, for use in the treatment of cancer, wherein the the 4-1BBL trimer-containing antigen binding molecule is used in combination with another therapeutic agent, e.g. a chemotherapeutic agent and/or other agents for use in cancer immunotherapy, or a T-cell activating anti-CD3 bispecific antibody. In one aspect, the other therapeutic agent is administered concurrently with, prior to, or subsequently to the 4-1BBL trimer-containing antigen binding molecule.

Also provided is the use of the 4-1BBL trimer-containing antigen binding molecule of the invention for the manufacture of a medicament for the treatment of a disease in an individual in need thereof, in particular for the manufacture of a medicament for the treatment of cancer, as well as a method of treating a disease in an individual, comprising administering to said individual a therapeutically effective amount of a composition comprising the 4-1BBL trimer-containing antigen binding molecule as disclosed herein in a pharmaceutically acceptable form. In a specific aspect, the disease is cancer. Further provided is the use of the 4-1BBL trimer-containing antigen binding molecule of the invention for the manufacture of a medicament for the treatment of cancer, wherein the 4-1BBL trimer-containing antigen binding molecule is used in combination with another therapeutic agent. Furthermore, provided is a method for treating an individual having cancer comprising administering to the subject an effective amount of the 4-1BBL trimer-containing antigen binding molecule of the invention. Also provided is a method of up-regulating or prolonging cytotoxic T cell activity in an individual having cancer, comprising administering to the individual an effective amount of the 4-1BBL trimer-containing antigen binding molecule of the invention, or the pharmaceutical composition of the invention. In any of the above embodiments the individual is preferably a mammal, particularly a human.

BRIEF DESCRIPTION OF THE DRAWINGS

FIG. 1A shows the dimeric 4-1BB ligand that is fused at the C-terminus to a human IgG1-CL domain with mutations E123R and Q124K (charged variant) and FIG. 1B shows the monomeric 4-1BB ligand fused at its C-terminus to a human IgG1-CH1 domain with mutations K147E and K213E (charged variant).

FIG. 3A shows the setup of the SPR experiments for simultaneous binding of the PD-L1 targeting split trimeric 4-1BB ligand-containing antigen binding molecules of the invention. The simultaneous binding of PD-L1-4-1BBL (Analyte 1) to immobilized human 4-1BB and human PD-L1-Fc (analyte 2) is shown in FIG. 3B.

DETAILED DESCRIPTION OF THE INVENTION

Definitions

Figure 1A:
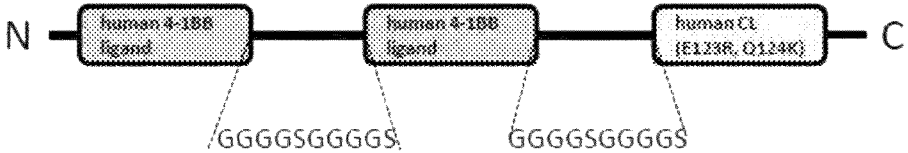
FIGS. 1A and 1B shows the components for the assembly of the monovalent PD-L1 targeting split trimeric 4-1BB ligand Fc fusion antigen binding molecules.

Unless defined otherwise, technical and scientific terms used herein have the same meaning as generally used in the art to which this invention belongs. For purposes of interpreting this specification, the following definitions will apply and whenever appropriate, terms used in the singular will also include the plural and vice versa.

As used herein, the term "antigen binding molecule" refers in its broadest sense to a molecule that specifically binds an antigenic determinant. Examples of antigen binding molecules are antibodies, antibody fragments and scaffold antigen binding proteins.

The term "antigen binding domain" refers to the part of an antigen binding molecule that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more variable domains (also called variable regions). Preferably, an antigen binding domain comprises an antibody light chain variable region (VL) and an antibody heavy chain variable region (VH).

As used herein, the term "antigen binding domain capable of specific binding to PD-L1" or "moiety capable of specific binding to PD-L1" refers to a polypeptide molecule that specifically binds to PD-L1. In one aspect, the antigen binding domain is able to inhibit signaling through PD-L1. In a particular aspect, the antigen binding domain is able to direct the entity to which it is attached (e.g. the 4-1BBL trimer) to a target site, for example to a specific type of T cell bearing PD-L1. Antigen binding domains capable of specific binding to PD-L1 include antibodies and fragments thereof as further defined herein. In relation to an antibody or fragment thereof, the term "moiety capable of specific binding to PD-L1" refers to the part of the molecule that comprises the area which specifically binds to and is complementary to part or all of an antigen. A moiety capable of specific antigen binding may be provided, for example, by one or more antibody variable domains (also called antibody variable regions). Particularly, a moiety capable of specific antigen binding comprises an antibody light chain variable region (VL) and an antibody heavy chain variable region (VH).

The term "antibody" herein is used in the broadest sense and encompasses various antibody structures, including but not limited to monoclonal antibodies, polyclonal antibodies, monospecific and multispecific antibodies (e.g., bispecific antibodies), and antibody fragments so long as they exhibit the desired antigen-binding activity.

The term "monoclonal antibody" as used herein refers to an antibody obtained from a population of substantially homogeneous antibodies, i.e., the individual antibodies comprising the population are identical and/or bind the same epitope, except for possible variant antibodies, e.g. containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen.

The term "monospecific" antibody as used herein denotes an antibody that has one or more binding sites each of which bind to the same epitope of the same antigen. The term "bispecific" means that the antigen binding molecule is able to specifically bind to at least two distinct antigenic determinants. Typically, a bispecific antigen binding molecule comprises two antigen binding sites, each of which is specific for a different antigenic determinant. In certain embodiments the bispecific antigen binding molecule is capable of simultaneously binding two antigenic determinants, particularly two antigenic determinants expressed on two distinct cells.

The term "valent" as used within the current application denotes the presence of a specified number of binding sites in an antigen binding molecule. As such, the terms "monovalent", "bivalent", "tetravalent", and "hexavalent" denote the presence of one binding site, two binding sites, four binding sites, and six binding sites, respectively, in an antigen binding molecule.

The terms "full length antibody", "intact antibody", and "whole antibody" are used herein interchangeably to refer to an antibody having a structure substantially similar to a native antibody structure. "Native antibodies" refer to naturally occurring immunoglobulin molecules with varying structures. For example, native IgG-class antibodies are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a light chain constant domain (CL), also called a light chain constant region. The heavy chain of an antibody may be assigned to one of five types, called α (IgA), δ (IgD), ε (IgE), γ (IgG), or μ (IgM), some of which may be further divided into subtypes, e.g. γ1 (IgG1), γ2 (IgG2), γ3 (IgG3), γ4 (IgG4), α1 (IgA1) and α2 (IgA2). The light chain of an antibody may be assigned to one of two types, called kappa (κ) and lambda (λ), based on the amino acid sequence of its constant domain.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies, triabodies, tetrabodies, cross-Fab fragments; linear antibodies; single-chain antibody molecules (e.g. scFv); and single domain antibodies. For a review of certain antibody fragments, see Hudson et al., Nat Med 9, 129-134 (2003). For a review of scFv fragments, see e.g. Pluckthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046. Diabodies are antibody fragments with two antigen-binding sites that may be bivalent or bispecific, see, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see e.g. U.S. Pat. No. 6,248,516 B1). Antibody fragments can be made by various techniques, including but not limited to proteolytic digestion of an intact antibody as well as production by recombinant host cells (e.g. *E. coli* or phage), as described herein.

Papain digestion of intact antibodies produces two identical antigen-binding fragments, called "Fab" fragments containing each the heavy- and light-chain variable domains and also the constant domain of the light chain and the first constant domain (CH1) of the heavy chain. As used herein, Thus, the term "Fab fragment" refers to an antibody fragment comprising a light chain fragment comprising a VL domain and a constant domain of a light chain (CL), and a VH domain and a first constant domain (CH1) of a heavy chain. Fab' fragments differ from Fab fragments by the addition of a few residues at the carboxy terminus of the heavy chain CH1 domain including one or more cysteins from the antibody hinge region. Fab'-SH are Fab' fragments in which the cysteine residue(s) of the constant domains bear a free thiol group. Pepsin treatment yields an $F(ab')_2$ fragment that has two antigen-combining sites (two Fab fragments) and a part of the Fc region.

The term "cross-Fab fragment" or "xFab fragment" or "crossover Fab fragment" refers to a Fab fragment, wherein either the variable regions or the constant regions of the heavy and light chain are exchanged. Two different chain compositions of a crossover Fab molecule are possible and comprised in the bispecific antibodies of the invention: On the one hand, the variable regions of the Fab heavy and light chain are exchanged, i.e. the crossover Fab molecule comprises a peptide chain composed of the light chain variable region (VL) and the heavy chain constant region (CH1), and a peptide chain composed of the heavy chain variable region (VH) and the light chain constant region (CL). This crossover Fab molecule is also referred to as $CrossFab_{(VLVH)}$. On the other hand, when the constant regions of the Fab heavy and light chain are exchanged, the crossover Fab molecule comprises a peptide chain composed of the heavy chain variable region (VH) and the light chain constant region (CL), and a peptide chain composed of the light chain variable region (VL) and the heavy chain constant region (CH1). This crossover Fab molecule is also referred to as $CrossFab_{(CLCH1)}$.

A "single chain Fab fragment" or "scFab" is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments are stabilized via the natural disulfide bond between the CL domain and the CH1 domain. In addition, these single chain Fab molecules might be further stabilized by generation of interchain disulfide bonds via insertion of cysteine residues (e.g. position 44 in the variable heavy chain and position 100 in the variable light chain according to Kabat numbering).

A "crossover single chain Fab fragment" or "x-scFab" is a is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CL-linker-VL-CH1 and b) VL-CH1-linker-VH-CL; wherein VH and VL form together an antigen-binding site which binds specifically to an antigen and wherein said linker is a polypeptide of at least 30 amino acids. In addition, these x-scFab molecules might be further stabilized by generation of interchain disulfide bonds via insertion of cysteine residues (e.g. position 44 in the variable heavy chain and position 100 in the variable light chain according to Kabat numbering).

A "single-chain variable fragment (scFv)" is a fusion protein of the variable regions of the heavy ($V_H$) and light chains ($V_L$) of an antibody, connected with a short linker peptide of ten to about 25 amino acids. The linker is usually rich in glycine for flexibility, as well as serine or threonine for solubility, and can either connect the N-terminus of the $V_H$ with the C-terminus of the $V_L$, or vice versa. This protein retains the specificity of the original antibody, despite removal of the constant regions and the introduction of the linker. scFv antibodies are, e.g. described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

An "antigen binding molecule that binds to the same epitope" as a reference molecule refers to an antigen binding molecule that blocks binding of the reference molecule to its antigen in a competition assay by 50% or more, and conversely, the reference molecule blocks binding of the antigen binding molecule to its antigen in a competition assay by 50% or more.

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins useful as antigens herein can be any native form the proteins from any vertebrate source, including mammals such as primates (e.g. humans) and rodents (e.g. mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g. splice variants or allelic variants.

The term "capable of specific binding to PD-L1" refers to an antigen binding molecule that is capable of binding to PD-L1 with sufficient affinity such that the antigen binding molecule is useful as a diagnostic and/or therapeutic agent in targeting PD-L1. The antigen binding molecule includes but is not limited to, antibodies, multispecific antibodies, Fab molecules, crossover Fab molecules, single chain Fab molecules, Fv molecules, scFv molecules, single domain antibodies, and fusion proteins. In one aspect, the extent of binding of an anti-PD-L1 antigen binding molecule to an unrelated, non-PD-L1 protein is less than about 10% of the binding of the antigen binding molecule to PD-L1 as measured, e.g., by surface plasmon resonance (SPR). In particular, an antigen binding molecule that is capable of specific binding to PD-L1 has a dissociation constant ($K_d$) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain aspects, an anti-PD-L1 antigen binding molecule binds to PD-L1 from different species. In particular, the anti-PD-L1 antigen binding molecule binds to human and cynomolgus PD-L1.

By "specific binding" is meant that the binding is selective for the antigen and can be discriminated from unwanted or non-specific interactions. The ability of an antigen binding molecule to bind to a specific antigen can be measured either through an enzyme-linked immunosorbent assay (ELISA) or other techniques familiar to one of skill in the art, e.g. Surface Plasmon Resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding molecule to an unrelated protein is less than about 10% of the binding of the antigen binding molecule to the antigen as measured, e.g. by SPR. In certain embodiments, an molecule that binds to the antigen has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g. from $10^{-9}$ M to $10^{-13}$ M).

"Affinity" or "binding affinity" refers to the strength of the sum total of non-covalent interactions between a single binding site of a molecule (e.g. an antibody) and its binding partner (e.g. an antigen). Unless indicated otherwise, as used herein, "binding affinity" refers to intrinsic binding affinity which reflects a 1:1 interaction between members of a binding pair (e.g. antibody and antigen). The affinity of a molecule X for its partner Y can generally be represented by the dissociation constant (Kd), which is the ratio of dissociation and association rate constants ($k_{off}$ and $k_{on}$, respectively). Thus, equivalent affinities may comprise different rate constants, as long as the ratio of the rate constants remains the same. Affinity can be measured by common methods known in the art, including those described herein. A particular method for measuring affinity is Surface Plasmon Resonance (SPR).

A "target cell antigen" as used herein refers to an antigenic determinant presented on the surface of a target cell, for example a T-cell or B-cell, a cell in a tumor such as a cancer cell or a cell of the tumor stroma. In certain aspects, the target cell antigen is an antigen on the surface of cancer cell. In one aspect, the target cell antigen is PD-L1.

The term "PD-L1", also known as CD274 or B7-H1, refers to any native PD-L1 from any vertebrate source, including mammals such as primates (e.g. humans) non-human primates (e.g. cynomolgus monkeys) and rodents (e.g. mice and rats), in particular to "human PD-L1". The amino acid sequence of complete human PD-L1 is shown in UniProt (www.uniprot.org) accession no. Q9NZQ7 (SEQ ID NO:37). The term "anti-PD-L1 antibody" or "antibody binding to human PD-L1" or "antibody that specifically binds to human PD-L1" or "antagonistic anti-PD-L1" refers to an antibody specifically binding to the human PD-L1 antigen with a binding affinity of KD-value of $1.0\times10^{-8}$ mol/l or lower, in one aspect of a KD-value of $1.0\times10^{-9}$ mol/l or lower. The binding affinity is determined with a standard binding assay, such as surface plasmon resonance technique (BIAcore®, GE-Healthcare Uppsala, Sweden).

A "T-cell antigen" as used herein refers to an antigenic determinant presented on the surface of a T lymphocyte, particularly a cytotoxic T lymphocyte.

A "T cell activating therapeutic agent" as used herein refers to a therapeutic agent capable of inducing T cell activation in a subject, particularly a therapeutic agent designed for inducing T-cell activation in a subject. Examples of T cell activating therapeutic agents include bispecific antibodies that specifically bind an activating T cell antigen, such as CD3, and a target cell antigen, such as CEA or Folate Receptor.

An "activating T cell antigen" as used herein refers to an antigenic determinant expressed by a T lymphocyte, particularly a cytotoxic T lymphocyte, which is capable of inducing or enhancing T cell activation upon interaction with an antigen binding molecule. Specifically, interaction of an antigen binding molecule with an activating T cell antigen may induce T cell activation by triggering the signaling cascade of the T cell receptor complex. An exemplary activating T cell antigen is CD3.

The term "CD3" refers to any native CD3 from any vertebrate source, including mammals such as primates (e.g. humans), non-human primates (e.g. cynomolgus monkeys) and rodents (e.g. mice and rats), unless otherwise indicated. The term encompasses "full-length," unprocessed CD3 as well as any form of CD3 that results from processing in the cell. The term also encompasses naturally occurring variants of CD3, e.g., splice variants or allelic variants. In one embodiment, CD3 is human CD3, particularly the epsilon subunit of human CD3 (CD3ε). The amino acid sequence of human CD3ε is shown in UniProt (www.uniprot.org) accession no. P07766 (version 144), or NCBI (www.ncbi.nlm.nih.gov/) RefSeq NP_000724.1. See also SEQ ID NO: 59. The amino acid sequence of cynomolgus [*Macaca fascicularis*] CD3ε is shown in UniProt (www.uniprot.org) accession no. Q95LI5. See also SEQ ID NO: 60.

The term "variable domain" or "variable region" refers to the domain of an antibody heavy or light chain that is involved in binding the antigen binding molecule to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6th ed., W. H. Freeman and Co., page 91 (2007). A single VH or VL domain may be sufficient to confer antigen-binding specificity.

The term "hypervariable region" or "HVR" as used herein refers to each of the regions of an antigen binding variable domain which are hypervariable in sequence and which determine antigen binding specificity, for example "complementarity determining regions" ("CDRs"). Generally, antigen binding domains comprise six CDRs: three in the VH (CDR-H1, CDR-H2, CDR-H3), and three in the VL (CDR-L1, CDR-L2, CDR-L3). Exemplary CDRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));
(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest,* 5th Ed. Public Health Service, National Institutes of Health, Bethesda, MD (1991)); and
(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)).

Unless otherwise indicated, the CDRs are determined according to Kabat et al., supra. One of skill in the art will understand that the CDR designations can also be determined according to Chothia, supra, McCallum, supra, or any other scientifically accepted nomenclature. Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

As used herein, the term "affinity matured" in the context of antigen binding molecules (e.g., antibodies) refers to an antigen binding molecule that is derived from a reference antigen binding molecule, e.g., by mutation, binds to the same antigen, preferably binds to the same epitope, as the reference antibody; and has a higher affinity for the antigen than that of the reference antigen binding molecule. Affinity maturation generally involves modification of one or more amino acid residues in one or more CDRs of the antigen binding molecule. Typically, the affinity matured antigen binding molecule binds to the same epitope as the initial reference antigen binding molecule.

"Framework" or "FR" refers to variable domain residues other than hypervariable region (HVR) residues. The FR of a variable domain generally consists of four FR domains: FR1. FR2, FR3, and FR4. Accordingly, the HVR and FR sequences generally appear in the following sequence in VH (or VL): FR1-H1(L1)-FR2-H2(L2)-FR3-H3(L3)-FR4.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g. $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ respectively.

The terms "constant region derived from human origin" or "human constant region" denote a constant heavy chain region of a human antibody of the subclass IgG1, IgG2, IgG3, or IgG4 and/or a constant light chain kappa or lambda region. Such constant regions are well known in the state of the art and e.g. described by Kabat, E. A., et al., Sequences of Proteins of Immunological Interest, 5th ed., Public Health Service, National Institutes of Health, Bethesda, MD (1991) (see also e.g. Johnson, G., and Wu, T. T., Nucleic Acids Res.

28 (2000) 214-218; Kabat, E. A., et al., Proc. Natl. Acad. Sci. USA 72 (1975) 2785-2788). Unless otherwise specified herein, numbering of amino acid residues in the constant region is according to the EU numbering system, also called the EU index of Kabat, as described in Kabat, E. A. et al., Sequences of Proteins of Immunological Interest, 5th ed., Public Health Service, National Institutes of Health, Bethesda, MD (1991), NIH Publication 91-3242.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

A "human" antibody is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "Fc domain" or "Fc region" herein is used to define a C-terminal region of an antibody heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, antibodies produced by host cells may undergo post-translational cleavage of one or more, particularly one or two, amino acids from the C-terminus of the heavy chain. Therefore an antibody produced by a host cell by expression of a specific nucleic acid molecule encoding a full-length heavy chain may include the full-length heavy chain, or it may include a cleaved variant of the full-length heavy chain. This may be the case where the final two C-terminal amino acids of the heavy chain are glycine (G446) and lysine (K447, numbering according to Kabat EU index). Therefore, the C-terminal lysine (Lys447), or the C-terminal glycine (Gly446) and lysine (Lys447), of the Fc region may or may not be present. Amino acid sequences of heavy chains including an Fc region are denoted herein without C-terminal glycine-lysine dipeptide if not indicated otherwise. In one embodiment, a heavy chain including an Fc region as specified herein, comprised in an antibody according to the invention, comprises an additional C-terminal glycine-lysine dipeptide (G446 and K447, numbering according to EU index of Kabat). In one embodiment, a heavy chain including an Fc region as specified herein, comprised in an antibody according to the invention, comprises an additional C-terminal glycine residue (G446, numbering according to EU index of Kabat). Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, MD, 1991. An IgG Fc region comprises an IgG CH2 and an IgG CH3 domain. The "CH2 domain" of a human IgG Fc region usually extends from an amino acid residue at about position 231 to an amino acid residue at about position 340. In one embodiment, a carbohydrate chain is attached to the CH2 domain. The CH2 domain herein may be a native sequence CH2 domain or variant CH2 domain. The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a variant CH3 domain (e.g. a CH3 domain with an introduced "protuberance" ("knob") in one chain thereof and a corresponding introduced "cavity" ("hole") in the other chain thereof; see U.S. Pat. No. 5,821,333, expressly incorporated herein by reference). Such variant CH3 domains may be used to promote heterodimerization of two non-identical antibody heavy chains as herein described.

The "knob-into-hole" technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine). The protuberance and cavity can be made by altering the nucleic acid encoding the polypeptides, e.g. by site-specific mutagenesis, or by peptide synthesis. In a specific embodiment a knob modification comprises the amino acid substitution T366W in one of the two subunits of the Fc domain, and the hole modification comprises the amino acid substitutions T366S, L368A and Y407V in the other one of the two subunits of the Fc domain. In a further specific embodiment, the subunit of the Fc domain comprising the knob modification additionally comprises the amino acid substitution S354C, and the subunit of the Fc domain comprising the hole modification additionally comprises the amino acid substitution Y349C. Introduction of these two cysteine residues results in the formation of a disulfide bridge between the two subunits of the Fc region, thus further stabilizing the dimer (Carter, J Immunol Methods 248, 7-15 (2001)). The numbering is according to EU index of Kabat et al, Sequences of Proteins of Immunological Interest, 5th Ed. Public Health Service, National Institutes of Health, Bethesda, MD, 1991.

A "region equivalent to the Fc region of an immunoglobulin" is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody-dependent cellular cytotoxicity). For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, J. U. et al., Science 247:1306-10 (1990)).

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

An "activating Fc receptor" is an Fc receptor that following engagement by an Fc region of an antibody elicits signaling events that stimulate the receptor-bearing cell to perform effector functions. Activating Fc receptors include FcγRIIIa (CD16a), FcγRI (CD64), FcγRIIa (CD32), and FcαRI (CD89). A particular activating Fc receptor is human FcγRIIIa (see UniProt accession no. P08637, version 141).

The term "TNF ligand family member" or "TNF family ligand" refers to a proinflammatory cytokine. Cytokines in general, and in particular the members of the TNF ligand family, play a crucial role in the stimulation and coordination of the immune system. At present, nineteen cytokines have been identified as members of the TNF (tumour necrosis factor) ligand superfamily on the basis of sequence, functional, and structural similarities. All these ligands are type II transmembrane proteins with a C-terminal extracellular domain (ectodomain), N-terminal intracellular domain and a single transmembrane domain. The C-terminal extracellular domain, known as TNF homology domain (THD), has 20-30% amino acid identity between the superfamily members and is responsible for binding to the receptor. The TNF ectodomain is also responsible for the TNF ligands to form trimeric complexes that are recognized by their specific receptors. Members of the TNF ligand family are selected from the group consisting of Lymphotoxin α (also known as LTA or TNFSF1), TNF (also known as TNFSF2), LTβ (also known as TNFSF3), OX40L (also known as TNFSF4), CD40L (also known as CD154 or TNFSF5), FasL (also known as CD95L, CD178 or TNFSF6), CD27L (also known as CD70 or TNFSF7), CD30L (also known as CD153 or TNFSF8), 4-1BBL (also known as TNFSF9), TRAIL (also known as APO2L, CD253 or TNFSF10), RANKL (also known as CD254 or TNFSF11), TWEAK (also known as TNFSF12), APRIL (also known as CD256 or TNFSF13), BAFF (also known as CD257 or TNFSF13B), LIGHT (also known as CD258 or TNFSF14), TLIA (also known as VEGI or TNFSF15), GITRL (also known as TNFSF18), EDA-A1 (also known as ectodysplasin A1) and EDA-A2 (also known as ectodysplasin A2). The term refers to any native TNF family ligand from any vertebrate source, including mammals such as primates (e.g. humans), non-human primates (e.g. cynomolgus monkeys) and rodents (e.g. mice and rats), unless otherwise indicated. The term "costimulatory TNF ligand family member" or "costimulatory TNF family ligand" refers to a subgroup of TNF ligand family members, which are able to costimulate proliferation and cytokine production of T-cells. These TNF family ligands can costimulate TCR signals upon interaction with their corresponding TNF receptors and the interaction with their receptors leads to recruitment of TNFR-associated factors (TRAF), which initiate signalling cascades that result in T-cell activation. Costimulatory TNF family ligands are selected from the group consisting of 4-1BBL, OX40L, GITRL, CD70, CD30L and LIGHT, more particularly the costimulatory TNF ligand family member is 4-1BBL.

As described herein before, 4-1BBL is a type II transmembrane protein and one member of the TNF ligand family. Complete or full length 4-1BBL having the amino acid sequence of SEQ ID NO:38 has been described to form trimers on the surface of cells. The formation of trimers is enabled by specific motives of the ectodomain of 4-1BBL. Said motives are designated herein as "trimerization region". The amino acids 50-254 of the human 4-1BBL sequence (SEQ ID NO:39) form the extracellular domain of 4-1BBL, but even fragments thereof are able to form the trimers. In specific embodiments of the invention, the term "ectodomain of 4-1BBL or a fragment thereof" refers to a polypeptide having an amino acid sequence selected from SEQ ID NO:4 (amino acids 52-254 of human 4-1BBL), SEQ ID NO:1 (amino acids 71-254 of human 4-1BBL), SEQ ID NO:3 (amino acids 80-254 of human 4-1BBL) and SEQ ID NO:2 (amino acids 85-254 of human 4-1BBL) or a polypeptide having an amino acid sequence selected from SEQ ID NO:5 (amino acids 71-248 of human 4-1BBL), SEQ ID NO:8 (amino acids 52-248 of human 4-1BBL), SEQ ID NO:7 (amino acids 80-248 of human 4-1BBL) and SEQ ID NO:6 (amino acids 85-248 of human 4-1BBL), but also other fragments of the ectodomain capable of trimerization are included herein.

An "ectodomain" is the domain of a membrane protein that extends into the extracellular space (i.e. the space outside the target cell). Ectodomains are usually the parts of proteins that initiate contact with surfaces, which leads to signal transduction. The ectodomain of TNF ligand family member as defined herein thus refers to the part of the TNF ligand protein that extends into the extracellular space (the extracellular domain), but also includes shorter parts or fragments thereof that are responsible for the trimerization and for the binding to the corresponding TNF receptor. The term "ectodomain of a TNF ligand family member or a fragment thereof" thus refers to the extracellular domain of the TNF ligand family member that forms the extracellular domain or to parts thereof that are still able to bind to the receptor (receptor binding domain).

The term "peptide linker" refers to a peptide comprising one or more amino acids, typically about 2 to 20 amino acids. Peptide linkers are known in the art or are described herein. Suitable, non-immunogenic linker peptides are, for example, $(G_4S)_n$, $(SG_4)_n$ or $G_4(SG_4)_n$ peptide linkers, wherein "n" is generally a number between 1 and 10, typically between 1 and 4, in particular 2, i.e. the peptides selected from the group consisting of GGGGS (SEQ ID NO:40), GGGGSGGGGS (SEQ ID NO:36), SGGGGSGGGG (SEQ ID NO:41), $(G_4S)_3$ or GGGGSGGGGSGGGGS (SEQ ID NO:42), GGGGSGGGGSGGGG or $G4(SG4)_2$ (SEQ ID NO:43), and $(G_4S)_4$ or GGGGSGGGGSGGGGSGGGGS (SEQ ID NO:44), but also include the sequences GSPGSSSSGS (SEQ ID NO:45), GSGSGSGS (SEQ ID NO:46), GSGSGNGS (SEQ ID NO:47), GGSGSGSG (SEQ ID NO:48), GGSGSG (SEQ ID NO:49), GGSG (SEQ ID NO:50), GGSGNGSG (SEQ ID NO:51), GGNGSGSG (SEQ ID NO:52) and GGNGSG (SEQ ID NO:53). Peptide linkers of particular interest are $(G4S)_1$ or GGGGS (SEQ ID NO:40), $(G_4S)_2$ or GGGGSGGGGS (SEQ ID NO:36), $(G_4S)_3$ (SEQ ID NO:42) and $(G_4S)_4$ (SEQ ID NO:44).

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

A "fusion polypeptide" or "fusion protein" as used herein refers to a single chain polypeptide composed of an antibody fragment and a peptide that is not derived from an antibody. In one aspect, a fusion polypeptide is composed of one or two ectodomains of 4-1BBL or a fragment thereof fused to a part of antigen binding domain or Fc part. The fusion may occur by directly linking the N or C-terminal amino acid of the antigen binding moiety via a peptide linker to the C- or N-terminal amino acid of the ectodomain of said 4-1BBL or fragment thereof.

By "fused" or "connected" is meant that the components (e.g. a polypeptide and an ectodomain of said TNF ligand family member) are linked by peptide bonds, either directly or via one or more peptide linkers.

"Percent (%) amino acid sequence identity" with respect to a reference polypeptide (protein) sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN. SAWI or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction $X/Y$ where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

In certain embodiments, amino acid sequence variants of the TNF ligand trimer-containing antigen binding molecules provided herein are contemplated. For example, it may be desirable to improve the binding affinity and/or other biological properties of the TNF ligand trimer-containing antigen binding molecules. Amino acid sequence variants of the TNF ligand trimer-containing antigen binding molecules may be prepared by introducing appropriate modifications into the nucleotide sequence encoding the molecules, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding. Sites of interest for substitutional mutagenesis include the HVRs and Framework (FRs). Conservative substitutions are provided in Table B under the heading "Preferred Substitutions" and further described below in reference to amino acid side chain classes (1) to (6). Amino acid substitutions may be introduced into the molecule of interest and the products screened for a desired activity, e.g., retained/improved antigen binding, decreased immunogenicity, or improved ADCC or CDC.

TABLE A

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gin;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The term "amino acid sequence variants" includes substantial variants wherein there are amino acid substitutions in one or more hypervariable region residues of a parent antigen binding molecule (e.g. a humanized or human antibody). Generally, the resulting variant(s) selected for further study will have modifications (e.g., improvements) in certain biological properties (e.g., increased affinity, reduced immunogenicity) relative to the parent antigen binding molecule and/or will have substantially retained certain biological properties of the parent antigen binding molecule. An exemplary substitutional variant is an affinity matured antibody, which may be conveniently generated, e.g., using phage display-based affinity maturation techniques such as those described herein. Briefly, one or more CDR residues are mutated and the variant antigen binding molecules displayed on phage and screened for a particular biological activity (e.g. binding affinity). In certain embodiments, substitutions, insertions, or deletions may occur within one or more CDRs so long as such alterations do not substantially reduce the ability of the antigen binding molecule to bind antigen. For example, conservative alterations (e.g., conservative substitutions as provided herein) that do not substantially reduce binding affinity may be made in CDRs. A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antigen binding molecule complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include a 4-1BBL trimer-containing antigen binding molecule with an N-terminal methionyl residue. Other insertional variants of the molecule include the fusion to the N- or C-terminus to a polypeptide which increases the serum half-life of the 4-1BBL trimer-containing antigen binding molecule.

In certain embodiments, the 4-1BBL trimer-containing antigen binding molecules provided herein are altered to increase or decrease the extent to which the antibody is glycosylated. Glycosylation variants of the molecules may be conveniently obtained by altering the amino acid sequence such that one or more glycosylation sites is created or removed. Where the 4-1BBL trimer-containing antigen binding molecule comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in 4-1BBL ligand trimer-containing antigen binding molecule may be made in order to create variants with certain improved properties. In one aspect, variants of 4-1BBL trimer-containing antigen binding molecules are provided having a carbohydrate structure that lacks fucose attached (directly or indirectly) to an Fc region. Such fucosylation variants may have improved ADCC function, see e.g. US Patent Publication Nos. US 2003/0157108 (Presta, L.) or US 2004/0093621 (Kyowa Hakko Kogyo Co., Ltd). Further variants of the 4-1BBL trimer-containing antigen binding molecules of the invention include those with bisected oligosaccharides, e.g., in which a biantennary oligosaccharide attached to the Fc region is bisected by GlcNAc. Such variants may have reduced fucosylation and/or improved ADCC function, see for example WO 2003/011878 (Jean-Mairet et al.); U.S. Pat. No. 6,602,684 (Umana et al.); and US 2005/0123546 (Umana et al.). Variants with at least one galactose residue in the oligosaccharide attached to the Fc region are also provided. Such antibody variants may have improved CDC function and are described, e.g., in WO 1997/30087 (Patel et al.); WO 1998/58964 (Raju, S.); and WO 1999/22764 (Raju, S.).

In certain embodiments, it may be desirable to create cysteine engineered variants of the 4-1BBL trimer-containing antigen binding molecule of the invention, e.g., "thioMAbs," in which one or more residues of the molecule are substituted with cysteine residues. In particular embodiments, the substituted residues occur at accessible sites of the molecule. By substituting those residues with cysteine, reactive thiol groups are thereby positioned at accessible sites of the antibody and may be used to conjugate the antibody to other moieties, such as drug moieties or linker-drug moieties, to create an immunoconjugate. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antigen binding molecules may be generated as described, e.g., in U.S. Pat. No. 7,521,541.

In certain aspects, the 4-1BBL trimer-containing antigen binding molecules provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the bispecific antibody derivative will be used in a therapy under defined conditions, etc. In another aspect, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605).

The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

In another aspect, immunoconjugates of the 4-1BBL trimer-containing antigen binding molecules provided herein maybe obtained. An "immunoconjugate" is an antibody conjugated to one or more heterologous molecule(s), including but not limited to a cytotoxic agent.

The term "nucleic add molecule" or "polynucleotide" includes any compound and/or substance that comprises a polymer of nucleotides. Each nucleotide is composed of a base, specifically a purine- or pyrimidine base (i.e. cytosine (C), guanine (G), adenine (A), thymine (T) or uracil (U)), a sugar (i.e. deoxyribose or ribose), and a phosphate group. Often, the nucleic acid molecule is described by the sequence of bases, whereby said bases represent the primary structure (linear structure) of a nucleic acid molecule. The sequence of bases is typically represented from 5' to 3'. Herein, the term nucleic acid molecule encompasses deoxyribonucleic acid (DNA) including e.g., complementary DNA (cDNA) and genomic DNA, ribonucleic acid (RNA), in particular messenger RNA (mRNA), synthetic forms of DNA or RNA, and mixed polymers comprising two or more of these molecules. The nucleic acid molecule may be linear or circular. In addition, the term nucleic acid molecule includes both, sense and antisense strands, as well as single stranded and double stranded forms. Moreover, the herein described nucleic acid molecule can contain naturally occurring or non-naturally occurring nucleotides. Examples of non-naturally occurring nucleotides include modified nucleotide bases with derivatized sugars or phosphate backbone linkages or chemically modified residues. Nucleic acid molecules also encompass DNA and RNA molecules which are suitable as a vector for direct expression of an antibody of the invention in vitro and/or in vivo, e.g., in a host or patient. Such DNA (e.g., cDNA) or RNA (e.g., mRNA) vectors, can be unmodified or modified. For example, mRNA can be chemically modified to enhance the stability of the RNA vector and/or expression of the encoded molecule so that mRNA can be injected into a subject to generate the antibody in vivo (see e.g., Stadler et al, Nature Medicine 2017, published online 12 Jun. 2017, doi:10.1038/nm.4356 or EP 2 101 823 B1).

By "Isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode bispecific antigen binding molecules of the invention or fragments thereof.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the bispecific antigen binding molecules of the present invention. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "Individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable excipient" refers to an ingredient in a pharmaceutical composition, other than an active ingredient, which is nontoxic to a subject. A pharmaceutically acceptable excipient includes, but is not limited to, a buffer, a stabilizer, or a preservative.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, the molecules of the invention are used to delay development of a disease or to slow the progression of a disease.

The term "cancer" as used herein refers to proliferative diseases, such as lymphomas, carcinoma, lymphoma, blastoma, sarcoma, leukemia, lymphocytic leukemias, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colorectal cancer (CRC), pancreatic cancer, breast cancer, triple-negative breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, melanoma, multiple myeloma, B-cell cancer (lymphoma), chronic lymphocytic leukemia (CLL), acute lymphoblastic leukemia (ALL), hairy cell leukemia, chronic myeloblastic leukemia, including refractory versions of any of the above cancers, or a combination of one or more of the above cancers.

An "advanced" cancer is one which has spread outside the site or organ of origin, either by local invasion or metastasis. Accordingly, the term "advanced" cancer includes both locally advanced and metastatic disease.

A "recurrent" cancer is one which has regrown, either at the initial site or at a distant site, after a response to initial therapy, such as surgery. A "locally recurrent" cancer is cancer that returns after treatment in the same place as a previously treated cancer. An "operable" or "resectable" cancer is cancer which is confined to the primary organ and suitable for surgery (resection). A "non-resectable" or "unresectable" cancer is not able to be removed (resected) by surgery.

4-1BBL Trimer-Containing Antigen Binding Molecules of the Invention

The invention provides novel 4-1BBL trimer-containing antigen binding molecules with particularly advantageous properties such as producibility, stability, binding affinity, biological activity, targeting efficiency, reduced toxicity and reduced immunicity.

In a first aspect, the invention provides a 4-1BBL trimer-containing antigen binding molecule comprising (a) an antigen binding domain capable of specific binding to PD-L1, (b) a first and a second polypeptide that are linked to each other by a disulfide bond, wherein the antigen binding molecule is characterized in that the first polypeptide comprises two ectodomains of 4-1BBL or a fragment thereof that are connected to each other by a peptide linker and in that the second polypeptide comprises one ectodomain of 4-1BBL or a fragment thereof, and (c) an Fc domain composed of a first and a second subunit capable of stable association.

In a further aspect, provided is a 4-1BBL trimer-containing antigen binding molecule as defined herein before, comprising (a) an antigen binding domain capable of specific binding to PD-L1, and (b) a first and a second polypeptide that are linked to each other by a disulfide bond, wherein the antigen binding molecule is characterized in that (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or a fragment thereof that are connected to each other and to the CH1 or CL domain by a peptide linker and wherein the second polypeptide comprises one ectodomain of said 4-1BBL or a fragment thereof connected via a peptide linker to the CL or CH1 domain of said polypeptide, or (ii) the first polypeptide contains a CH3 domain and the second polypeptide contains a CH3 domain, respectively, and wherein the first polypeptide comprises two ectodomains of a 4-1BBL or a fragment thereof that are connected to each other and to the C-terminus of the CH3 domain by a peptide linker and wherein the second polypeptide comprises only one ectodomain of said 4-1BBL or a fragment thereof connected via a peptide linker to C-terminus of the CH3 domain of said polypeptide, or (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL or a fragment thereof that are connected to each other and to to VH or VL by a peptide linker and wherein the second polypeptide comprises one ectodomain of said TNF ligand family member or a fragment thereof connected via a peptide linker to VL or VH of said polypeptide, and (c) an Fc domain composed of a first and a second subunit capable of stable association.

In another aspect, provided is a 4-1BBL trimer-containing antigen binding molecule of as defined herein before, comprising (a) an antigen binding domain capable of specific binding to PD-L1, and (b) a first and a second polypeptide that are linked to each other by a disulfide bond, wherein the antigen binding molecule is characterized in that (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL or a fragment thereof that are connected to each other and to the CH1 or CL domain by a peptide linker and wherein the second polypeptide comprises one ectodomain of said 4-1BBL or a fragment thereof connected via a peptide linker to the CL or CH1 domain of said polypeptide, or (ii) the first polypeptide contains a CH3 domain and the second polypeptide contains a CH3 domain, respectively, and wherein the first polypeptide comprises two ectodomains of 4-1BBL or a fragment thereof that are connected to each other and to the C-terminus of the CH3 domain by a peptide linker and wherein the second polypeptide comprises only one ectodomain of said 4-1BBL or a fragment thereof connected via a peptide linker to C-terminus of the CH3 domain of said polypeptide, and (c) an Fc domain composed of a first and a second subunit capable of stable association.

In one aspect, the ectodomain of 4-1BBL comprises the amino acid sequence selected from the group consisting of SEQ ID NO:1, SEQ ID NO: 2, SEQ ID NO:3, SEQ ID NO:4, SEQ ID NO:5, SEQ ID NO: 6, SEQ ID NO:7 and SEQ ID NO:8, particularly the amino acid sequence of SEQ ID NO:1 or SEQ ID NO:5. More particularly, the ectodomain of 4-1BBL comprises the amino acid sequence of SEQ ID NO:1 or SEQ ID NO:5. Most particularly, the ectodomain of 4-1BBL comprises the amino acid sequence of SEQ ID NO:5. In particular, provided is a 4-1BBL trimer-containing antigen binding molecule of as defined herein before, wherein all three ectodomains of 4-1BBL or a fragment thereof are identical.

Thus, provided is a 4-1BBL trimer-containing antigen binding molecule comprising (a) at least one Fab molecule capable of specific binding to PD-L1, (b) a first and a second polypeptide that are linked to each other by a disulfide bond, wherein the antigen binding molecule is characterized in that (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of 4-1BBL comprising the amino acid sequence selected from the group consisting of SEQ ID NO:1, SEQ ID NO: 2, SEQ ID NO:3, SEQ ID NO:4, SEQ ID NO:5, SEQ ID NO:6, SEQ ID NO:7 and SEQ ID NO:8 that are connected to each other and to the CH1 or CL domain by a peptide linker and wherein the second polypeptide comprises one ectodomain of said 4-1BBL comprising the amino acid sequence selected from the group consisting of SEQ ID NO:1, SEQ ID NO: 2, SEQ ID NO:3, SEQ ID NO:4, SEQ ID NO:5, SEQ ID NO:6, SEQ ID NO:7 and SEQ ID NO:8 connected via a peptide linker to the CL or CH1 domain of said polypeptide, or (ii) the first polypeptide contains a CH3 domain and the second polypeptide contains a CH3 domain, respectively, and wherein the first polypeptide comprises two ectodomains of 4-1BBL comprising the amino acid sequence selected from the group consisting of SEQ ID NO:1, SEQ ID NO: 2, SEQ ID NO:3, SEQ ID NO:4, SEQ ID NO:5, SEQ ID NO:6, SEQ ID NO:7 and SEQ ID NO:8 that are connected to each other and to the C-terminus of the CH3 domain by a peptide linker and wherein the second polypeptide comprises only one ectodomain of said 4-1BBL comprising the amino acid sequence selected from the group consisting of SEQ ID NO:1, SEQ ID NO: 2, SEQ ID NO:3, SEQ ID NO:4, SEQ ID NO:5, SEQ ID NO:6, SEQ ID NO:7 and SEQ ID NO:8 connected via a peptide linker to C-terminus of the CH3 domain of said polypeptide, or (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of 4-1BBL comprising the amino acid sequence selected from the group consisting of SEQ ID NO:1, SEQ ID NO: 2, SEQ ID NO:3, SEQ ID NO:4, SEQ ID NO:5, SEQ ID NO: 6, SEQ ID NO:7 and SEQ ID NO:8 that are connected to each other and to VH or VL by a peptide linker and wherein the second polypeptide comprises one ectodomain of said 4-1BBL comprising the amino acid sequence selected from the group consisting of SEQ ID NO:1, SEQ ID NO: 2, SEQ ID NO:3, SEQ ID NO:4, SEQ ID NO:5, SEQ ID NO: 6, SEQ ID NO:7 and SEQ ID NO:8 connected via a peptide linker to VL or VH of said polypeptide, and (c) an Fc domain composed of a first and a second subunit capable of stable association.

In a further aspect, the 4-1BBL trimer-containing antigen binding molecule of the invention comprises (a) an antigen binding domain capable of specific binding to PD-L1, (b) a first and a second polypeptide that are linked to each other by a disulfide bond, wherein the antigen binding molecule is characterized in that the first polypeptide comprises the amino acid sequence selected from the group consisting of SEQ ID NO:9, SEQ ID NO:10, SEQ ID NO:11 and SEQ ID NO:12 and in that the second polypeptide comprises the amino acid sequence selected from the group consisting of SEQ ID NO:1, SEQ ID NO:5, SEQ ID NO:3 and SEQ ID NO:4, and (c) an Fc domain composed of a first and a second subunit capable of stable association.

In one aspect, the 4-1BBL trimer-containing antigen binding molecule of the invention comprises (a) an antigen binding domain capable of specific binding to PD-L1, (b) a first and a second polypeptide that are linked to each other by a disulfide bond, wherein the antigen binding molecule is characterized in that the first polypeptide comprises the amino acid sequence of SEQ ID NO:10 and in that the second polypeptide comprises the amino acid sequence of SEQ ID NO:5, and (c) an Fc domain composed of a first and a second subunit capable of stable association.

In a further aspect, the 4-1BBL trimer-containing antigen binding molecule of the invention comprises (a) an antigen binding domain capable of specific binding to PD-L1, (b) a first and a second polypeptide that are linked to each other by a disulfide bond, wherein the antigen binding molecule is characterized in that the first polypeptide comprises the amino acid sequence of SEQ ID NO:9 and in that the second polypeptide comprises the amino acid sequence of SEQ ID NO:1, and (c) an Fc domain composed of a first and a second subunit capable of stable association.

In another aspect, the 4-1BBL trimer-containing antigen binding molecule of the invention comprises (a) an antigen binding domain capable of specific binding to PD-L1, (b) a first polypeptide containing a CH1 or CL domain and a second polypeptide containing a CL or CH1 domain, respectively, wherein the second polypeptide is linked to the first polypeptide by a disulfide bond between the CH1 and CL domain, and wherein the antigen binding molecule is characterized in that the first polypeptide comprises two ectodomains of 4-1BBL or fragments thereof that are connected to each other and to the CH1 or CL domain by a peptide linker and in that the second polypeptide comprises only one ectodomain of 4-1BBL or a fragment thereof connected by a peptide linker to the CL or CH1 domain of said polypeptide.

In one aspect, provided is a 4-1BBL trimer-containing antigen binding molecule comprising (a) an antigen binding domain capable of specific binding to PD-L1, (b) a first polypeptide containing a CH1 domain and a second polypeptide containing a CL domain, wherein the second polypeptide is linked to the first polypeptide by a disulfide bond between the CH1 and CL domain, and wherein the antigen binding molecule is characterized in that the first polypeptide comprises two ectodomains of 4-1BBL or a fragment thereof that are connected to each other and to the CH1 domain by a peptide linker and in that the second polypeptide comprises one ectodomain of 4-1BBL or a fragment thereof connected via a peptide linker to the CL domain of said polypeptide.

In another aspect, the invention provides a 4-1BBL trimer-containing antigen binding molecule comprising (a) one antigen binding domain capable of specific binding to PD-L1, and (b) a first and a second polypeptide that are linked to each other by a disulfide bond, wherein the antigen binding molecule is characterized in that the first polypeptide comprises two ectodomains of 4-1BBL or a fragment thereof that are connected to each other by a peptide linker and in that the second polypeptide comprises one ectodomain of 4-1BBL or a fragment thereof, and (c) an Fc domain composed of a first and a second subunit capable of stable association.

In yet another aspect, the invention provides a 4-1BBL trimer-containing antigen binding molecule comprising (a) more than one antigen binding domain capable of specific binding to PD-L1, and (b) a first and a second polypeptide that are linked to each other by a disulfide bond, wherein the antigen binding molecule is characterized in that the first polypeptide comprises two ectodomains of 4-1BBL or a fragment thereof that are connected to each other by a peptide linker and in that the second polypeptide comprises one ectodomain of 4-1BBL or a fragment thereof, and (c) an Fc domain composed of a first and a second subunit capable of stable association.

In one aspect, the invention provides a 4-1BBL trimer-containing antigen binding molecule comprising (a) two antigen binding domains capable of specific binding to PD-L1, and (b) a first and a second polypeptide that are linked to each other by a disulfide bond, wherein the antigen binding molecule is characterized in that the first polypeptide comprises two ectodomains of 4-1BBL or a fragment thereof that are connected to each other by a peptide linker and in that the second polypeptide comprises one ectodomain of 4-1BBL or a fragment thereof, and (c) an Fc domain composed of a first and a second subunit capable of stable association.

In a further aspect, the invention provides a 4-1BBL trimer-containing antigen binding molecule as defined herein before, wherein antigen binding domain capable of specific binding to PD-L1 is selected from the group consisting of an antibody or an antibody fragment.

In one aspect, provided is a 4-1BBL trimer-containing antigen binding molecule as described herein before, wherein the antigen binding domain capable of specific binding to PD-L1 is selected from the group consisting of an antibody fragment, a Fab molecule, a crossover Fab molecule, a single chain Fab molecule, a Fv molecule, a scFv molecule, a single domain antibody, or a VH. In one aspect, the antigen binding domain capable of specific binding to PD-L1 a VH and VL domain.

In a particular aspect, provided is a 4-1BBL trimer-containing antigen binding molecule, wherein the antigen binding domain capable of specific binding to PD-L1 is a Fab molecule or a crossover Fab molecule capable of specific binding to PD-L1. In particular, the antigen binding domain capable of specific binding to PD-L1 is a Fab capable of specific binding to PD-L1.

In a further aspect, provided is a 4-1BBL trimer-containing antigen binding molecule according to the invention, wherein a peptide comprising two ectodomains of 4-1BBL or a fragment thereof connected to each other by a first peptide linker is fused at its C-terminus to the CH1 domain of a heavy chain by a second peptide linker and wherein one ectodomain of said 4-1BBL or a fragment thereof is fused at the its C-terminus to the CL domain on a light chain by a third peptide linker.

In another aspect, provided is a 4-1BBL trimer-containing antigen binding molecule according to the invention, wherein a peptide comprising two ectodomains of 4-1BBL or a fragment thereof connected to each other by a first peptide linker is fused at its C-terminus to the CL domain of a heavy chain by a second peptide linker and wherein one ectodomain of said 4-1BBL or a fragment thereof is fused at the its C-terminus to the CH1 domain on a light chain by a third peptide linker.

In a further aspect, the invention is concerned with a 4-1BBL trimer-containing antigen binding molecule according to the invention, wherein a peptide comprising two ectodomains of a 4-1BBL or a fragment thereof connected to each other by a first peptide linker is fused at its C-terminus to the CL domain of a light chain by a second peptide linker and wherein one ectodomain of said 4-1BBL or a fragment thereof is fused at the its C-terminus to the CH1 domain of the heavy chain by a third peptide linker.

In a particular aspect, the invention relates to a 4-1BBL trimer-containing antigen binding molecule as defined above, wherein the peptide linker is $(G4S)_2$. In one aspect, the first peptide linker is $(G4S)_2$ (SEQ ID NO:41), the second peptide linker is $(G4S)_2$ (SEQ ID NO:41) and the third peptide linker is $(G4S)_2$ (SEQ ID NO:41).

In another aspect, the 4-1BBL trimer-containing antigen binding molecule as defined herein before comprises an Fc domain composed of a first and a second subunit capable of stable association.

In particular, the 4-1BBL trimer-containing antigen binding molecule of the invention comprises (a) a Fab molecule capable of specific binding to PD-L1, wherein the Fab heavy chain is fused at the C-terminus to the N-terminus of a CH2 domain in the Fc domain and (c) an Fc domain composed of a first and a second subunit capable of stable association.

In a further aspect, the Fc domain is an IgG, particularly an IgG1 Fc domain or an IgG4 Fc domain. More particularly, the Fc domain is an IgG1 Fc domain. In a particular aspect, the Fc domain comprises a modification promoting the association of the first and second subunit of the Fc domain.

Fc Domain Modifications Reducing Fc Receptor Binding and/or Effector Function

The Fc domain of the 4-1BBL trimer-containing antigen binding molecules of the invention consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other.

The Fc domain confers favorable pharmacokinetic properties to the antigen binding molecules of the invention, including a long serum half-life which contributes to good accumulation in the target tissue and a favorable tissue-blood distribution ratio. At the same time it may, however, lead to undesirable targeting of the bispecific antibodies of the invention to cells expressing Fc receptors rather than to the preferred antigen-bearing cells. Accordingly, in particular aspects, the Fc domain of the 4-1BBL trimer-containing antigen binding molecule of the invention exhibits reduced binding affinity to an Fc receptor and/or reduced effector function, as compared to a native IgG1 Fc domain. In one aspect, the Fc does not substantially bind to an Fc receptor and/or does not induce effector function. In a particular aspect the Fc receptor is an Fcγ receptor. In one aspect, the Fc receptor is a human Fc receptor. In a specific aspect, the Fc receptor is an activating human Fcγ receptor, more specifically human FcγRIIIa, FcγRI or FcγRIIa, most specifically human FcγRIIIa. In one aspect, the Fc domain does not induce effector function. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced dendritic cell maturation, or reduced T cell priming.

In certain aspects, one or more amino acid modifications may be introduced into the Fc region of a 4-1BBL trimer-containing antigen binding molecule provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In a particular aspect, the invention provides a 4-1BBL trimer-containing antigen binding molecule comprising (a) an antigen binding domain capable of specific binding to PD-L1, (b) a first and a second polypeptide that are linked to each other by a disulfide bond, wherein the antigen binding molecule is characterized in that the first polypeptide comprises two ectodomains of 4-1BBL or a fragment thereof that are connected to each other by a peptide linker and in that the second polypeptide comprises one ectodomain of 4-1BBL or a fragment thereof, and (c) an Fc domain composed of a first and a second subunit capable of stable association, wherein the Fc domain comprises one or more amino acid substitution that reduces binding to an Fc receptor, in particular towards Fcγ receptor.

In one aspect, the Fc domain of the 4-1BBL trimer-containing antigen binding molecule of the invention comprises one or more amino acid mutation that reduces the binding affinity of the Fc domain to an Fc receptor and/or effector function. Typically, the same one or more amino acid mutation is present in each of the two subunits of the Fc domain. In particular, the Fc domain comprises an amino acid substitution at a position of E233, L234, L235, N297, P331 and P329 (EU numbering). In particular, the Fc domain comprises amino acid substitutions at positions 234 and 235 (EU numbering) and/or 329 (EU numbering) of the IgG heavy chains. More particularly, provided is a trimeric TNF family ligand-containing antigen binding molecule according to the invention which comprises an Fc domain with the amino acid substitutions L234A, L235A and P329G ("P329G LALA", EU numbering) in the IgG heavy chains. The amino acid substitutions L234A and L235A refer to the so-called LALA mutation. The "P329G LALA" combination of amino acid substitutions almost completely abolishes Fcγ receptor binding of a human IgG1 Fc domain and is described in International Patent Appl. Publ. No. WO 2012/130831 A1 which also describes methods of preparing such mutant Fc domains and methods for determining its properties such as Fc receptor binding or effector functions. "EU numbering" refers to the numbering according to EU index of Kabat et al, Sequences of Proteins of Immunological Interest, 5th Ed. Public Health Service, National Institutes of Health, Bethesda, MD, 1991.

Fc domains with reduced Fc receptor binding and/or effector function also include those with substitution of one or more of Fc domain residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In another aspect, the Fc domain is an IgG4 Fc domain. IgG4 antibodies exhibit reduced binding affinity to Fc receptors and reduced effector functions as compared to IgG1 antibodies. In a more specific aspect, the Fc domain is an IgG4 Fc domain comprising an amino acid substitution at position S228 (Kabat numbering), particularly the amino acid substitution S228P. In a more specific aspect, the Fc domain is an IgG4 Fc domain comprising amino acid substitutions L235E and S228P and P329G (EU numbering). Such IgG4 Fc domain mutants and their Fcγ receptor binding properties are also described in WO 2012/130831.

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. A suitable such binding assay is described herein. Alternatively, binding affinity of Fc domains or cell activating bispecific antigen binding molecules comprising an Fc domain for Fc receptors may be evaluated using cell lines known to express particular Fc receptors, such as human NK cells expressing FcγIIIa receptor.

Effector function of an Fc domain, or bispecific antibodies of the invention comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, CA); and CytoTox 96® non-radioactive cytotoxicity assay (Promega, Madison, WI)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998).

In some embodiments, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the bispecific antibodies of the invention is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

In a particular aspect, the Fc domain comprises a modification promoting the association of the first and second subunit of the Fc domain.

Fc Domain Modifications Promoting Heterodimerization

In one aspect, the 4-1BBL trimer-containing antigen binding molecules of the invention comprise (a) an antigen binding domain capable of specific binding to PD-L1, (b) a first and a second polypeptide that are linked to each other by a disulfide bond, wherein the antigen binding molecule is characterized in that the first polypeptide comprises two ectodomains of 4-1BBL or a fragment thereof that are connected to each other by a peptide linker and in that the second polypeptide comprises one ectodomain of 4-1BBL or a fragment thereof, and (c) an Fc domain composed of a first and a second subunit capable of stable association. Thus, they comprise different moieties, fused to one or the other of the two subunits of the Fc domain that are typically comprised in two non-identical polypeptide chains ("heavy chains"). Recombinant co-expression of these polypeptides and subsequent dimerization leads to several possible combinations of the two polypeptides. To improve the yield and purity of the 4-1BBL trimer-containing antigen binding molecules in recombinant production, it will thus be advantageous to introduce in the Fc domain of the 4-1BBL trimer-containing antigen binding molecules of the invention a modification promoting the association of the desired polypeptides.

Accordingly, the Fc domain of the 4-1BBL trimer-containing antigen binding molecules of the invention comprises a modification promoting the association of the first and the second subunit of the Fc domain. The site of most extensive protein-protein interaction between the two subunits of a human IgG Fc domain is in the CH3 domain of the Fc domain. Thus, said modification is particularly in the CH3 domain of the Fc domain.

In a specific aspect, said modification is a so-called "knob-into-hole" modification, comprising a "knob" modification in one of the two subunits of the Fc domain and a "hole" modification in the other one of the two subunits of the Fc domain. Thus, in a particular aspect, the invention relates to a 4-1BBL trimer-containing antigen binding molecule as described herein before which comprises an IgG molecule, wherein the Fc part of the first heavy chain comprises a first dimerization module and the Fc part of the second heavy chain comprises a second dimerization module allowing a heterodimerization of the two heavy chains of the IgG molecule and the first dimerization module comprises knobs and the second dimerization module comprises holes according to the knob into hole technology.

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in a particular aspect, in the CH3 domain of the first subunit of the Fc domain of the 4-1BBL trimer-containing antigen binding molecules of the invention an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

The protuberance and cavity can be made by altering the nucleic acid encoding the polypeptides, e.g. by site-specific mutagenesis, or by peptide synthesis.

In a specific aspect, in the CH3 domain of the first subunit of the Fc domain the threonine residue at position 366 is replaced with a tryptophan residue (T366W), and in the CH3 domain of the second subunit of the Fc domain the tyrosine residue at position 407 is replaced with a valine residue (Y407V). More particularly, in the second subunit of the Fc domain additionally the threonine residue at position 366 is replaced with a serine residue (T366S) and the leucine residue at position 368 is replaced with an alanine residue (L368A). More particularly, in the first subunit of the Fc domain additionally the serine residue at position 354 is replaced with a cysteine residue (S354C), and in the second subunit of the Fc domain additionally the tyrosine residue at position 349 is replaced by a cysteine residue (Y349C). The introduction of these two cysteine residues results in the formation of a disulfide bridge between the two subunits of the Fc domain. The disulfide bridge further stabilizes the dimer (Carter, J Immunol Methods 248, 7-15 (2001)).

In an alternative aspect, a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable.

Modifications in the CH1/CL Domains

To further improve correct pairing, the 4-1BBL trimer-containing antigen binding molecules can contain different charged amino acid substitutions (so-called "charged residues"). These modifications are introduced in the crossed or non-crossed CH1 and CL domains. In a particular aspect, the invention relates to a 4-1BBL trimer-containing antigen binding molecule, wherein in one of CL domains the amino acid at position 123 (EU numbering) has been replaced by arginine (R) and the amino acid at position 124 (EU numbering) has been substituted by lysine (K) and wherein in one of the CH1 domains the amino acids at position 147 (EU numbering) and at position 213 (EU numbering) have been substituted by glutamic acid (E).

More particularly, the invention relates to a 4-1BBL trimer-containing antigen binding molecule, wherein in the CL domain adjacent to the TNF ligand family member the amino acid at position 123 (EU numbering) has been replaced by arginine (R) and the amino acid at position 124 (EU numbering) has been substituted by lysine (K), and wherein in the CH1 domain adjacent to the TNF ligand family member the amino acids at position 147 (EU numbering) and at position 213 (EU numbering) have been substituted by glutamic acid (E).

Thus, in a particular aspect, provided is a 4-1BBL trimer-containing antigen binding molecule comprising (a) an antigen binding domain capable of specific binding to PD-L1, (b) a first polypeptide containing a CL domain comprising the amino acid mutations E123R and Q124K and a second polypeptide containing a CH1 domain comprising the amino acid mutations K147E and K213E, wherein the second polypeptide is linked to the first polypeptide by a disulfide bond between the CH1 and CL domain, and wherein the antigen binding molecule is characterized in that the first polypeptide comprises two ectodomains of 4-1BBL or a fragment thereof that are connected to each other and to the CL domain by a peptide linker and in that the second polypeptide comprises one 4-1BBL or a fragment thereof connected via a peptide linker to the CH1 domain of said polypeptide; and (c) an Fc domain composed of a first and a second subunit capable of stable association.

In one aspect, the invention provides a 4-1BBL trimer-containing antigen binding molecule, wherein in the CL domain adjacent to the TNF ligand family member the amino acid at position 123 (EU numbering) has been replaced by arginine (R) and the amino acid at position 124 (EU numbering) has been substituted by lysine (K), and wherein in the CH1 domain adjacent to the TNF ligand family member the amino acids at position 147 (EU numbering) and at position 213 (EU numbering) have been substituted by glutamic acid (E). These modifications lead to so-called charged residues with advantageous properties that avoid undesired effects such as for example mispairing.

In particular, the CL domain comprises the amino acid mutations E123R and Q124K and the CH1 domain comprises the amino acid mutations K147E and K213E.

Particular 4-1BBL Trimer-Containing Antigen Binding Molecules

The invention provides a 4-1BBL trimer-containing antigen binding molecule that comprises an antigen binding domain capable of specific binding to PD-L1. In a particular aspect, the 4-1BBL trimer-containing antigen binding molecule comprises one moiety capable of specific binding to PD-L1, meaning the 4-1BBL trimer-containing antigen binding molecule is monovalent. In another aspect, the invention provides a 4-1BBL trimer-containing antigen binding molecule comprising two moieties capable of specific binding to PD-L1, meaning the 4-1BBL trimer-containing antigen binding molecule is bivalent.

In one aspect, the invention provides a 4-1BBL trimer-containing antigen binding molecule, wherein the antigen binding domain capable of specific binding to PD-L1 comprises a heavy chain variable region ($V_H$PD-L1) comprising (i) CDR-H1 comprising the amino acid sequence of SEQ ID NO:13, (ii) CDR-H2 comprising the amino acid sequence of SEQ ID NO:14, and (iii) CDR-H3 comprising the amino acid sequence of SEQ ID NO:15, and a light chain variable region ($V_L$PD-L1) comprising (iv) CDR-L1 comprising the amino acid sequence of SEQ ID NO:16, (v) CDR-L2 comprising the amino acid sequence of SEQ ID NO:17, and (vi) CDR-L3 comprising the amino acid sequence of SEQ ID NO:18.

In one aspect, the invention provides a 4-1BBL trimer-containing antigen binding molecule, wherein the antigen binding domain capable of specific binding to PD-L1 comprises a VH domain comprising (i) CDR-H1 comprising the amino acid sequence of SEQ ID NO:13, (ii) CDR-H2 comprising the amino acid sequence of SEQ ID NO:14, and (iii) CDR-H3 comprising the amino acid sequence of SEQ ID NO:15, and a VL domain comprising (iv) CDR-L1 comprising the amino acid sequence of SEQ ID NO:16, (v) CDR-L2 comprising the amino acid sequence of SEQ ID NO:17, and (vi) CDR-L3 comprising the amino acid sequence of SEQ ID NO:18.

In a further aspect, the antigen binding domain capable of specific binding to PD-L1 comprises a heavy chain variable region comprising an amino acid sequence that is at least about 95%, 96%, 97%, 98%, 99% or 100% identical to the amino acid sequence of SEQ ID NO:19 and a light chain variable region comprising an amino acid sequence that is at least about 95%, 96%, 97%, 98%, 99% or 100% identical to the amino acid sequence of SEQ ID NO:20.

In a further aspect, the invention provides a a 4-1BBL trimer-containing antigen binding molecule, wherein the antigen binding domain capable of specific binding to PD-L1 comprises a VH domain comprising an amino acid sequence of SEQ ID NO:19 and a VL domain comprising an amino acid sequence of SEQ ID NO:20.

In a further aspect, the 4-1BBL trimer-containing antigen binding molecule of the invention comprises (i) a first heavy chain comprising the VH domain comprising the amino acid sequence of SEQ ID NO:19 and a first light chain comprising the VL domain comprising the amino acid sequence of SEQ ID NO:20, (ii) a second heavy chain comprising the amino acid sequence selected from the group consisting of SEQ ID NO:21, SEQ ID NO:23, SEQ ID NO:25 and SEQ ID NO:27, and (iii) a second light chain comprising the amino acid sequence selected from the group consisting of SEQ ID NO:22, SEQ ID NO:24, SEQ ID NO:26 and SEQ ID NO:28.

In a particular aspect, the 4-1BBL trimer-containing antigen binding molecule of the invention comprises (a) an antigen binding domain of specific binding to PD-L1 comprising a heavy chain variable region comprising the amino acid sequence of SEQ ID NO:19 and a light chain variable region comprising the amino acid sequence of SEQ ID NO:20, and (b) a first and a second polypeptide that are linked to each other by a disulfide bond, wherein the antigen binding molecule is characterized in that the first polypeptide comprises the the amino acid sequence of SEQ ID NO:10 and the second polypeptide comprises the amino acid sequence of SEQ ID NO:5.

In a particular aspect, provided is a 4-1BBL trimer-containing antigen binding molecule, wherein the antigen binding molecule comprises a first heavy chain comprising an amino acid sequence that is at least about 95%, 96%, 97%, 98%, 99% or 100% identical to the amino acid sequence of SEQ ID NO:29, a first light chain comprising an amino acid sequence that is at least about 95%, 96%, 97%, 98%, 99% or 100% identical to the amino acid sequence of SEQ ID NO:30, a second heavy chain comprising an amino acid sequence that is at least about 95%, 96%, 97%, 98%, 99% or 100% identical to the amino acid sequence of SEQ ID NO:21 and a second light chain comprising an amino acid sequence that is at least about 95%, 96%, 97%, 98%, 99% or 100% identical to the amino acid sequence of SEQ ID NO:22.

In another aspect, the invention provides a 4-1BBL trimer-containing antigen binding molecule, wherein the antigen binding molecule comprises a first heavy chain comprising an amino acid sequence of SEQ ID NO:29, a first light chain comprising an amino acid sequence of SEQ ID NO:30, a second heavy chain comprising an amino acid sequence of SEQ ID NO:21 and a second light chain comprising an amino acid sequence of SEQ ID NO:22.

Polynucleotides

The invention further provides isolated nucleic acid molecules encoding a 4-1BBL trimer-containing antigen binding molecule as described herein or a fragment thereof.

The isolated polynucleotides encoding 4-1BBL trimer-containing antigen binding molecules of the invention may be expressed as a single polynucleotide that encodes the entire antigen binding molecule or as multiple (e.g., two or more) polynucleotides that are co-expressed. Polypeptides encoded by polynucleotides that are co-expressed may associate through, e.g., disulfide bonds or other means to form a functional antigen binding molecule. For example, the light chain portion of an immunoglobulin may be encoded by a separate polynucleotide from the heavy chain portion of the immunoglobulin. When co-expressed, the heavy chain polypeptides will associate with the light chain polypeptides to form the immunoglobulin.

In some aspects, the isolated nucleic acid molecule encodes the entire 4-1BBL trimer-containing antigen binding molecule according to the invention as described herein. In particular, the isolated polynucleotide encodes a polypeptide comprised in the 4-1BBL trimer-containing antigen binding molecule according to the invention as described herein.

In one aspect, the present invention is directed to isolated nucleic acid molecules encoding a 4-1BBL trimer-containing antigen binding molecule, wherein the nucleic acid molecule comprises (a) a sequence that encodes an antigen binding domain capable of specific binding to a PD-L1, (b) a sequence that encodes a polypeptide comprising two ectodomains of 4-1BBL or a fragment thereof that are connected to each other by a peptide linker and (c) a sequence that encodes a polypeptide comprising one ectodomain of said 4-1BBL or a fragment thereof.

In another aspect, provided is an isolated polynucleotide encoding a 4-1BB ligand trimer-containing antigen binding molecule, wherein the polynucleotide comprises (a) a sequence that encodes a moiety capable of specific binding to PD-L1, (b) a sequence that encodes a polypeptide comprising two ectodomains of 4-1BBL or two fragments thereof that are connected to each other by a peptide linker and (c) a sequence that encodes a polypeptide comprising one ectodomain of 4-1BBL or a fragment thereof.

In certain aspects, the polynucleotide or nucleic acid is DNA. In other embodiments, a polynucleotide of the present invention is RNA, for example, in the form of messenger RNA (mRNA). RNA of the present invention may be single stranded or double stranded.

Recombinant Methods 4-1BBL trimer-containing antigen binding molecules of the invention may be obtained, for example, by solid-state peptide synthesis (e.g. Merrifield solid phase synthesis) or recombinant production. For recombinant production one or more polynucleotide encoding the 4-1BBL trimer-containing antigen binding molecule or polypeptide fragments thereof, e.g., as described above, is isolated and inserted into one or more vectors for further cloning and/or expression in a host cell. Such polynucleotide may be readily isolated and sequenced using conventional procedures. In one aspect of the invention, a vector, preferably an expression vector, comprising one or more of the polynucleotides of the invention is provided. Methods which are well known to those skilled in the art can be used to construct expression vectors containing the coding sequence of the 4-1BBL trimer-containing antigen binding molecule (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y. (1989). The expression vector can be part of a plasmid, virus, or may be a nucleic acid fragment. The expression vector includes an expression cassette into which the polynucleotide encoding the 4-1BBL trimer-containing antigen binding molecule or polypeptide fragments thereof (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the 4-1BBL trimer-containing antigen binding molecule of the invention or polypeptide fragments thereof, or variants or derivatives thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription.

Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit A-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the 4-1BBL trimer-containing antigen binding molecule or polypeptide fragments thereof is desired, DNA encoding a signal sequence may be placed upstream of the nucleic acid encoding a 4-1BBL trimer-containing antigen binding molecule of the invention or polypeptide fragments thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the fusion protein may be included within or at the ends of the polynucleotide encoding a 4-1BBL trimer-containing antigen binding molecule of the invention or polypeptide fragments thereof.

In a further aspect of the invention, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one aspect, a host cell comprises (e.g. has been transformed or transfected with) a vector comprising a polynucleotide that encodes (part of) a 4-1BBL trimer-containing antigen binding molecule of the invention of the invention. As used herein, the term "host cell" refers to any kind of cellular system which can be engineered to generate the fusion proteins of the invention or fragments thereof. Host cells suitable for replicating and for supporting expression of antigen binding molecules are well known in the art. Such cells may be transfected or transduced as appropriate with the particular expression vector and large quantities of vector containing cells can be grown for seeding large scale fermenters to obtain sufficient quantities of the antigen binding molecule for clinical applications. Suitable host cells include prokaryotic microorganisms, such as *E. coli*, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006).

Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr− CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B.K.C. Lo, ed., Humana Press, Totowa, NJ), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., Y0, NS0, Sp20 cell). Standard technologies are known in the art to express foreign genes in these systems. Cells expressing a polypeptide comprising either the heavy or the light chain of an immunoglobulin, may be engineered so as to also express the other of the immunoglobulin chains such that the expressed product is an immunoglobulin that has both a heavy and a light chain.

In one aspect, a method of producing a 4-1BBL trimer-containing antigen binding molecule of the invention or polypeptide fragments thereof is provided, wherein the method comprises culturing a host cell comprising polynucleotides encoding the 4-1BBL trimer-containing antigen binding molecule of the invention or polypeptide fragments thereof, as provided herein, under conditions suitable for expression of the 4-1BBL trimer-containing antigen binding molecule of the invention or polypeptide fragments thereof, and recovering the 4-1BBL trimer-containing antigen binding molecule of the invention or polypeptide fragments thereof from the host cell (or host cell culture medium).

In the 4-1BBL trimer-containing antigen binding molecule of the invention, the components (at least one moiety capable of specific binding to a target cell antigen, one polypeptide comprising two ectodomains of 4-1BBL or fragments thereof and a polypeptide comprising one ectodomain of said 4-1BBL or a fragment thereof) are not genetically fused to each other. The polypeptides are designed such that its components (two ectodomains of a TNF ligand family member or fragments thereof and other components such as CH or CL) are fused to each other directly or through a linker sequence. The composition and length of the linker may be determined in accordance with methods well known in the art and may be tested for efficacy. Examples of linker sequences between different components of the antigen binding molecules of the invention are found in the sequences provided herein. Additional sequences may also be included to incorporate a cleavage site to separate the individual components of the fusion protein if desired, for example an endopeptidase recognition sequence.

In certain embodiments the moieties capable of specific binding to a target cell antigen (e.g. Fab fragments) forming part of the antigen binding molecule comprise at least an immunoglobulin variable region capable of binding to an antigen. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty).

Any animal species of immunoglobulin can be used in the invention. Non-limiting immunoglobulins useful in the present invention can be of murine, primate, or human origin. If the fusion protein is intended for human use, a chimeric form of immunoglobulin may be used wherein the constant regions of the immunoglobulin are from a human. A humanized or fully human form of the immunoglobulin can also be prepared in accordance with methods well known in the art (see e. g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Particular immunoglobulins according to the invention are human immunoglobulins. Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, NJ, 2001); and McCafferty et al., Nature 348, 552-554; Clackson et al., Nature 352, 624-628 (1991)). Phage typically display antibody fragments, either as single-chain Fv (scFv) fragments or as Fab fragments.

In certain aspects, the moieties capable of specific binding to PD-L1 (e.g. Fab fragments) comprised in the antigen binding molecules of the present invention are engineered to have enhanced binding affinity according to, for example, the methods disclosed in PCT publication WO 2012/020006 (see Examples relating to affinity maturation) or U.S. Pat. Appl. Publ. No. 2004/0132066. The ability of the antigen binding molecules of the invention to bind to a specific antigenic determinant can be measured either through an enzyme-linked immunosorbent assay (ELISA) or other techniques familiar to one of skill in the art, e.g. surface plasmon resonance technique (Liljeblad, et al., Glyco J 17, 323-329 (2000)), and traditional binding assays (Heeley, Endocr Res 28, 217-229 (2002)). Competition assays may be used to identify an antigen binding molecule that competes with a reference antibody for binding to a particular antigen. In certain embodiments, such a competing antigen binding molecule binds to the same epitope (e.g. a linear or a conformational epitope) that is bound by the reference antigen binding molecule. Detailed exemplary methods for mapping an epitope to which an antigen binding molecule binds are provided in Morris (1996) "Epitope Mapping Protocols", in Methods in Molecular Biology vol. 66 (Humana Press, Totowa, NJ). In an exemplary competition assay, immobilized antigen is incubated in a solution comprising a first labeled antigen binding molecule that binds to the antigen and a second unlabeled antigen binding molecule that is being tested for its ability to compete with the first antigen binding molecule for binding to the antigen. The second antigen binding molecule may be present in a hybridoma supernatant. As a control, immobilized antigen is incubated in a solution comprising the first labeled antigen binding molecule but not the second unlabeled antigen binding molecule. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antigen binding molecule is competing with the first antigen binding molecule for binding to the antigen. See Harlow and Lane (1988) Antibodies: A Laboratory Manual ch.14 (Cold Spring Harbor Laboratory, Cold Spring Harbor, NY).

4-1BBL trimer-containing antigen binding molecules of the invention prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the 4-1BBL trimer-containing antigen binding molecule binds. For example, for affinity chromatography purification of fusion proteins of the invention, a matrix with protein A or protein G may be used. Sequential Protein A or G affinity chromatography and size exclusion chromatography can be used to isolate an antigen binding molecule essentially as described in the Examples. The purity of the 4-1BBL trimer-containing antigen binding molecule or fragments thereof can be determined by any of a variety of well-known analytical methods including gel electrophoresis, high pressure liquid chromatography, and the like. For example, the 4-1BBL trimer-containing antigen binding molecules expressed as described in the Examples were shown to be intact and properly assembled as demonstrated by reducing and non-reducing SDS-PAGE.

Assays

The antigen binding molecules provided herein may be identified, screened for, or characterized for their physical/chemical properties and/or biological activities by various assays known in the art. Biological activity may include, e.g., the ability to enhance the activation and/or proliferation of different immune cells especially T-cells. E.g. they enhance secretion of immunomodulating cytokines. Other immunomodulating cytokines which are or can be enhanced are e.g IL2, Granzyme B etc. Biological activity may also include, cynomolgus binding crossreactivity, as well as binding to different cell types. Antigen binding molecules having such biological activity in vivo and/or in vitro are also provided.

1. Affinity Assays

The affinity of the 4-1BBL trimer-containing antigen binding molecule provided herein for 4-1BB (CD137) can be determined in accordance with the methods set forth in the Examples by surface plasmon resonance (SPR), using standard instrumentation such as a BIAcore instrument (GE Healthcare), and receptors or target proteins such as may be obtained by recombinant expression. The affinity of the 4-1BBL trimer-containing antigen binding molecule for PD-L1 can also be determined by surface plasmon resonance (SPR), using standard instrumentation such as a BIAcore instrument (GE Healthcare), and receptors or target proteins such as may be obtained by recombinant expression. A specific illustrative and exemplary embodiment for measuring binding affinity is described in Example 4. According to one aspect, $K_D$ is measured by surface plasmon resonance using a BIACORE® T100 machine (GE Healthcare) at 25° C.

2. Binding Assays and Other Assays

Binding of the 4-1BBL trimer-containing antigen binding molecule provided herein to the corresponding receptor expressing cells may be evaluated using cell lines expressing the particular receptor or target antigen, for example by flow cytometry (FACS). In one aspect, fresh peripheral blood mononuclear cells (PBMCs) expressing 4-1BB can be used in the binding assay. These cells are used directly after isolation (naïve PMBCs) or after stimulation (activated PMBCs). In another aspect, activated mouse splenocytes (expressing 4-1BB) can be used to demonstrate the binding of the 4-1BBL trimer-containing antigen binding molecule of the invention to 4-1BB expressing cells.

In a further aspect, cell lines expressing PD-L1 were used to demonstrate the binding of the antigen binding molecules to this target cell antigen.

In another aspect, competition assays may be used to identify an antigen binding molecule that competes with a specific antibody or antigen binding molecule for binding to PD-L1 or 4 -1BB, respectively. In certain embodiments, such a competing antigen binding molecule binds to the same epitope (e.g., a linear or a conformational epitope) that is bound by a specific anti-PD-L1 antibody or a specific 4-1BB antibody. Detailed exemplary methods for mapping an epitope to which an antibody binds are provided in Morris (1996) "Epitope Mapping Protocols," in *Methods in Molecular Biology* vol. 66 (Humana Press, Totowa, NJ).

3. Activity Assays

In one aspect, assays are provided for identifying 4-1BBL trimer-containing antigen binding molecules that bind to PD-L1 and to 4-1BB having biological activity. Biological activity may include, e.g., agonistic signalling through 4-1BB on cells expressing PD-L1. 4-1BBL trimer-containing antigen binding molecules identified by the assays as having such biological activity in vitro are also provided.

In certain aspects, a 4-1BBL trimer-containing antigen binding molecule of the invention is tested for such biological activity. Assays for detecting the biological activity of the molecules of the invention are those described in Example 3. Furthermore, assays for detecting cell lysis (e.g. by measurement of LDH release), induced apoptosis kinetics (e.g. by measurement of Caspase 3/7 activity) or apoptosis (e.g. using the TUNEL assay) are well known in the art. In addition, the biological activity of such complexes can be assessed by evaluating their effects on survival, proliferation and lymphokine secretion of various lymphocyte subsets such as NK cells, NKT-cells or γδ T-cells or assessing their capacity to modulate phenotype and function of antigen presenting cells such as dendritic cells, monocytes/macrophages or B-cells.

Pharmaceutical Compositions, Formulations and Routes of Administration

In a further aspect, the invention provides pharmaceutical compositions comprising any of the 4-1BBL trimer-containing antigen binding molecules provided herein, e.g., for use in any of the below therapeutic methods. In one embodiment, a pharmaceutical composition comprises any of the 4-1BBL trimer-containing antigen binding molecules provided herein and at least one pharmaceutically acceptable excipient. In another embodiment, a pharmaceutical composition comprises any of the 4-1BBL trimer-containing antigen binding molecules provided herein and at least one additional therapeutic agent, e.g., as described below.

Pharmaceutical compositions of the present invention comprise a therapeutically effective amount of one or more 4-1BBL trimer-containing antigen binding molecules dissolved or dispersed in a pharmaceutically acceptable excipient. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one 4-1BBL trimer-containing antigen binding molecule and optionally an additional active ingredient will be known to those of skill in the art in light of the present disclosure, as exemplified by Remington's Pharmaceutical Sciences, 18th Ed. Mack Printing Company, 1990, incorporated herein by reference. In particular, the compositions are lyophilized formulations or aqueous solutions. As used herein, "pharmaceutically acceptable excipient" includes any and all solvents, buffers, dispersion media, coatings, surfactants, antioxidants, preservatives (e.g. antibacterial agents, antifungal agents), isotonic agents, salts, stabilizers and combinations thereof, as would be known to one of ordinary skill in the art.

Parenteral compositions include those designed for administration by injection, e.g. subcutaneous, intradermal, intralesional, intravenous, intraarterial intramuscular, intrathecal or intraperitoneal injection. For injection, the 4-1BBL trimer-containing antigen binding molecules of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the fusion proteins may be in powder form for constitution with a suitable vehicle, e.g., sterile pyrogen-free water, before use. Sterile injectable solutions are prepared by incorporating the fusion proteins of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable excipients include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

Exemplary pharmaceutically acceptable excipients herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

In addition to the compositions described previously, the fusion proteins may also be formulated as a depot preparation. Such long acting formulations may be administered by implantation (for example subcutaneously or intramuscularly) or by intramuscular injection. Thus, for example, the fusion proteins may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the fusion proteins of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The 4-1BBL trimer-containing antigen binding molecules may be formulated into a composition in a free acid or base, neutral or salt form. Pharmaceutically acceptable salts are salts that substantially retain the biological activity of the free acid or base. These include the acid addition salts, e.g. those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

The composition herein may also contain more than one active ingredients as necessary for the particular indication being treated, preferably those with complementary activities that do not adversely affect each other. Such active ingredients are suitably present in combination in amounts that are effective for the purpose intended.

In one aspect, the pharmaceutical compositions may comprise any of the 4-1BBL trimer-containing antigen binding molecules provided herein and at least one additional therapeutic agent. In one aspect, the pharmaceutical compositions may comprise any of the 4-1BBL trimer-containing antigen binding molecules provided herein and a T-cell activating anti-CD3 bispecific antibody. In one aspect, the T-cell activating anti-CD3 bispecific antibody comprises a first antigen binding domain that binds to CD3, and a second antigen binding domain that binds to a tumor-associated antigen.

The formulations to be used for in vivo administration are generally sterile. Sterility may be readily accomplished, e.g., by filtration through sterile filtration membranes.

Therapeutic Methods and Compostions

Any of the 4-1BBL trimer-containing antigen binding molecules provided herein may be used in therapeutic methods.

For use in therapeutic methods, 4-1BBL trimer-containing antigen binding molecules of the invention can be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, 4-1BBL trimer-containing antigen binding molecules of the invention for use as a medicament are provided. In further aspects, 4-1BBL trimer-containing antigen binding molecules of the invention for use in treating a disease, in particular for use in the treatment of cancer, are provided. In certain aspects, 4-1BBL trimer-containing antigen binding molecules of the invention for use in a method of treatment are provided. In one aspect, the invention provides a 4-1BBL trimer-containing antigen binding molecule as described herein for use in the treatment of a disease in an individual in need thereof. In certain aspects, the invention provides a 4-1BBL trimer-containing antigen binding molecule for use in a method of treating an individual having a disease comprising administering to the individual a therapeutically effective amount of the fusion protein. In certain aspects, the disease to be treated is cancer. Examples of cancers include breast cancer, ovarian cancer, gastric cancer, bladder cancer, salivary gland, endometrial cancer, pancreatic cancer and non-small-cell lung cancer (NSCLC). In one aspect, the cancer is a solid tumor. In some aspects, the cancer is already an advanced cancer. Thus, a 4-1BBL trimer-containing antigen binding molecule as described herein for use in the treatment of these cancers is provided. The subject, patient, or "individual" in need of treatment is typically a mammal, more specifically a human.

In another aspect, provided is a 4-1BBL trimer-containing antigen binding molecule as described herein for use in the treatment of infectious diseases, in particular for the treatment of viral infections. In a further aspect, provided is a 4-1BBL trimer-containing antigen binding molecule as described herein for use in the treatment of autoimmune diseases such as for example Lupus disease.

In a further aspect, the invention relates to the use of a 4-1BBL trimer-containing antigen binding molecule in the manufacture or preparation of a medicament for the treatment of a disease in an individual in need thereof. In one aspect, the medicament is for use in a method of treating a disease comprising administering to an individual having the disease a therapeutically effective amount of the medicament. In certain embodiments the disease to be treated is a proliferative disorder, particularly cancer. Thus, in one aspect, the invention relates to the use of a 4-1BBL trimer-containing antigen binding molecule of the invention in the manufacture or preparation of a medicament for the treatment of cancer, in particular cancers. Examples of cancers include breast cancer, ovarian cancer, gastric cancer, bladder cancer, salivary gland, endometrial cancer, pancreatic cancer and non-small-cell lung cancer (NSCLC). A skilled artisan may recognize that in some cases the 4-1BBL trimer-containing antigen binding molecule may not provide a cure but may only provide partial benefit. In some aspects, a physiological change having some benefit is also considered therapeutically beneficial. Thus, in some aspects, an amount of 4-1BBL trimer-containing antigen binding molecule that provides a physiological change is considered an "effective amount" or a "therapeutically effective amount".

In a further aspect, the invention provides a method for treating a disease in an individual, comprising administering to said individual a therapeutically effective amount of a 4-1BBL trimer-containing antigen binding molecule of the invention. In one aspect a composition is administered to said individual, comprising a fusion protein of the invention in a pharmaceutically acceptable form. In certain aspects, the disease to be treated is a proliferative disorder. In a particular aspect, the disease is cancer. In certain aspects, the method further comprises administering to the individual a therapeutically effective amount of at least one additional therapeutic agent, e.g. an anti-cancer agent if the disease to be treated is cancer. An "individual" according to any of the above embodiments may be a mammal, preferably a human.

For the prevention or treatment of disease, the appropriate dosage of a 4-1BBL trimer-containing antigen binding molecule of the invention (when used alone or in combination with one or more other additional therapeutic agents) will depend on the type of disease to be treated, the route of administration, the body weight of the patient, the type of antigen binding molecule, the severity and course of the disease, whether the fusion protein is administered for preventive or therapeutic purposes, previous or concurrent therapeutic interventions, the patient's clinical history and response to the fusion protein, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The 4-1BBL trimer-containing antigen binding molecule is suitably administered to the patient at one time or over a series of treatments. Depending on the type and severity of the disease, about 1 μg/kg to 15 mg/kg (e.g. 0.1 mg/kg-10 mg/kg) of 4-1BBL trimer-containing antigen binding molecule can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the fusion protein would be in the range from about 0.005 mg/kg to about 10 mg/kg. In other examples, a dose may also comprise from about 1 μg/kg body weight, about 5 μg/kg body weight, about 10 μg/kg body weight, about 50 μg/kg body weight, about 100 μg/kg body weight, about 200 μg/kg body weight, about 350 μg/kg body weight, about 500 μg/kg body weight, about 1 mg/kg body weight, about 5 mg/kg body weight, about 10 mg/kg body weight, about 50 mg/kg body weight, about 100 mg/kg body weight, about 200 mg/kg body weight, about 350 mg/kg body weight, about 500 mg/kg body weight, to about 1000 mg/kg body weight or more per administration, and any range derivable therein. In examples of a derivable range from the numbers listed herein, a range of about 5 mg/kg body weight to about 100 mg/kg body weight, about 5 μg/kg body weight to about 500 mg/kg body weight etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the fusion protein). An initial higher loading dose, followed by one or more lower doses may be administered. However, other dosage regimens may be useful. The progress of this therapy is easily monitored by conventional techniques and assays.

The 4-1BBL trimer-containing antigen binding molecules of the invention will generally be used in an amount effective to achieve the intended purpose. For use to treat or prevent a disease condition, the 4-1BBL trimer-containing antigen binding molecules of the invention, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the 4-1BBL trimer-containing antigen binding molecules which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

In cases of local administration or selective uptake, the effective local concentration of the 4-1BBL trimer-containing antigen binding molecule may not be related to plasma concentration. One skilled in the art will be able to optimize therapeutically effective local dosages without undue experimentation.

A therapeutically effective dose of the 4-1BBL trimer-containing antigen binding molecules described herein will generally provide therapeutic benefit without causing substantial toxicity. Toxicity and therapeutic efficacy of a fusion protein can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. 4-1BBL trimer-containing antigen binding molecules that exhibit large therapeutic indices are preferred. In one embodiment, the 4-1BBL trimer-containing antigen binding molecule according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The Pharmacological Basis of Therapeutics, Ch. 1, p. 1, incorporated herein by reference in its entirety).

The attending physician for patients treated with fusion proteins of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Other Agents and Treatments

The 4-1BBL trimer-containing antigen binding molecules of the invention may be administered in combination with one or more other agents in therapy. For instance, a fusion protein of the invention may be co-administered with at least one additional therapeutic agent. The term "therapeutic agent" encompasses any agent that can be administered for treating a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is another anti-cancer agent.

Such other agents are suitably present in combination in amounts that are effective for the purpose intended. The effective amount of such other agents depends on the amount of 4-1BBL trimer-containing antigen binding molecule used, the type of disorder or treatment, and other factors discussed above. The 4-1BBL trimer-containing antigen binding molecules are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the 4-1BBL trimer-containing antigen binding molecule of the invention can occur prior to, simultaneously, and/or following, administration of the additional therapeutic agent and/or adjuvant.

Thus, in one aspect a 4-1BBL trimer-containing antigen binding molecule as described herein for use in the treatment of cancer is provided, wherein the 4-1BBL trimer-containing antigen binding molecule is used in combination with a T-cell activating anti-CD3 bispecific antibody. In one aspect, the anti-TA/anti-CD3 antibody comprises a first antigen binding domain that binds to CD3, and a second antigen binding domain that binds to tumor associated antigen.

In a further aspect, the 4-1BBL trimer-containing antigen binding molecule is used in combination with a T-cell activating anti-CD3 bispecific antibody and the T-cell activating anti-CD3 bispecific antibody is administered concurrently with, prior to, or subsequently to the 4-1BBL trimer-containing antigen binding molecule.

In a further aspect, provided is the use of the 4-1BBL trimer-containing antigen binding molecule for the manufacture of a medicament for the treatment of cancer, wherein the 4-1BBL trimer-containing antigen binding molecule is used in combination with a T-cell activating anti-CD3 bispecific antibody. Examples of cancers include breast cancer, ovarian cancer, gastric cancer, bladder cancer, salivary gland, endometrial cancer, pancreatic cancer and non-small-cell lung cancer (NSCLC).

In a further aspect, the invention provides a method for treating cancer in an individual, comprising administering to said individual a therapeutically effective amount of a 4-1BBL trimer-containing antigen binding molecule of the invention and an effective amount a T-cell activating anti-CD3 bispecific antibody. Examples of cancers include breast cancer, ovarian cancer, gastric cancer, bladder cancer, salivary gland, endometrial cancer, pancreatic cancer and non-small-cell lung cancer (NSCLC).

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper that is pierceable by a hypodermic injection needle). At least one active agent in the composition is a 4-1BBL trimer-containing antigen binding molecule of the invention.

The label or package insert indicates that the composition is used for treating the condition of choice. Moreover, the article of manufacture may comprise (a) a first container with a composition contained therein, wherein the composition comprises a 4-1BBL trimer-containing antigen binding molecule of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition.

Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

TABLE B (Sequences):

| SEQ ID NO: | Description | Sequence |
|---|---|---|
| 1 | Human (hu) 4-1BBL (71-254) | REGPELSPDDPAGLLDLRQGMFAQLVAQNVLLIDG PLSWYSDPGLAGVSLTGGLSYKEDTKELVVAKAGV YYVFFQLELRRVVAGEGSGSVSLALHLQPLRSAAG AAALALTVDLPPASSEARNSAFGFQGRLLHLSAGQ RLGVHLHTEARARHAWQLTQGATVLGLFRVTPEIP AGLPSPRSE |
| 2 | hu 4-1BBL (85-254) | LDLRQGMFAQLVAQNVLLIDGPLSWYSDPGLAGVS LTGGLSYKEDTKELVVAKAGVYYVFFQLELRRVVA GEGSGSVSLALHLQPLRSAAGAAALALTVDLPPAS SEARNSAFGFQGRLLHLSAGQRLGVHLHTEARARH AWQLTQGATVLGLFRVTPEIPAGLPSPRSE |
| 3 | hu 4-1BBL (80-254) | DPAGLLDLRQGMFAQLVAQNVLLIDGPLSWYSDPG LAGVSLTGGLSYKEDTKELVVAKAGVYYVFFQLEL RRVVAGEGSGSVSLALHLQPLRSAAGAAALALTVD LPPASSEARNSAFGFQGRLLHLSAGQRLGVHLHTE ARARHAWQLTQGATVLGLFRVTPEIPAGLPSPRSE |
| 4 | hu 4-1BBL (52-254) | PWAVSGARASPGSAASPRLREGPELSPDDPAGLLD LRQGMFAQLVAQNVLLIDGPLSWYSDPGLAGVSLT GGLSYKEDTKELVVAKAGVYYVFFQLELRRVVAGE GSGSVSLALHLQPLRSAAGAAALALTVDLPPASSE ARNSAFGFQGRLLHLSAGQRLGVHLHTEARARHAW QLTQGATVLGLFRVTPEIPAGLPSPRSE |
| 5 | Human (hu) 4-1BBL (71-248) | REGPELSPDDPAGLLDLRQGMFAQLVAQNVLLIDG PLSWYSDPGLAGVSLTGGLSYKEDTKELVVAKAGV YYVFFQLELRRVVAGEGSGSVSLALHLQPLRSAAG AAALALTVDLPPASSEARNSAFGFQGRLLHLSAGQ RLGVHLHTEARARHAWQLTQGATVLGLFRVTPEIP AGL |

TABLE B-continued (Sequences):

| SEQ ID NO: | Description | Sequence |
|---|---|---|
| 6 | hu 4-1BBL (85-248) | LDLRQGMFAQLVAQNVLLIDGPLSWYSDPGLAGVS LTGGLSYKEDTKELVVAKAGVYYVFFQLELRRVVA GEGSGSVSLALHLQPLRSAAGAAALALTVDLPPAS SEARNSAFGFQGRLLHLSAGQRLGVHLHTEARARH AWQLTQGATVLGLFRVTPEIPAGL |
| 7 | hu 4-1BBL (80-248) | DPAGLLDLRQGMFAQLVAQNVLLIDGPLSWYSDPG LAGVSLTGGLSYKEDTKELVVAKAGVYYVFFQLEL RRVVAGEGSGSVSLALHLQPLRSAAGAAALALTVD LPPASSEARNSAFGFQGRLLHLSAGQRLGVHLHTE ARARHAWQLTQGATVLGLFRVTPEIPAGL |
| 8 | hu 4-1BBL (52-248) | PWAVSGARASPGSAASPRLREGPELSPDDPAGLLD LRQGMFAQLVAQNVLLIDGPLSWYSDPGLAGVSLT GGLSYKEDTKELVVAKAGVYYVFFQLELRRVVAGE GSGSVSLALHLQPLRSAAGAAALALTVDLPPASSE ARNSAFGFQGRLLHLSAGQRLGVHLHTEARARHAW QLTQGATVLGLFRVTPEIPAGL |
| 9 | dimeric hu 4-1BBL (71-254) connected by $(G4S)_2$ linker | REGPELSPDDPAGLLDLRQGMFAQLVAQNVLLIDG PLSWYSDPGLAGVSLTGGLSYKEDTKELVVAKAGV YYVFFQLELRRVVAGEGSGSVSLALHLQPLRSAAG AAALALTVDLPPASSEARNSAFGFQGRLLHLSAGQ RLGVHLHTEARARHAWQLTQGATVLGLFRVTPEIP AGLPSPRSEGGGGSGGGGSREGPELSPDDPAGLLD LRQGMFAQLVAQNVLLIDGPLSWYSDPGLAGVSLT GGLSYKEDTKELVVAKAGVYYVFFQLELRRVVAGE GSGSVSLALHLQPLRSAAGAAALALTVDLPPASSE ARNSAFGFQGRLLHLSAGQRLGVHLHTEARARHAW QLTQGATVLGLFRVTPEIPAGLPSPRSE |
| 10 | dimeric hu 4-1BBL (71-248) connected by $(G4S)_2$ linker | REGPELSPDDPAGLLDLRQGMFAQLVAQNVLLIDG PLSWYSDPGLAGVSLTGGLSYKEDTKELVVAKAGV YYVFFQLELRRVVAGEGSGSVSLALHLQPLRSAAG AAALALTVDLPPASSEARNSAFGFQGRLLHLSAGQ RLGVHLHTEARARHAWQLTQGATVLGLFRVTPEIP AGLGGGGSGGGGSREGPELSPDDPAGLLDLRQGMF AQLVAQNVLLIDGPLSWYSDPGLAGVSLTGGLSYK EDTKELVVAKAGVYYVFFQLELRRVVAGEGSGSVS LALHLQPLRSAAGAAALALTVDLPPASSEARNSAF GFQGRLLHLSAGQRLGVHLHTEARARHAWQLTQGA TVLGLFRVTPEIPAGL |
| 11 | dimeric hu 4-1BBL (80-254) connected by $(G4S)_2$ linker | DPAGLLDLRQGMFAQLVAQNVLLIDGPLSWYSDPG LAGVSLTGGLSYKEDTKELVVAKAGVYYVFFQLEL RRVVAGEGSGSVSLALHLQPLRSAAGAAALALTVD LPPASSEARNSAFGFQGRLLHLSAGQRLGVHLHTE ARARHAWQLTQGATVLGLFRVTPEIPAGLPSPRSE GGGGSGGGGSDPAGLLDLRQGMFAQLVAQNVLLID GPLSWYSDPGLAGVSLTGGLSYKEDTKELVVAKAG VYYVFFQLELRRVVAGEGSGSVSLALHLQPLRSAA GAAALALTVDLPPASSEARNSAFGFQGRLLHLSAG QRLGVHLHTEARARHAWQLTQGATVLGLFRVTPEI PAGLPSPRSE |
| 12 | dimeric hu 4-1BBL (52-254) connected by (G4S)2 linker | PWAVSGARASPGSAASPRLREGPELSPDDPAGLLD LRQGMFAQLVAQNVLLIDGPLSWYSDPGLAGVSLT GGLSYKEDTKELVVAKAGVYYVFFQLELRRVVAGE GSGSVSLALHLQPLRSAAGAAALALTVDLPPASSE ARNSAFGFQGRLLHLSAGQRLGVHLHTEARARHAW QLTQGATVLGLFRVTPEIPAGLPSPRSEGGGGSGG GGSPWAVSGARASPGSAASPRLREGPELSPDDPAG LLDLRQGMFAQLVAQNVLLIDGPLSWYSDPGLAGV SLTGGLSYKEDTKELVVAKAGVYYVFFQLELRRVV AGEGSGSVSLALHLQPLRSAAGAAALALTVDLPPA SSEARNSAFGFQGRLLHLSAGQRLGVHLHTEARAR HAWQLTQGATVLGLFRVTPEIPAGLPSPRSE |
| 13 | heavy chain CDR-H1, PD-L1 | DSWIH |
| 14 | heavy chain CDR-H2, PD-L1 | WISPYGGSTYYADSVKG |
| 15 | heavy chain CDR-H3, PD-L1 | RHWPGGFDY |
| 16 | light chain CDR-L1, PD-L1 | RASQDVSTAVA |

TABLE B-continued

| SEQ ID NO: | Description | Sequence |
|---|---|---|
| (Sequences): | | |
| 17 | light chain CDR-L2, PD-L1 | SASFLYS |
| 18 | light chain CDR-L3, PD-L1 | QQYLYHPAT |
| 19 | heavy chain variable domain VH, PD-L1 | EVQLVESGGGLVQPGGSLRLSCAASGFTFSDSWIH WVRQAPGKGLEWVAWISPYGGSTYYADSVKGRFT1 SADTSKNTAYLQMNSLRAEDTAVYYCARRHWPGGF DYWGQGTLVTVSS |
| 20 | light chain variable domain VL, PD-L1 | DIQMTQSPSSLSASVGDRVTITCRASQDVSTAVAW YQQKPGKAPKLLIYSASFLYSGVPSRFSGSGSGTD FTLTISSLQPEDFATYYCQQYLYHPATFGQGTKVE IK |
| 21 | Dimeric 4-1BB ligand (71-248)-CL* Fc knob chain | see Table 1 |
| 22 | Monomeric 4-1BB ligand (71-248)-CH1* | see Table 1 |
| 23 | Dimeric 4-1BB ligand (71-248)-CL Fc knob chain | REGPELSPDDPAGLLDLRQGMFAQLVAQNVLLIDG PLSWYSDPGLAGVSLTGGLSYKEDTKELVVAKAGV YYVFFQLELRRVVAGEGSGSVSLALHLQPLRSAAG AAALALTVDLPPASSEARNSAFGFQGRLLHLSAGQ RLGVHLHTEARARHAWQLTQGATVLGLFRVTPEIP AGLGGGGSGGGGSREGPELSPDDPAGLLDLRQGMF AQLVAQNVLLIDGPLSWYSDPGLAGVSLTGGLSYK EDTKELVVAKAGVYYVFFQLELRRVVAGEGSGSVS LALHLQPLRSAAGAAALALTVDLPPASSEARNSAF GFQGRLLHLSAGQRLGVHLHTEARARHAWQLTQGA TVLGLFRVTPEIPAGLGGGGSGGGGSRTVAAPSVF IFPPSDEQLKSGTASVVCLLNNFYPREAKVQWKVD NALQSGNSQESVTEQDSKDSTYSLSSTLTLSKADY EKHKVYACEVTHQGLSSPVTKSFNRGECDKTHTCP PCPAPEAAGGPSVFLFPPKPKDTLMISRTPEVTCV VVDVSHEDPEVKFNWYVDGVEVHNAKTKPREEQYN STYRVVSVLTVLHQDWLNGKEYKCKVSNKALGAPI EKTISKAKGQPREPQVYTLPPCRDELTKNQVSLWC LVKGFYPSDIAVEWESNGQPENNYKTTPPVLDSDG SFFLYSKLTVDKSRWQQGNVFSCSVMHEALHNHYT QKSLSLSP |
| 24 | Monomeric 4-1BB ligand (71-248)-CH1 | REGPELSPDDPAGLLDLRQGMFAQLVAQNVLLIDG PLSWYSDPGLAGVSLTGGLSYKEDTKELVVAKAGV YYVFFQLELRRVVAGEGSGSVSLALHLQPLRSAAG AAALALTVDLPPASSEARNSAFGFQGRLLHLSAGQ RLGVHLHTEARARHAWQLTQGATVLGLFRVTPEIP AGLGGGGSGGGGSASTKGPSVFPLAPSSKSTSGGT AALGCLVKDYFPEPVTVSWNSGALTSGVHTFPAVL QSSGLYSLSSVVTVPSSSLGTQTYICNVNHKPSNT KVDKKVEPKSC |
| 25 | Dimeric 4-1BB ligand (71-254)-CL* Fc knob chain | REGPELSPDDPAGLLDLRQGMFAQLVAQNVLLIDG PLSWYSDPGLAGVSLTGGLSYKEDTKELVVAKAGV YYVFFQLELRRVVAGEGSGSVSLALHLQPLRSAAG AAALALTVDLPPASSEARNSAFGFQGRLLHLSAGQ RLGVHLHTEARARHAWQLTQGATVLGLFRVTPEIP AGLPSPRSEGGGGSGGGGSREGPELSPDDPAGLLD LRQGMFAQLVAQNVLLIDGPLSWYSDPGLAGVSLT GGLSYKEDTKELVVAKAGVYYVFFQLELRRVVAGE GSGSVSLALHLQPLRSAAGAAALALTVDLPPASSE ARNSAFGFQGRLLHLSAGQRLGVHLHTEARARHAW QLTQGATVLGLFRVTPEIPAGLPSPRSEGGGGSGG GGSRTVAAPSVFIFPPSDRKLKSGTASVVCLLNNF YPREAKVQWKVDNALQSGNSQESVTEQDSKDSTYS LSSTLTLSKADYEKHKVYACEVTHQGLSSPVTKSF NRGECDKTHTCPPCPAPEAAGGPSVFLFPPKPKDT LMISRTPEVTCVVVDVSHEDPEVKFNWYVDGVEVH NAKTKPREEQYNSTYRVVSVLTVLHQDWLNGKEYK CKVSNKALGAPIEKTISKAKGQPREPQVYTLPPCR DELTKNQVSLWCLVKGFYPSDIAVEWESNGQPENN YKTTPPVLDSDGSFFLYSKLTVDKSRWQQGNVFSC SVMHEALHNHYTQKSLSLSP |

TABLE B-continued (Sequences):

| SEQ ID NO: | Description | Sequence |
|---|---|---|
| 26 | Monomeric 4-1BB ligand (71-254)-CH1* | REGPELSPDDPAGLLDLRQGMFAQLVAQNVLLIDG PLSWYSDPGLAGVSLTGGLSYKEDTKELVVAKAGV YYVFFQLELRRVVAGEGSGSVSLALHLQPLRSAAG AAALALTVDLPPASSEARNSAFGFQGRLLHLSAGQ RLGVHLHTEARARHAWQLTQGATVLGLFRVTPEIP AGLPSPRSEGGGGSGGGGSASTKGPSVFPLAPSSK STSGGTAALGCLVEDYFPEPVTVSWNSGALTSGVH TFPAVLQSSGLYSLSSVVTVPSSSLGTQTYICNVN HKPSNTKVDEKVEPKSC |
| 27 | Dimeric 4-1BB ligand (71-254)-CL Fc knob chain | REGPELSPDDPAGLLDLRQGMFAQLVAQNVLLIDG PLSWYSDPGLAGVSLTGGLSYKEDTKELVVAKAGV YYVFFQLELRRVVAGEGSGSVSLALHLQPLRSAAG AAALALTVDLPPASSEARNSAFGFQGRLLHLSAGQ RLGVHLHTEARARHAWQLTQGATVLGLFRVTPEIP AGLPSPRSEGGGGSGGGGSREGPELSPDDPAGLLD LRQGMFAQLVAQNVLLIDGPLSWYSDPGLAGVSLT GGLSYKEDTKELVVAKAGVYYVFFQLELRRVVAGE GSGSVSLALHLQPLRSAAGAAALALTVDLPPASSE ARNSAFGFQGRLLHLSAGQRLGVHLHTEARARHAW QLTQGATVLGLFRVTPEIPAGLPSPRSEGGGGSGG GGSRTVAAPSVFIFPPSDEQLKSGTASVVCLLNNF YPREAKVQWKVDNALQSGNSQESVTEQDSKDSTYS LSSTLTLSKADYEKHKVYACEVTHQGLSSPVTKSF NRGECDKTHTCPPCPAPEAAGGPSVFLFPPKPKDT LMISRTPEVTCVVVDVSHEDPEVKFNWYVDGVEVH NAKTKPREEQYNSTYRVVSVLTVLHQDWLNGKEYK CKVSNKALGAPIEKTISKAKGQPREPQVYTLPPCR DELTKNQVSLWCLVKGFYPSDIAVEWESNGQPENN YKTTPPVLDSDGSFFLYSKLTVDKSRWQQGNVFSC SVMHEALHNHYTQKSLSLSP |
| 28 | Monomeric 4-1BB ligand (71-254) -CH1 | REGPELSPDDPAGLLDLRQGMFAQLVAQNVLLIDG PLSWYSDPGLAGVSLTGGLSYKEDTKELVVAKAGV YYVFFQLELRRVVAGEGSGSVSLALHLQPLRSAAG AAALALTVDLPPASSEARNSAFGFQGRLLHLSAGQ RLGVHLHTEARARHAWQLTQGATVLGLFRVTPEIP AGLPSPRSEGGGGSGGGGSASTKGPSVFPLAPSSK STSGGTAALGCLVKDYFPEPVTVSWNSGALTSGVH TFPAVLQSSGLYSLSSVVTVPSSSLGTQTYICNVN HKPSNTKVDKKVEPKSC |
| 29 | anti-PD-L1 Fc hole chain | EVQLVESGGGLVQPGGSLRLSCAASGFTFSDS WIHWVRQAPGKGLEWVAWISPYGGSTYYADSV KGRFTISADTSKNTAYLQMNSLRAEDTAVYYC ARRHWPGGFDYWGQGTLVTVSSASTKGPSVFP LAPSSKSTSGGTAALGCLVKDYFPEPVTVSWN SGALTSGVHTFPAVLQSSGLYSLSSVVTVPSS SLGTQTYICNVNHKPSNTKVDKKVEPKSCDKT HTCPPCPAPEAAGGPSVFLFPPKPKDTLMISR TPEVTCVVVDVSHEDPEVKFNWYVDGVEVHNA KTKPREEQYNSTYRVVSVLTVLHQDWLNGKEY KCKVSNKALGAPIEKTISKAKGQPREPQVCT LPPSRDELTKNQVSLSCAVKGFYPSDIAVEWE SNGQPENNYKTTPPVLDSDGSFFLVSKLTVDK SRWQQGNVFSCSVMHEALHNHYTQKSLSLSP See Table 1 |
| 30 | anti-PD-L1 light chain | DIQMTQSPSSLSASVGDRVTITCRASQDVSTA VAWYQQKPGKAPKLLIYSASFLYSGVPSRFSG SGSGTDFTLTISSLQPEDFATYYCQQYLYHPA TFGQGTKVEIKRTVAAPSVFIFPPSDEQLKSG TASWCLLNNFYPREAKVQWKVDNALQSGNSQ ESVTEQDSKDSTYSLSSTLTLSKADYEKHKVY ACEVTHQGLSSPVTKSFNRGEC See Table 1 |
| 31 | DP47 Fc hole chain | EVQLLESGGGLVQPGGSLRLSCAASGFTFSSY AMSWVRQAPGKGLEWVSAISGSGGSTYYADSV KGRFTISRDNSKNTLYLQMNSLRAEDTAVYYC AKGSGFDYWGQGTLVTVSSASTKGPSVFPLAP SSKSTSGGTAALGCLVKDYFPEPVTVSWNSGA LTSGVHTFPAVLQSSGLYSLSSVVTVPSSSLG TQTYICNVNHKPSNTKVDKKVEPKSCDKTHTC PPCPAPEAAGGPSVFLFPPKPKDTLMISRTPE |

TABLE B-continued

| SEQ ID NO: | Description | Sequence |
|---|---|---|
| (Sequences): | | |
| | | VTCVVVDVSHEDPEVKFNWYVDGVEVHNAKTK PREEQYNSTYRVVSVLTVLHQDWLNGKEYKCK VSNKALGAPIEKTISKAKGQPREPQVCTLPPS RDELTKNQVSLSCAVKGFYPSDIAVEWESNGQ PENNYKTTPPVLDSDGSFFLVSKLTVDKSRWQ QGNVFSCSVMHEALHNHYTQKSLSLSP See Table 2 |
| 32 | DP47 light chain | EIVLTQSPGTLSLSPGERATLSCRASQSVSSS YLAWYQQKPGQAPRLLIYGASSRATGIPDRFS GSGSGTDFTLTISRLEPEDFAVYYCQQYGSSP LTFGQGTKVEIKRTVAAPSVFIFPPSDEQLKS GTASVVCLLNNFYPREAKVQWKVDNALQSGNS QESVTEQDSKDSTYSLSSTLTLSKADYEKHKV YACEVTHQGLSSPVTKSFNRGEC See Table 2 |
| 33 | human 4-1BB ECD, aa 24-186 of Q07011 | LQDPCSNCPAGTFCDNNRNQICSPCPPNSFSSAGG QRTCDICRQCKGVFRTRKECSSTSNAECDCTPGFH CLGAGCSMCEQDCKQGQELTKKGCKDCCFGTFNDQ KRGICRPWTNCSLDGKSVLVNGTKERDVVCGPSPA DLSPGASSVTPPAPAREPGHSPQ |
| 34 | Fc hole chain | DKTHTCPPCPAPELLGGPSVFLFPPKPKDTLM 1SRTPEVTCVVVDVSHEDPEVKFNWYVDGVEV HNAKTKPREEQYNSTYRVVSVLTVLHQDWLNG KEYKCKVSNKALPAPIEKTISKAKGQPREPQV CTLPPSRDELTKNQVSLSCAVKGFYPSDIAVE WESNGQPENNYKTTPPVLDSDGSFFLVSKLTV DKSRWQQGNVFSCSVMHEALHNHYTQKSLSLS P See Table 4 |
| 35 | human 4-1BB antigen Fc knob chain | LQDPCSNCPAGTFCDNNRNQICSPCPPNSFSS AGGQRTCDICRQCKGVFRTRKECSSTSNAECD CTPGFHCLGAGCSMCEQDCKQGQELTKKGCKD CCFGTFNDQKRGICRPWTNCSLDGKSVLVNGT KERDVVCGPSPADLSPGASSVTPPAPAREPGH SPQVDEQLYFQGGSPKSADKTHTCPPCPAPEL LGGPSVFLFPPKPKDTLMISRTPEVTCVVVDV SHEDPEVKFNWYVDGVEVHNAKTKPREEQYNS TYRVVSVLTVLHQDWLNGKEYKCKVSNKALPA PIEKTISKAKGQPREPQVYTLPPCRDELTKNQ VSLWCLVKGFYPSDIAVEWESNGQPENNYKTT PPVLDSDGSFFLYSKLTVDKSRWQQGNVFSCS VMHEALHNHYTQKSLSLSPGKSGGLNDIFEAQ KIEWHE See Table 4 |
| 36 | (G4S)2 peptide linker | GGGGSGGGGS |
| 37 | Human PD-L1 | UniProt no. Q9NZQ7 MRIFAVFIFM TYWHLLNAFT VTVPKDLYW EYGSNMTIEC KFPVEKQLDL AALIVYWEME DKNIIQFVHG EEDLKVQHSS YRQRARLLKD QLSLGNAALQ ITDVKLQDAG VYRCMISYGG ADYKRITVKV NAPYNKINQR ILWDPVTSE HELTCQAEGY PKAEVIWTSS DHQVLSGKTT TTNSKREEKL FNVTSTLRIN TTTNEIFYCT FRRLDPEENH TAELVIPELP LAHPPNERTH LVILGAILLC LGVALTFIFR LRKGRMMDVK KCGIQDTNSK KQSDTHLEET |
| 38 | human 4-1BBL | UniProt no. P41273 MEYASDASLD PEAPWPPAPR ARACRVLPWA LVAGLLLLLL LAAACAVFLA CPWAVSGARA SPGSAASPRL REGPELSPDD PAGLLDLRQG MFAQLVAQNV LLIDGPLSWY SDPGLAGVSL TGGLSYKEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE |

TABLE B-continued (Sequences):

| SEQ ID NO: | Description | Sequence |
|---|---|---|
| 39 | human 4-1BBL(50-254) | ACPWAVSGARASPGSAASPRLREGPELSPDDPAGL LDLRQGMFAQLVAQNVLLIDGPLSWYSDPGLAGVS LTGGLSYKEDTKELVVAKAGVYYVFFQLELRRVVA GEGSGSVSLALHLQPLRSAAGAAALALTVDLPPAS SEARNSAFGFQGRLLHLSAGQRLGVHLHTEARARH AWQLTQGATVLGLFRVTPEIPAGLPSPRSE |
| 40 | Peptide linker G4S | GGGGS |
| 41 | Peptide linker $(SG4)_2$ | SGGGGSGGGG |
| 42 | Peptide linker $(G4S)_3$ | GGGGSGGGGSGGGGS |
| 43 | Peptide linker $G4(SG4)_2$ | GGGGSGGGGSGGGG |
| 44 | Peptide linker $(G4S)_4$ | GGGGSGGGGSGGGGSGGGGS |
| 45 | Peptide linker | GSPGSSSSGS |
| 46 | Peptide linker | GSGSGSGS |
| 47 | Peptide linker | GSGSGNGS |
| 48 | Peptide linker | GGSGSGSG |
| 49 | Peptide linker | GGSGSG |
| 50 | Peptide linker | GGSG |
| 51 | Peptide linker | GGSGNGSG |
| 52 | Peptide linker | GGNGSGSG |
| 53 | Peptide linker | GGNGSG |
| 54 | VHCH1(EE) (20H4.9)-Heavy chain HC1 (Fc hole) | QVQLQQWGAGLLKPSETLSLTCAVYGGSFSGYYWS WIRQSPEKGLEWIGEINHGGYVTYNPSLESRVTIS VDTSKNQFSLKLSSVTAADTAVYYCARDYGPGNYD WYFDLWGRGTLVTVSSASTKGPSVFPLAPSSKSTS GGTAALGCLVEDYFPEPVTVSWNSGALTSGVHTFP AVLQSSGLYSLSSVVTVPSSSLGTQTYICNVNHKP SNTKVDEKVEPKSCDKTHTCPPCPAPEAAGGPSVF LFPPKPKDTLMISRTPEVTCVVVDVSHEDPEVKFN WYVDGVEVHNAKTKPREEQYNSTYRVVSVLTVLHQ DWLNGKEYKCKVSNKALGAPIEKTISKAKGQPREP QVCTLPPSRDELTKNQVSLSCAVKGFYPSDIAVEW ESNGQPENNYKTTPPVLDSDGSFFLVSKLTVDKSR WQQGNVFSCSVMHEALHNHYTQKSLSLSP |
| 55 | VLCH1 (PD-L1) VHCH1(EE) (20H4.9)-Heavy chain HC2 (Fc knob) | DIQMTQSPSSLSASVGDRVTITCRASQDVSTAVAW YQQKPGKAPKLLIYSASFLYSGVPSRFSGSGSGTD FTLTISSLQPEDFATYYCQQYLYHPATFGQGTKVE IKSSASTKGPSVFPLAPSSKSTSGGTAALGCLVKD YFPEPVTVSWNSGALTSGVHTFPAVLQSSGLYSLS SVVTVPSSSLGTQTYICNVNHKPSNTKVDKKVEPK SCDGGGGSGGGGSQVQLQQWGAGLLKPSETLSLTC AVYGGSFSGYYWSWIRQSPEKGLEWIGEINHGGYV TYNPSLESRVTISVDTSKNQFSLKLSSVTAADTAV YYCARDYGPGNYDWYFDLWGRGTLVTVSSASTKGP SVFPLAPSSKSTSGGTAALGCLVEDYFPEPVTVSW NSGALTSGVHTFPAVLQSSGLYSLSSVVTVPSSSL GTQTYICNVNHKPSNTKVDEKVEPKSCDKTHTCPP CPAPEAAGGPSVFLFPPKPKDTLMISRTPEVTCVV VDVSHEDPEVKFNWYVDGVEVHNAKTKPREEQYNS TYRVVSVLTVLHQDWLNGKEYKCKVSNKALGAPIE KTISKAKGQPREPQVYTLPPCRDELTKNQVSLWCL VKGFYPSDIAVEWESNGQPENNYKTTPPVLDSDGS FFLYSKLTVDKSRWQQGNVFSCSVMHEALHNHYTQ KSLSLSP |
| 56 | VLCL(RK)-Light chain (20H4.9) | EIVLTQSPATLSLSPGERATLSCRASQSVSSYLAW YQQKPGQAPRLLIYDASNRATGIPARFSGSGSGTD FTLTISSLEPEDFAVYYCQQRSNWPPALTFGGGTK VEIKRTVAAPSVFIFPPSDRKLKSGTASVVCLLNN FYPREAKVQWKVDNALQSGNSQESVTEQDSKDSTY |

TABLE B-continued (Sequences):

| SEQ ID NO: | Description | Sequence |
|---|---|---|
| | | SLSSTLTLSKADYEKHKVYACEVTHQGLSSPVTKS<br>FNRGEC |
| 57 | VHCL-Light chain (PD-L1) | EVQLVESGGGLVQPGGSLRLSCAASGFTFSDSWIH<br>WVRQAPGKGLEWVAWISPYGGSTYYADSVKGRFT1<br>SADTSKNTAYLQMNSLRAEDTAVYYCARRHWPGGF<br>DYWGQGTLVTVSSASVAAPSVFIFPPSDEQLKSGT<br>ASWCLLNNFYPREAKVQWKVDNALQSGNSQESVT<br>EQDSKDSTYSLSSTLTLSKADYEKHKVYACEVTHQ<br>GLSSPVTKSFNRGEC |
| 58 | VLCH1 (PD-L1)-Heavy chain HC2 (Fc knob) | DIQMTQSPSSLSASVGDRVTITCRASQDVSTAVAW<br>YQQKPGKAPKLLIYSASFLYSGVPSRFSGSGSGTD<br>FTLTISSLQPEDFATYYCQQYLYHPATFGQGTKVE<br>IKSSASTKGPSVFPLAPSSKSTSGGTAALGCLVKD<br>YFPEPVTVSWNSGALTSGVHTFPAVLQSSGLYSLS<br>SVVTVPSSSLGTQTYICNVNHKPSNTKVDKKVEPK<br>SCDKTHTCPPCPAPEAAGGPSVFLFPPKPKDTLMI<br>SRTPEVTCVVVDVSHEDPEVKFNWYVDGVEVHNAK<br>TKPREEQYNSTYRVVSVLTVLHQDWLNGKEYKCKV<br>SNKALGAPIEKTISKAKGQPREPQVYTLPPCRDEL<br>TKNQVSLWCLVKGFYPSDIAVEWESNGQPENNYKT<br>TPPVLDSDGSFFLYSKLTVDKSRWQQGNVFSCSVM<br>HEALHNHYTQKSLSLSP |
| 59 | Human CD3ϵ | Uniprot No. P07766<br>MQSGTHWRVL GLCLLSVGVW GQDGNEEMGG<br>ITQTPYKVSI SGTTVILTCP QYPGSEILWQ<br>HNDKNIGGDE DDKNIGSDED HLSLKEFSEL<br>EQSGYYVCYP RGSKPEDANF YLYLRARVCE<br>NCMEMDVMSV ATIVIVDICI TGGLLLLVYY<br>WSKNRKAKAK PVTRGAGAGG RQRGQNKERP<br>PPVPNPDYEP IRKGQRDLYS GLNQRRI |
| 60 | Cynomolgus CD3ϵ | Uniprot No. Q95LI5<br>MQSGTRWRVL GLCLLSIGVW GQDGNEEMGS<br>ITQTPYQVSI SGTTVILTCS QHLGSEAQWQ<br>HNGKNKEDSG DRLFLPEFSE MEQSGYYVCY<br>PRGSNPEDAS HHLYLKARVC ENCMEMDVMA<br>VATIVIVDIC ITLGLLLLVY YWSKNRKAKA<br>KPVTRGAGAG GRQRGQNKER PPPVPNPDYE<br>PIRKGQQDLY SGLNQRRI |

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, MD (1991). Amino acids of antibody chains are numbered and referred to according to the EU numbering systems according to Kabat (Kabat, E. A., et al., Sequences of Proteins of Immunological Interest, 5th ed., Public Health Service, National Institutes of Health, Bethesda, MD (1991)) as defined above.

EXAMPLES

The following are examples of methods and compositions of the invention. It is understood that various other embodiments may be practiced, given the general description provided above.

Recombinant DNA Techniques

Standard methods were used to manipulate DNA as described in Sambrook et al., Molecular cloning: A laboratory manual; Cold Spring Harbor Laboratory Press, Cold Spring Harbor, New York, 1989. The molecular biological reagents were used according to the manufacturer's instructions. General information regarding the nucleotide sequences of human immunoglobulin light and heavy chains is given in: Kabat, E. A. et al., (1991) Sequences of Proteins of Immunological Interest, Fifth Ed., NIH Publication No 91-3242.

DNA Sequencing

DNA sequences were determined by double strand sequencing.

Gene Synthesis

Desired gene segments were either generated by PCR using appropriate templates or were synthesized by Geneart AG (Regensburg, Germany) from synthetic oligonucleotides and PCR products by automated gene synthesis. In cases where no exact gene sequence was available, oligonucleotide primers were designed based on sequences from closest homologues and the genes were isolated by RT-PCR from RNA originating from the appropriate tissue. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells.

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Protein Purification

Proteins were purified from filtered cell culture supernatants referring to standard protocols. In brief, antibodies were applied to a Protein A Sepharose column (GE healthcare) and washed with PBS. Elution of antibodies was achieved at pH 2.8 followed by immediate neutralization of the sample. Aggregated protein was separated from monomeric antibodies by size exclusion chromatography (Superdex 200, GE Healthcare) in PBS or in 20 mM Histidine, 150 mM NaCl pH 6.0. Monomeric antibody fractions were pooled, concentrated (if required) using e.g., a MILLIPORE Amicon Ultra (30 MWCO) centrifugal concentrator, frozen and stored at −20° C. or −80° C. Part of the samples were provided for subsequent protein analytics and analytical characterization e.g. by SDS-PAGE, size exclusion chromatography (SEC) or mass spectrometry.

SDS-PAGE

The NuPAGE® Pre-Cast gel system (Invitrogen) was used according to the manufacturer's instruction. In particular, 10% or 4-12% NuPAGE® Novex® Bis-TRIS Pre-Cast gels (pH 6.4) and a NuPAGE® MES (reduced gels, with NuPAGE® Antioxidant running buffer additive) or MOPS (non-reduced gels) running buffer was used.

Analytical Size Exclusion Chromatography

Size exclusion chromatography (SEC) for the determination of the aggregation and oligomeric state of antibodies was performed by HPLC chromatography. Briefly, Protein A purified antibodies were applied to a Tosoh TSKgel G3000SW column in 300 mM NaCl, 50 mM $KH_2PO_4$/$K_2HPO_4$, pH 7.5 on an Agilent HPLC 1100 system or to a Superdex 200 column (GE Healthcare) in 2×PBS on a Dionex HPLC-System. The eluted protein was quantified by UV absorbance and integration of peak areas. BioRad Gel Filtration Standard 151-1901 served as a standard.

Example 1

Generation and Production of PD-L1 Targeting 4-1BB Ligand Trimer-Containing Antigen Binding Molecules 1.1. Generation and Production of PD-L1 Targeting 4-1BB Ligand Trimer-Containing Antigen Binding Molecules The variable region of heavy and light chain DNA sequences encoding an antigen binding domain specific for PD-L1, were subcloned in frame with either the constant heavy chain of the hole or the constant light chain of human IgG1.

The DNA sequence encoding part of the ectodomain (amino acid 71-248) of human 4-1BB ligand was synthetized according to the P41273 sequence of Uniprot database.

A polypeptide containing two ectodomains of 4-1BB ligand, separated by (G4S)2 linkers, and fused to the human IgG1-CL domain, was cloned as depicted in FIG. 1A: human 4-1BB ligand, (G4S)2 connector, human 4-1BB ligand, (G4S)2 connector, human CL.

Figure 1B:
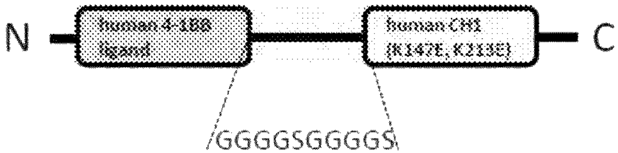

A polypeptide containing one ectodomain of 4-1BB ligand and fused to the human IgG1-CH domain, was cloned as described in FIG. 1B: human 4-1BB ligand, (G4S)2 connector, human CH.

To improve correct pairing the following mutations were introduced in the crossed CH-CL. In the human CL domain fused to dimeric 4-1BB ligand the mutations E123R and Q124K were introduced. In the human CH1 domain fused to monomeric 4-1BB ligand the mutations K147E and K213E were cloned as described in International Patent Appl. Publ. No. WO 2015/150447.

The variable region of heavy and light chain DNA sequences encoding the antigen binding domain capable of specific binding to PD-L1 were subcloned in frame with either the constant heavy chain of the hole or the constant light chain of human IgG1. The anti-PD-L1 clone (clone YW243.55.S70) is disclosed in WO 2010/077634.

In the Fc domain the P329G, L234A and L235A mutations were introduced in the constant region of the knob and hole heavy chains to abrogate binding to Fc gamma receptors according to the method described in International Patent Appl. Publ. No. WO 2012/130831. Combination of the dimeric ligand-Fc knob chain containing the S354C/T366W mutations, the monomeric CH1 fusion, the targeted anti-PD-L1 Fc hole chain containing the Y349CfT366S/L368A/Y407V mutations and the anti-PD-L1 light chain allowed the generation of a heterodimer, which includes an assembled trimeric 4-1BB ligand and a PD-L1 binding Fab (FIG. 2).

Table 1 shows the amino acid sequences of the monovalent anti-PD-L1 split trimeric 4-1BB ligand Fc (kih) fusion antigen binding molecule containing CH1-CL crossover and charged residues in the CH1 and CL domain fused to 4-1BBL. The molecule is called PD-L1-4-1BBL.

TABLE 1

Amino acid sequences of PD-L1-4-1BBL containing CH1-CL crossover and charged residues (*for charged residues)

| SEQ ID NO: | Description | Sequences |
|---|---|---|
| 21 | Dimeric hu 4-1BBL (71-248)-CL* Fc knob chain | REGPELSPDDPAGLLDLRQGMF AQLVAQNVLLIDGPLSWYSDPG LAGVSLTGGLSYKEDTKELVVA KAGVYYVFFQLELRRVVAGEGS GSVSLALHLQPLRSAAGAAALA LTVDLPPASSEARNSAFGFQGR LLHLSAGQRLGVHLHTEARARH AWQLTQGATVLGLFRVTPEIPA GLGGGGSGGGGSREGPELSPDD PAGLLDLRQGMFAQLVAQNVLL IDGPLSWYSDPGLAGVSLTGGL SYKEDTKELVVAKAGVYYVFFQ LELRRVVAGEGSGSVSLALHLQ PLRSAAGAAALALTVDLPPASS EARNSAFGFQGRLLHLSAGQRL GVHLHTEARARHAWQLTQGATV LGLFRVTPEIPAGLGGGGSGGG GSRTVAAPSVFIFPPSDRKLKS GTASVVCLLNNFYPREAKVQWK VDNALQSGNSQESVTEQDSKDS TYSLSSTLTLSKADYEKHKVYA CEVTHQGLSSPVTKSFNRGECD KTHTCPPCPAPEAAGGPSVFLF PPKPKDTLMISRTPEVTCVVVD VSHEDPEVKFNWYVDGVEVHNA KTKPREEQYNSTYRVVSVLTVL HQDWLNGKEYKCKVSNKALGAP IEKTISKAKGQPREPQVYTLPP CRDELTKNQVSLWCLVKGFYPS DIAVEWESNGQPENNYKTTPPV LDSDGSFFLYSKLTVDKSRWQQ GNVFSCSVMHEALHNHYTQKSL SLSP |

TABLE 1-continued

Amino acid sequences of PD-L1-4-1BBL containing CH1-CL crossover and charged residues (*for charged residues)

| SEQ ID NO: | Description | Sequences |
|---|---|---|
| 22 | Monomeric hu 4-1BBL (71-248)-CH1* | REGPELSPDDPAGLLDLRQGMF AQLVAQNVLLIDGPLSWYSDPG LAGVSLTGGLSYKEDTKELVVA KAGVYYVFFQLELRRVVAGEGS GSVSLALHLQPLRSAAGAAALA LTVDLPPASSEARNSAFGFQGR LLHLSAGQRLGVHLHTEARARH AWQLTQGATVLGLFRVTPEIPA GLGGGGSGGGGSASTKGPSVFP LAPSSKSTSGGTAALGCLVEDY FPEPVTVSWNSGALTSGVHTFP AVLQSSGLYSLSSVVTVPSSSL GTQTYICNVNHKPSNTKVDEKV EPKSC |
| 29 | anti-PD-L1 Fc hole chain | EVQLVESGGGLVQPGGSLRLSC AASGFTFSDSWIHWVRQAPGKG LEWVAWISPYGGSTYYADSVKG RFTISADTSKNTAYLQMNSLRA EDTAVYYCARRHWPGGFDYWGQ GTLVTVSSASTKGPSVFPLAPS SKSTSGGTAALGCLVKDYFPEP VTVSWNSGALTSGVHTFPAVLQ SSGLYSLSSVVTVPSSSLGTQT YICNVNHKPSNTKVDKKVEPKS CDKTHTCPPCPAPEAAGGPSVF LFPPKPKDTLMISRTPEVTCVV VDVSHEDPEVKFNWYVDGVEVH NAKTKPREEQYNSTYRVVSVLT VLHQDWLNGKEYKCKVSNKALG APIEKTISKAKGQPREPQVCT LPPSRDELTKNQVSLSCAVKGF YPSDIAVEWESNGQPENNYKTT PPVLDSDGSFFLVSKLTVDKSR WQQGNVFSCSVMHEALHNHYTQ KSLSLSP |
| 30 | anti-PD-L1 light chain | DIQMTQSPSSLSASVGDRVTIT CRASQDVSTAVAWYQQKPGKAP KLLIYSASFLYSGVPSRFSGSG SGTDFTLTISSLQPEDFATYYC QQYLYHPATFGQGTKVEIKRTV AAPSVFIFPPSDEQLKSGTASV VCLLNNFYPREAKVQWKVDNAL QSGNSQESVTEQDSKDSTYSLS STLTLSKADYEKHKVYACEVTH QGLSSPVTKSFNRGEC |

Table 2 shows the amino acid sequences of an untargeted control molecule DP47 split trimeric 4-1BB ligand Fc (kih) fusion antigen binding molecule.

TABLE 2

Amino acid sequences of DP47-4-1BBL containing CH1-CL crossover and charged residues (*for charged residues)

| SEQ ID NO: | Description | Sequences |
|---|---|---|
| 21 | Dimeric hu 4-1BBL (71-248)-CL* Fc knob chain | see Table 1 |
| 22 | Monomeric hu 4-1BBL (71-248)-CH1* | see Table 1 |

TABLE 2-continued

Amino acid sequences of DP47-4-1BBL containing CH1-CL crossover and charged residues (*for charged residues)

| SEQ ID NO: | Description | Sequences |
|---|---|---|
| 31 | DP47 Fc hole chain | EVQLLESGGGLVQPGGSLRLSC AASGFTFSSYAMSWVRQAPGKG LEWVSAISGSGGSTYYADSVKG RFTISRDNSKNTLYLQMNSLRA EDTAVYYCAKGSGFDYWGQGTL VTVSSASTKGPSVFPLAPSSKS TSGGTAALGCLVKDYFPEPVTV SWNSGALTSGVHTFPAVLQSSG LYSLSSVVTVPSSSLGTQTYIC NVNHKPSNTKVDKKVEPKSCDK THTCPPCPAPEAAGGPSVFLFP PKPKDTLMISRTPEVTCVVVDV SHEDPEVKFNWYVDGVEVHNAK TKPREEQYNSTYRVVSVLTVLH QDWLNGKEYKCKVSNKALGAPI EKTISKAKGQPREPQVCTLPPS RDELTKNQVSLSCAVKGFYPSD IAVEWESNGQPENNYKTTPPVL DSDGSFFLVSKLTVDKSRWQQG NVFSCSVMHEALHNHYTQKSLS LSP |
| 32 | DP47 light chain | EIVLTQSPGTLSLSPGERATLS CRASQSVSSSYLAWYQQKPGQA PRLLIYGASSRATGIPDRFSGS GSGTDFTLTISRLEPEDFAVYY CQQYGSSPLTFGQGTKVEIKRT VAAPSVFIFPPSDEQLKSGTAS VVCLLNNFYPREAKVQWKVDNA LQSGNSQESVTEQDSKDSTYSL SSTLTLSKADYEKHKVYACEVT HQGLSSPVTKSFNRGEC |

The bispecific constructs were produced by co-transfecting HEK293-EBNA cells with the mammalian expression vectors using polyethylenimine. The cells were transfected with the corresponding expression vectors in a 1:1:1:1 ("vector 4-1BBL Fc-knob chain":"vector 4-1BBL light chain":"vector Fc-hole chain":"vector light chain").

Production was performed in shake flasks using HEK293 EBNA cells. Antibodies and bispecific antibodies were generated by transient transfection of HEK293 EBNA cells or CHO EBNA cells. Cells were centrifuged and, medium was replaced by pre-warmed CD CHO medium (Thermo Fisher, Cat N° 10743029). Expression vectors were mixed in CD CHO medium, PEI (Polyethylenimine, Polysciences, Inc, Cat N° 23966-1) was added, the solution vortexed and incubated for 10 minutes at room temperature. Afterwards, cells (2 Mio/ml) were mixed with the vector/PEI solution, transferred to a flask and incubated for 3 hours at 37° C. in a shaking incubator with a 5% $CO_2$ atmosphere. After the incubation, Excell medium with supplements (80% of total volume) was added (W. Zhou and A. Kantardjieff, Mammalian Cell Cultures for Biologics Manufacturing, DOI: 10.1007/978-3-642-54050-9; 2014). One day after transfection, supplements (Feed, 12% of total volume) were added. Cell supernatants were harvested after 7 days by centrifugation and subsequent filtration (0.2 μm filter), and proteins were purified from the harvested supernatant by standard methods as indicated below.

Proteins were purified from filtered cell culture supernatants referring to standard protocols. In brief, Fc containing proteins were purified from cell culture supernatants by Protein A-affinity chromatography (equilibration buffer: 20 mM sodium citrate, 20 mM sodium phosphate, pH 7.5;

elution buffer: 20 mM sodium citrate, pH 3.0). Elution was achieved at pH 3.0 followed by immediate pH neutralization of the sample. The protein was concentrated by centrifugation (Millipore Amicon® ULTRA-15 (Art.Nr.: UFC903096), and aggregated protein was separated from monomeric protein by size exclusion chromatography in 20 mM histidine, 140 mM sodium chloride, pH 6.0.

The concentrations of purified proteins were determined by measuring the absorption at 280 nm using the mass extinction coefficient calculated on the basis of the amino acid sequence according to Pace, et al., Protein Science, 1995, 4, 2411-1423. Purity and molecular weight of the proteins were analyzed by CE-SDS in the presence and absence of a reducing agent using a LabChipGXII (Perkin Elmer). Determination of the aggregate content was performed by HPLC chromatography at 25° C. using analytical size-exclusion column (TSKgel G3000 SW XL or UP-SW3000) equilibrated in running buffer (25 mM $K_2HPO_4$, 125 mM NaCl, 200 mM L-Arginine Monohydrocloride, pH 6.7 or 200 mM KH2PO4, 250 mM KCl pH 6.2, respectively).

Table 3 summarizes the yield and final monomer content of the PD-L1 targeting 4-1BB ligand trimer-containing antigen binding molecules.

TABLE 3

Biochemical analysis of PD-L1 targeting 4-1BB ligand trimer-containing antigen binding molecules

| Molecule | Monomer [%] (SEC) | Yield [mg/l] | CE-SDS (non-red) |
|---|---|---|---|
| PD-L1 4-1-BBL | 98 | 13 | 93 |

1.2. Generation and Production of Bispecific Antibodies with a Bivalent Binding to 4-1BB and a Monovalent Binding to PD-L1

For comparison, bispecific agonistic 4-1BB antibodies with bivalent or monovalent binding to 4-1BB and monovalent binding to PD-L1 have also been prepared.

A bispecific agonistic 4-1BB×PD-L1 antibody with bivalent binding to 4-1BB and monovalent binding to PD-L1 has been produced in the so-termed Head to Head (H2H) 2+1 format as described in WO 2020/007817 A1.

Figures 2A, 2B, 2C:
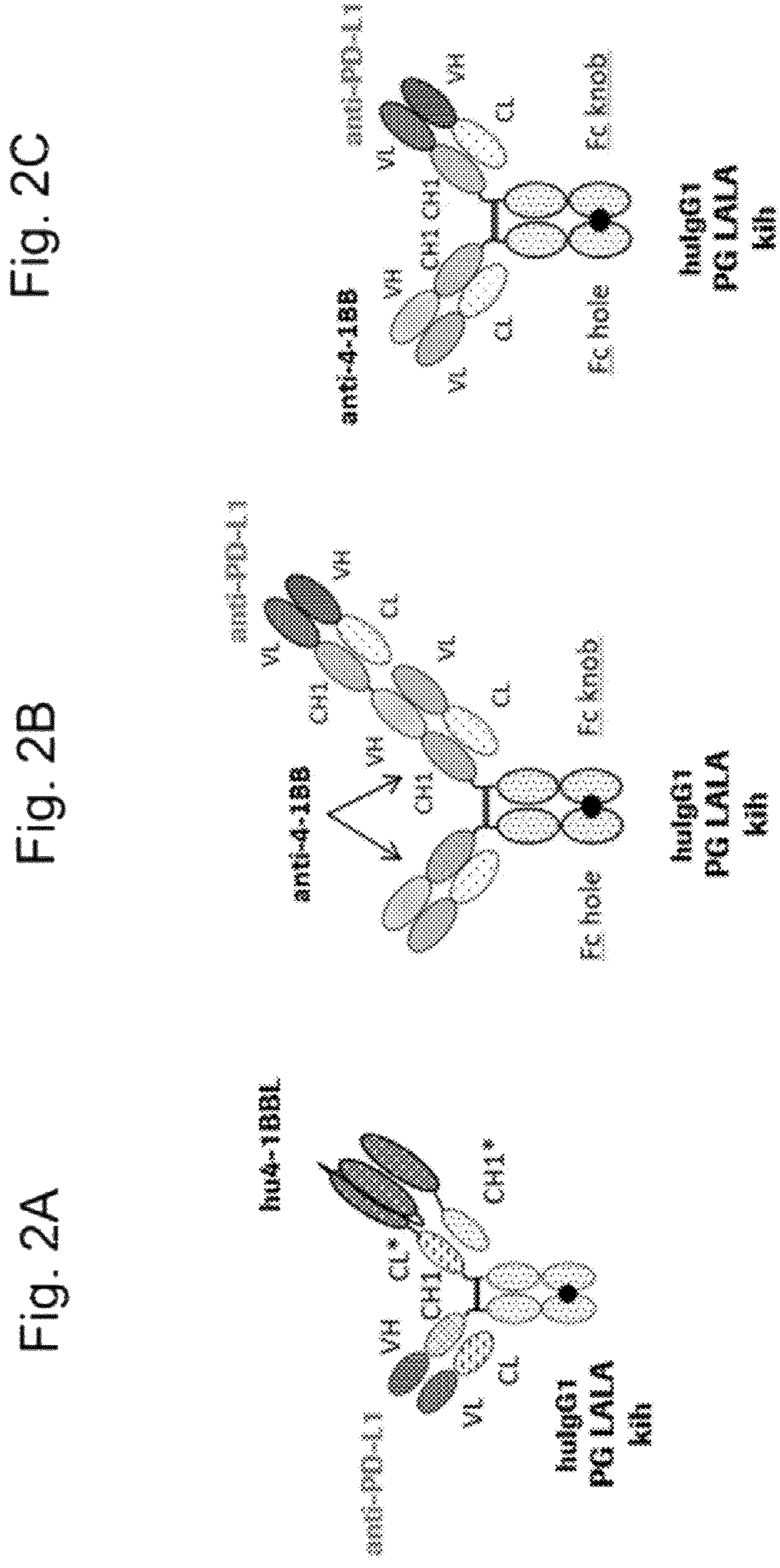
FIG. 2A illustrates schematically the structure of the monovalent PD-L1 targeting split trimeric 4-1BB ligand Fc (kih) fusion antigen binding molecule comprising CH-CL cross with charged residues. The thick black point stands for the knob-into-hole modification. * symbolizes amino acid modifications in the CH1 and CL domain (so-called charged variant). The molecule is named PD-L1-4-1BBL.
FIG. 2B illustrates schematically the structure of the monovalent PD-L1 and bivalent 4-1BB (clone 20H4.9) targeting molecule, called further 2+1 format. The thick black point stands for the knob-into-hole modification. The molecule is named 4-1BB×PD-L1 2+1.
FIG. 2C illustrates schematically the structure of the monovalent PD-L1 and 4-1BB (clone 20H4.9) targeting molecule, called further 1+1 format. The thick black point stands for the knob-into-hole modification. This molecule is thus named 4-1BB×PD-L1 1+1.

The first heavy chain HC1 of the construct is comprised of the following components: VHCH1 of anti-4-1BB binder (clone 20H4.9), followed by Fc hole. The second heavy chain HC2 was comprised of VLCH1 of anti-PD-L1 binder (clone YW243.55.S70 in cross Fab format) followed by VHCH1 of an anti-4-1BB (clone 20H4.9) and by Fc knob. PD-L1 binder YW243.55.S70 is described in WO 2010/077634. For the 4-1BB binder, the VH and VL sequences of clone 20H4.9 were obtained in accordance with U.S. Pat. No. 7,288,638 B2 or U.S. Pat. No. 7,659,384 B2. Combination of the two heavy chains allows generation of a heterodimer, which includes a PD-L1 binding cross Fab and two 4-1BB binding Fabs (FIG. 2B). Another heterodimer with monovalent binding to 4-1BB was construed from a first heavy chain HCl comprising VHCH1 of anti-4-1BB binder (clone 20H4.9) followed by Fc hole and a second heavy chain HC2 comprising VLCH1 of anti-PD-L1 binder (clone YW243.55.S70 in cross Fab format) followed by Fc knob (FIG. 2C).

To improve correct pairing, the following mutations were introduced in the CH-CL of the anti-4-1BB Fab molecules: E123R and Q124K in CL and K147E and K213E in CH1. The second light chain LC2 of the anti-PD-L1 binder is composed of VHCL (cross Fab). The knobs into hole technology was applied by introducing the Y349C/T366S/L368A/Y407V mutations in the first heavy chain HC1 (Fc hole heavy chain) and by introducing the S354C/T366W mutations in the second heavy chain HC2 (Fc knob heavy chain) to allow generation of a heterodimer.

Furthermore, the Pro329Gly, Leu234Ala and Leu235Ala mutations have been introduced in the constant region of the knob and hole heavy chains to abrogate binding to Fc gamma receptors according to the method described in International Patent Appl. Publ. No. WO2012/130831A1.

The 4-1BB×PD-L1 antibody in the 2+1 format comprises a heavy chain comprising the amino acid sequence of SEQ ID NO: 54, a heavy chain comprising the amino acid sequence of SEQ ID NO:55, two light chains each comprising the amino acid sequence of SEQ ID NO:56 and a light chain comprising the amino acid sequence of SEQ ID NO:57.

The 4-1BB×PD-L1 antibody in the 1+1 format comprises a heavy chain comprising the amino acid sequence of SEQ ID NO: 54, a heavy chain comprising the amino acid sequence of SEQ ID NO:58, a light chain comprising the amino acid sequence of SEQ ID NO:56 and a light chain comprising the amino acid sequence of SEQ ID NO:57.

Example 2

Functional Characterization of PD-L1 Targeting 4-1BB Ligand Trimer-Containing Antigen Binding Molecules by Surface Plasmon Resonance Preparation of 4-1BB Fc (Kih) Fusion Molecule A DNA sequence encoding the ectodomain of human 4-1BB (amino acids 24 to 186 of human 4-1BB according to Q07011, SEQ ID NO:33) were subcloned in frame with the human IgG1 heavy chain CH2 and CH3 domains on the knob. An AcTEV protease cleavage site was introduced between an antigen ectodomain and the Fc of human IgG1. An Avi tag for directed biotinylation was introduced at the C-terminus of the antigen-Fc knob. Combination of the antigen-Fc knob chain containing the S354C/T366W mutations, with a Fc hole chain containing the Y349C/T366S/L368A/Y407V mutations allows generation of a heterodimer which includes a single copy of 4-1BB ectodomain containing chain, thus creating a monomeric form of Fc-linked antigen. Table 5 shows the amino acid sequences of the antigen Fc-fusion construct.

TABLE 4

Amino acid sequences of monomeric human 4-1BB Fc(kih) fusion molecule

| SEQ ID NO: | Antigen | Sequence |
|---|---|---|
| 34 | Fc hole chain | DKTHTCPPCPAPELLGGPSVFL FPPKPKDTLMISRTPEVTCVVV DVSHEDPEVKFNWYVDGVEVHN AKTKPREEQYNSTYRVVSVLTV LHQDWLNGKEYKCKVSNKALPA PIEKTISKAKGQPREPQVCTLP PSRDELTKNQVSLSCAVKGFYP SDIAVEWESNGQPENNYKTTPP VLDSDGSFFLVSKLTVDKSRWQ QGNVFSCSVMHEALHNHYTQKS LSLSP |

TABLE 4-continued

Amino acid sequences of monomeric human 4-1BB Fc(kih) fusion molecule

| SEQ ID NO: | Antigen | Sequence |
|---|---|---|
| 35 | human 4-1BB antigen Fc knob chain | LQDPCSNCPAGTFCDNNRNQIC SPCPPNSFSSAGGQRTCDICRQ CKGVFRTRKECSSTSNAECDCT PGFHCLGAGCSMCEQDCKQGQE LTKKGCKDCCFGTFNDQKRGIC RPWTNCSLDGKSVLVNGTKERD VVCGPSPADLSPGASSVTPPAP AREPGHSPQVDEQLYFQGGSPK SADKTHTCPPCPAPELLGGPSV FLFPPKPKDTLMISRTPEVTCV VVDVSHEDPEVKFNWYVDGVEV HNAKTKPREEQYNSTYRVVSVL TVLHQDWLNGKEYKCKVSNKAL PAPIEKTISKAKGQPREPQVYT LPPCRDELTKNQVSLWCLVKGF YPSDIAVEWESNGQPENNYKTT PPVLDSDGSFFLYSKLTVDKSR WQQGNVFSCSVMHEALHNHYTQ KSLSLSPGKSGGLNDIFEAQKI EWHE |

All 4-1BB-Fc-fusion molecule encoding sequences were cloned into a plasmid vector, which drives expression of the insert from an MPSV promoter and contains a synthetic polyA signal sequence located at the 3' end of the CDS. In addition, the vector contains an EBV OriP sequence for episomal maintenance of the plasmid.

For preparation of the biotinylated monomeric antigen/Fc fusion molecule, exponentially growing suspension HEK293 EBNA cells were co-transfected with three vectors encoding the two components of fusion protein (knob and hole chains) as well as BirA, an enzyme necessary for the biotinylation reaction. The corresponding vectors were used at a 2:1:0.05 ratio ("antigen ECD-AcTEV—Fc knob":"Fc hole":"BirA").

For protein production in 500 ml shake flasks, 400 million HEK293 EBNA cells were seeded 24 hours before transfection. For transfection cells were centrifuged for 5 minutes at 210 g, and the supernatant was replaced by pre-warmed CD CHO medium. Expression vectors were resuspended in 20 mL of CD CHO medium containing 200 μg of vector DNA. After addition of 540 μL of polyethylenimine (PEI), the solution was vortexed for 15 seconds and incubated for 10 minutes at room temperature. Afterwards, cells were mixed with the DNA/PEI solution, transferred to a 500 mL shake flask and incubated for 3 hours at 37° C. in an incubator with a 5% $CO_2$ atmosphere. After the incubation, 160 mL of F17 medium was added and cells were cultured for 24 hours. One day after transfection, 1 mM valproic acid and 7% Feed 1 with supplements were added to the culture. After 7 days of culturing, the cell supernatant was collected by spinning down cells for 15 min at 210 g. The solution was sterile filtered (0.22 μm filter), supplemented with sodium azide to a final concentration of 0.01% (w/v), and kept at 4° C.

Secreted proteins were purified from cell culture supernatants by affinity chromatography using Protein A, followed by size exclusion chromatography. For affinity chromatography, the supernatant was loaded on a HiTrap ProteinA HP column (CV=5 mL, GE Healthcare) equilibrated with 40 mL 20 mM sodium phosphate, 20 mM sodium citrate pH 7.5. Unbound protein was removed by washing with at least 10 column volumes of 20 mM sodium phosphate, 20 mM sodium citrate, 0.5 M sodium chloride containing buffer (pH 7.5). The bound protein was eluted using a linear pH-gradient of sodium chloride (from 0 to 500 mM) created over 20 column volumes of 20 mM sodium citrate, 0.01% (v/v) Tween-20, pH 3.0. The column was then washed with 10 column volumes of 20 mM sodium citrate, 500 mM sodium chloride, 0.01% (v/v) Tween-20, pH 3.0.

The pH of collected fractions was adjusted by adding 1/40 (v/v) of 2M Tris, pH8.0. The protein was concentrated and filtered prior to loading on a HiLoad Superdex 200 column (GE Healthcare) equilibrated with 2 mM MOPS, 150 mM sodium chloride, 0.02% (w/v) sodium azide solution of pH 7.4.

Human PD-L1-Fc (recombinant human PD-L1/B7-H1 Fc Chimera Protein, 156-B7-100: R&D Systems) is commercially available and was used for the determination of binding to PD-L1.

Determination of Simultaneous Binding

The capacity to bind simultaneously human 4-1BB Fc(kih) and human PD-L1 was assessed by surface plasmon resonance (SPR). All SPR experiments were performed on a Biacore T200 at 25° C. with HBS-EP as running buffer (0.01 M HEPES pH 7.4, 0.15 M NaCl, 3 mM EDTA, 0.005% Surfactant P20, Biacore, Freiburg/Germany). Human 4-1BB-Fc(kih) protein was directly coupled to a flow cell of a CM5 chip by amine coupling. Immobilization level of approx. 900 RU was used.

Figures 3A, 3B:
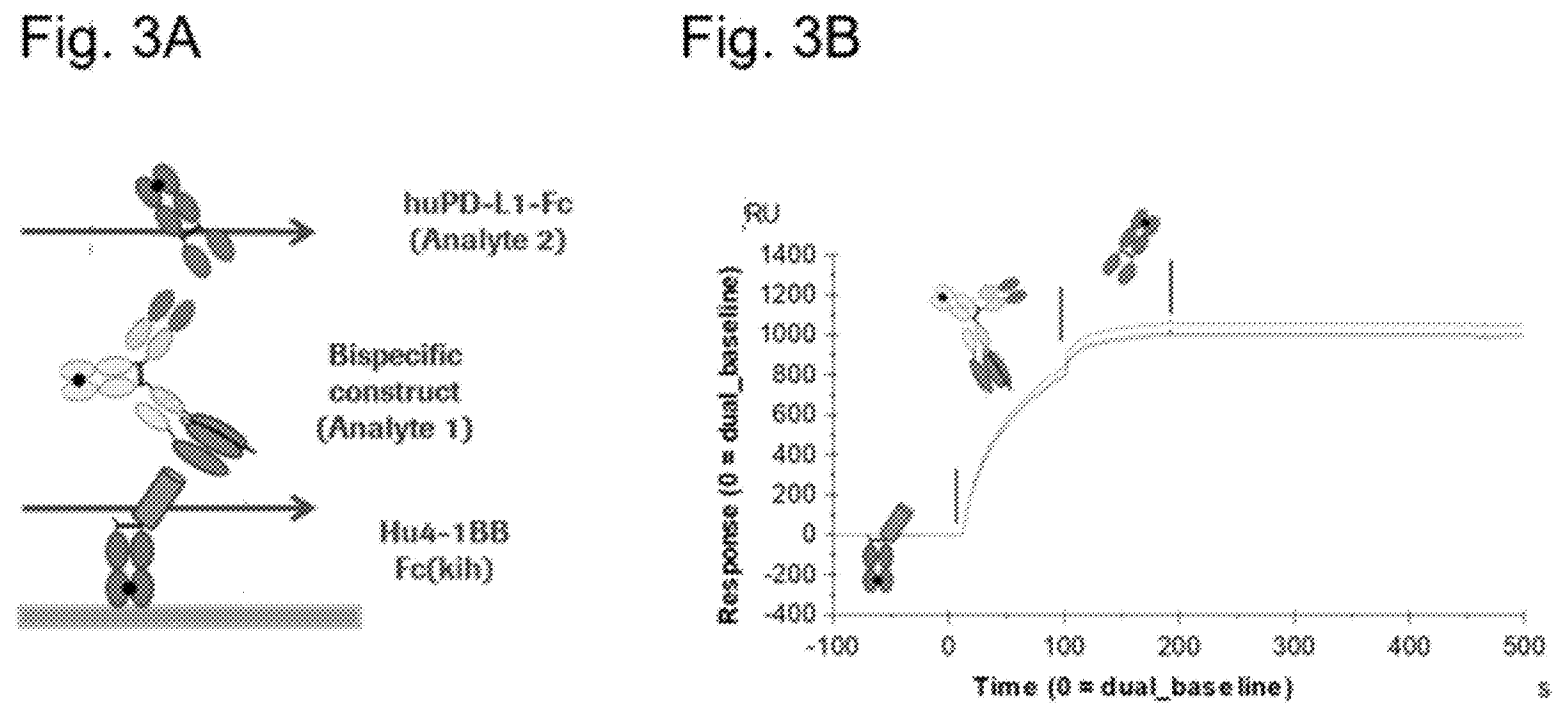

The PD-L1 targeting trimeric split 4-1BBL construct was passed at a concentration range of 150 nM with a flow of 10 μL/minute through the flow cells over 90 seconds and dissociation was set to zero sec. Human PD-L1-Fc (recombinant Human PD-L1/B7-H1 Fc Chimera Protein, 156-B7-100: R&D Systems) was injected as second analyte with a flow of 30 μL/minute through the flow cells over 90 seconds at a concentration of 200 nM (FIG. 3A). The dissociation was monitored for 240 sec. Bulk refractive index differences were corrected for by subtracting the response obtained in a reference flow cell, where no protein was immobilized.

As can be seen in FIG. 3B, the PD-L1 targeted-4-1BBL can bind simultaneously human PD-L1 and human 4-1BB.

Example 3

Functional Characterization of PD-L1 Targeting 4-1BB Ligand Trimer-Containing Antigen Binding Molecules by In Vitro Assay 3.1. Binding to Human PD-L1 Expressing Cell Lines First a cell line expressing human PD-L1 was generated. Full-length cDNAs encoding human PD-L1 were subcloned into mammalian expression vector. The plasmids were transfected into MKN45 (DSMZ 409) cells using Lipofectamine LTX Reagent (Invitrogen, #15338100) according to the manufacturer's protocol. Stably transfected PD-L1-positive PD-L1 cells were maintained in RPMI 1640 medium (GIBCO by Life Technologies, Cat No 42401-042) supplemented with 10% fetal bovine serum (FBS, GIBCO by Life Technologies, Cat.-No. 16000-044, Lot 941273, gamma irradiated mycoplasma free, heat inactivated) and 2 mM L-alanyl-L-glutamine dipeptide (Gluta-MAX-I, GIBCO by Life Technologies, Cat.-No. 35050-038) and under selection of 200 μg/mL Hygromycin B (Roche, Cat.-No. 10843555001) and 1.5 μg/mL Puromycin (Gibco by Life Technologies, Cat.-No. A11138-02). For the binding assay MKN45 cells and MKN45-huPD-L1 were harvested, washed with DPBS (GIBCO by life technologies, #14190-136) stained in DPBS containing fixable viability dye eF450

(eBioscience #65-0863-18) for 30 min at 4° C. Cells were washed and seeded to 384 well plates (Corning #3830) to $3\times10^4$ cells/well. Cells were centrifuged (350×g, 5 min), supernatant was removed and cells were resuspended in 10 μL/well FACS-buffer (DPBS supplied with 2% FBS, 5 nM EDTA, 7.5 mM sodium azide) containing titrated concentrations of PD-L1-4-1BBL or controls (start concentration 300 nM). Cells were incubated for 30 min at 4° C. and then washed twice with 80 μL/well DPBS. Cells were resuspended in 10 μL/well FACS-buffer containing 2.5 μg/mL PE-conjugated AffiniPure anti-human IgG Fcγ-fragment-specific goat $F(ab')_2$ fragment (Jackson ImmunoResearch, Cat.-No. 109-116-098) for 30 minutes at 4° C. Cells were washed twice with 80 μL/well DPBS and then fixed in 30 μL/well DPBS containing 1% formaldehyde for at least 15 minutes. The same or the next day cells were resuspended in 50 μL/well FACS-buffer and acquired using MACSQuant Analyzer X (Miltenyi Biotec).

Figures 4A, 4B:
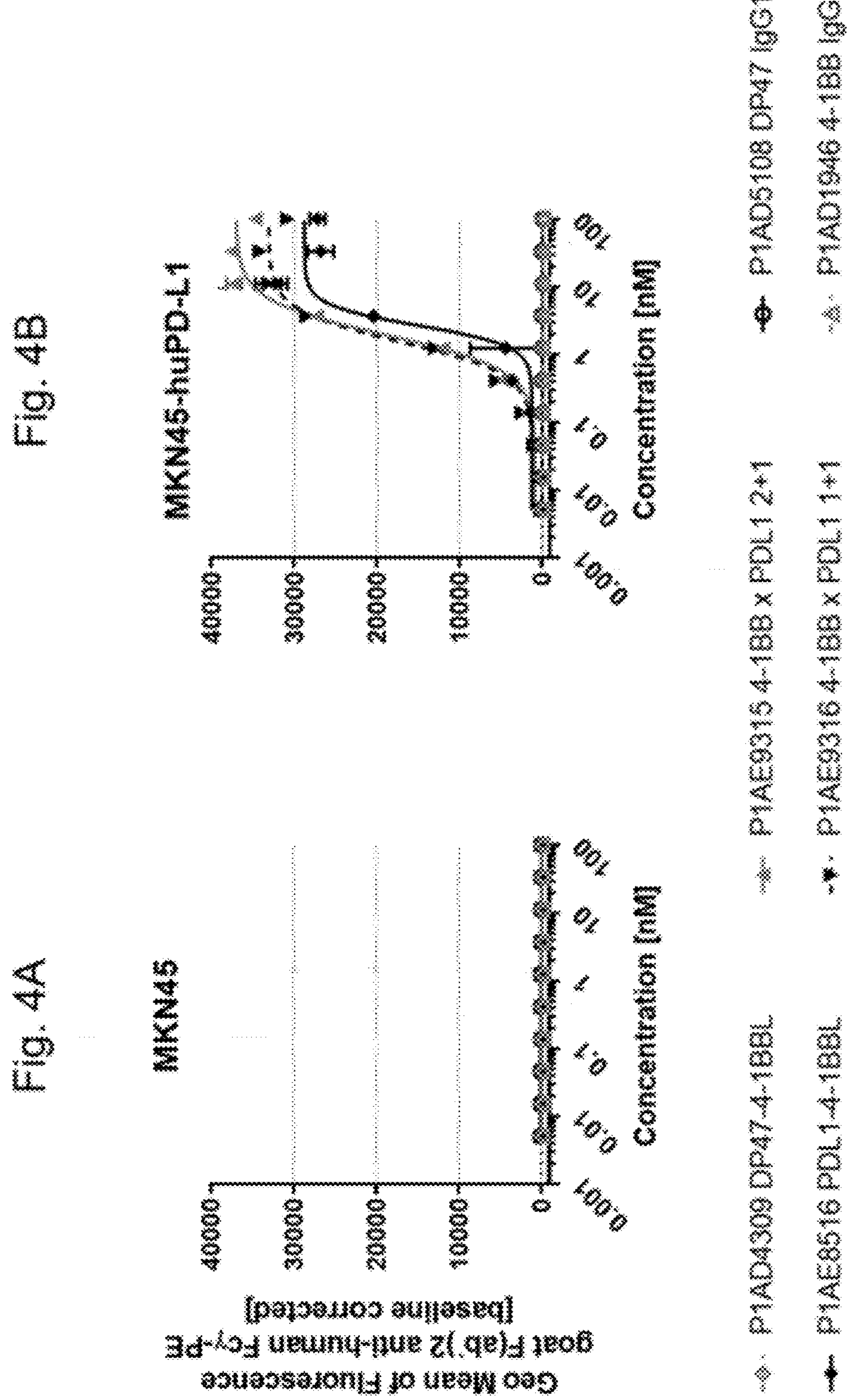
FIGS. 4A and 4B show the binding of PD-L1 targeting 4-1BB split trimeric ligand Fc fusion antigen binding molecules or the 4-1BB×PD-L1 bispecific antibodies to parental cell line MKN45 (FIG. 4A) or PD-L1-expressing cell line MKN45-PD-L1 (FIG. 4B) measured in two independent experiments. The concentration of PD-L1-4-1BBL or control molecules is blotted against the geo mean of fluorescence intensity of the PE-conjugated secondary detection antibody. All values are baseline corrected by subtracting the baseline values of the blank control (e.g. no primary only secondary detection antibody). Only PD-L1-4-1BBL or the 4-1BB-PDL1 bispecific antibodies bind efficiently to human PD-L1-expressing MKN45-huPD-L1 cells (FIG. 4B) but not to the parental cell line MKN45 (FIG. 4A).

As shown in FIGS. 4A and 4B, the PD-L1-4-1BBL construct (black triangle and line) but not the non-PD-L1-targeted controls bind efficiently to human PD-L1-expressing MKN45-huPD-L1 cells but not to the parental cell line MKN45. The fitting $EC_{50}$ values and the values of area under the curve are listed in Table 5.

Shown is the binding of PD-L1-4-1BBL to parental cell line MKN45 and PD-L1-expressing cell line MKN45-PD-L1. The concentration of PD-L1-4-1BBL or control molecules is blotted against the geo mean of fluorescence intensity of the PE-conjugated secondary detection antibody. All values are baseline corrected by subtracting the baseline values of the blank control (e.g. no primary only secondary detection antibody). PD-L1-4-1BBL binds efficiently to human PD-L1-expressing MKN45-huPD-L1 cells (FIG. 4B) but not to the parental cell line MKN45 (FIG. 4A). The bispecific 4-1BB×PDL1 antibodies showed even stronger binding to human PD-L1-expressing MKN45-huPD-L1 cells as PD-L1-4-1BBL.

TABLE 5

$EC_{50}$ values of binding curves to PD-L1 expressing cell line MKN45-PD-L1shown in FIG. 4B

| | $EC_{50}$ [nM] | AUC |
|---|---|---|
| PD-L1-4-1BBL | 2.68 | 49223 |
| DP47-4-1BBL | n.d. | 387 |
| DP47 huIgG1 P329G LALA | n.d. | 248 |
| 4-1BB × PDL1 2 + 1 | 1.95 | 66296 |
| 4-1BB × PDL1 1 + 1 | 1.54 | 63744 |
| 4-1BB huIgG1 P329G LALA | n.d. | 432 |

3.2 NF-κB Activation in Human 4-1BB and NFκB-Luciferase Reporter Gene Expressing Reporter Cell Line Jurkat-Hu4-1BB-NFκB-Luc2

Agonistic binding of the 4-1BB (CD137) receptor to its ligand (4-1BBL) induces 4-1BB-downstream signaling via activation of nuclear factor kappa B (NFkB) and promotes survival and activity of CD8 T cells (Lee H W, Park S J, Choi B K, Kim H H, Nam K O, Kwon B S. 4-1BB promotes the survival of CD8 (+) T lymphocytes by increasing expression of Bcl-x(L) and Bfl-1. J Immunol 2002; 169:4882-4888). To monitor this NFκB-activation mediated by 2+1 H2H anti-4-1BB×anti-PD-L1 huIgG1 PGLALA bispecific antibody, Jurkat-hu4-1BB-NFκB-luc2 reporter cell line was purchased from Promega (Germany). The cells were cultured as described above. For the assay, cells were harvested and resuspended in assay medium RPMI 1640 medium supplied with 10% (v/v) FBS and 1% (v/v) GlutaMAX-I. 10 μl containing $2\times10^3$ Jurkat-hu4-1BB-NFκB-luc2 reporter cells were transferred to each well of a sterile white 384-well flat bottom tissue culture plate with lid (Corning, Cat.-No.: 3826). 10 μL of assay medium containing titrated concentrations of PD-L1-4-1BBL antibody or control molecules were added. Finally, 10 μL of assay medium alone or containing $1\times10^4$ cells of parental MKN45 or MKN45 cells transfected with human PD-L1 were supplied and plates were incubated for 6 hours at 37° C. and 5% $CO_2$ in a cell incubator. 6 μl freshly thawed One-Glo Luciferase assay detection solution (Promega, Cat.-No.: E6110) were added to each well and Luminescence light emission were measured immediately using Tecan microplate reader (500 ms integration time, no filter collecting all wavelength).

As shown in FIGS. 5A to 5D, in the absence of PD-L1 expressing cells PD-L1-4-1BBL was not able to induce strong human 4-1BB receptor activation in the Jurkat-hu4-1BB-NFκB-luc2 reporter cell line, leading to NFκB-activation and therefore Luciferase expression expression in two independent experiments. In the presence of humanPD-L1-expressing MKN45 cells crosslinking of PD-L1-4-1BBL led to a strong increase of NFkB-activated Luciferase activity in the Jurkat-hu4-1BB-NFkB-luc2 reporter cell line, which was above the activation mediated by the untargeted control DP47-4-1BBL. Bispecific 4-1BB×PDL1 antibodies lead to similar but still slightly lower activities. Further, the anti-human 4-1BB clone 20H4.9 induced as huIgG1 P329G LALA some baseline activity displaying a superagonistic activity, which has been recently described for this clone (Sun K Ho et al. Mol Cancer Ther. 2020, 19(4), 1040-1051). $EC_{50}$ values and area under the curve (AUC) of activation curves are listed in Table 6.

TABLE 6

Figures 5A, 5B, 5C:
FIGS. 5A, 5B, 5C, 5D and 5E show the NFκB-mediated luciferase expression activity in 4-1BB expressing reporter cell line Jurkat-hu4-1BB-NFκB-luc2. To test the functionality of PD-L1-4-1BBL versus controls, molecules were incubated with the reporter cell line Jurkat-hu4-1BB-NFkB-luc2 in the absence or presence of MKN45 or human PD-L1 expressing MKN45 cell lines in a 1:5 ratio for 6 h. Afterwards cells were washed, lysed and incubated with Luciferin in a detection buffer. Luciferase-catalyzed oxidation of luciferin was detected via light emission as units of released light (y-axis). The concentration of PD-L1-4-1BBL molecule or its controls are blotted against the units of released light (RLU) measured after 6 h of incubation and addition of Luciferase detection solution. All values are baseline corrected by subtracting the baseline values of the blank control (e.g. no antibodies added).
Figures 5D, 5E:
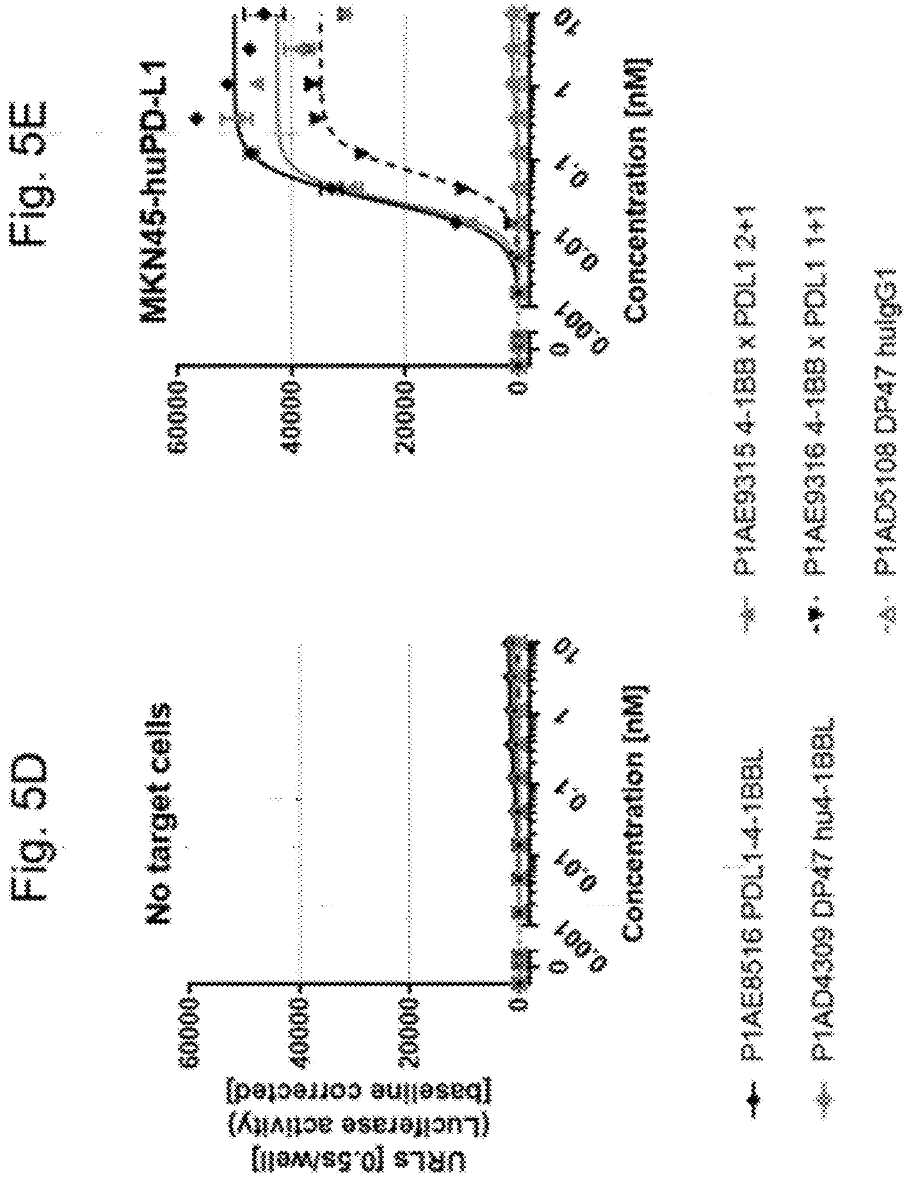

$EC_{50}$ values of NFκB-activation-induced Luciferase activity-curves shown in FIG. 5C

| | PD-L1-4-1BBL | DP47-4-1BBL | DP47 huIgG1 P329G LALA | 4-1BB × PDL1 2 + 1 | 4-1BB × PDL1 1 + 1 | 4-1BB huIgG1 P329G LALA |
|---|---|---|---|---|---|---|
| EC50 [nM] | 0.034 | n.d. | n.d. | 0.037 | 0.097 | 0.32 |
| AUC | 174842 | 1849 | 112 | 134607 | 122416 | 8874 |

The invention claimed is:

1. A 4-1BBL trimer-containing antigen binding molecule comprising (a) a first heavy chain comprising the amino acid sequence of SEQ ID NO:29, a first light chain comprising the amino acid sequence of SEQ ID NO:30, a second heavy chain comprising an amino acid sequence that is at least 95% identical to the amino acid sequence of SEQ ID NO:21 and a second light chain comprising an amino acid sequence that is at least 95% identical to the amino acid sequence of SEQ ID NO:22; wherein the second heavy chain comprises a heavy chain variable region (VH) comprising complementarity determining regions (CDR) comprising (i) CDR-H1 comprising the amino acid sequence of SEQ ID NO: 13, (ii) CDR-H2 comprising the amino acid sequence of SEQ ID NO: 14, and (iii) CDR-H3 comprising the amino acid sequence of SEQ ID NO: 15;

and the second light chain comprises a light chain variable region (VL) comprising (iv) CDR-L1 comprising the amino acid sequence of SEQ ID NO: 16, (v) CDR-L2 comprising the amino acid sequence of SEQ ID NO: 17, and (vi) CDR-L3 comprising the amino acid sequence of SEQ ID NO: 18;

or (b)

(i) a first heavy chain comprising the VH domain comprising the amino acid sequence of SEQ ID NO: 19 and a first light chain comprising the VL domain comprising the amino acid sequence of SEQ ID NO:20, (ii) a second heavy chain comprising the amino acid sequence selected from the group consisting of SEQ ID NO:21, SEQ ID NO:25 and SEQ ID NO:27, and (iii) a second light chain comprising the amino acid sequence selected from the group consisting of SEQ ID NO:22, SEQ ID NO:26 and SEQ ID NO:28.

2. The 4-1BBL trimer-containing antigen binding molecule of claim 1, wherein the first heavy chain or the second heavy chain comprise one or more amino acid substitution that reduces binding to an Fcγ receptor.

3. The 4-1BBL trimer-containing antigen binding molecule of claim 1, wherein the first heavy chain or the second heavy chain comprises the amino acid substitutions L234A, L235A and P329G (numbering according to Kabat EU index).

4. The 4-1BBL trimer-containing antigen binding molecule of claim 1, wherein the antigen binding molecule comprises (i) a first heavy chain comprising the VH domain comprising the amino acid sequence of SEQ ID NO:19 and a first light chain comprising the VL domain comprising the amino acid sequence of SEQ ID NO:20, (ii) a second heavy chain comprising the amino acid sequence selected from the group consisting of SEQ ID NO:21, SEQ ID NO:25 and SEQ ID NO:27, and (iii) a second light chain comprising the amino acid sequence selected from the group consisting of SEQ ID NO:22, SEQ ID NO:26 and SEQ ID NO:28.

5. The 4-1BBL trimer-containing antigen binding molecule of claim 1, wherein the antigen binding molecule comprises a first heavy chain comprising the amino acid sequence of SEQ ID NO:29, a first light chain comprising the amino acid sequence of SEQ ID NO:30, a second heavy chain comprising the amino acid sequence of SEQ ID NO: 21 and a second light chain comprising the amino acid sequence of SEQ ID NO:22.

6. The 4-1BBL trimer-containing antigen binding molecule of claim 1, wherein the antigen binding molecule comprises (i) a first heavy chain comprising the VH domain comprising the amino acid sequence of SEQ ID NO:19 and a first light chain comprising the VL domain comprising the amino acid sequence of SEQ ID NO:20, (ii) a second heavy chain comprising the amino acid sequence selected of SEQ ID NO:21, and (iii) a second light chain comprising the amino acid sequence of SEQ ID NO:22, SEQ ID NO: 26 and SEQ ID NO:28.

7. The 4-1BBL trimer-containing antigen binding molecule of claim 1, wherein the antigen binding molecule comprises (i) a first heavy chain comprising the VH domain comprising the amino acid sequence of SEQ ID NO:19 and a first light chain comprising the VL domain comprising the amino acid sequence of SEQ ID NO:20, (ii) a second heavy chain comprising the amino acid sequence of SEQ ID NO:25, and (iii) a second light chain comprising the amino acid sequence of SEQ ID NO:26.

8. The 4-1BBL trimer-containing antigen binding molecule of claim 1, wherein the antigen binding molecule comprises (i) a first heavy chain comprising the VH domain comprising the amino acid sequence of SEQ ID NO:19 and a first light chain comprising the VL domain comprising the amino acid sequence of SEQ ID NO:20, (ii) a second heavy chain comprising the amino acid sequence of SEQ ID NO:27, and (iii) a second light chain comprising the amino acid sequence of SEQ ID NO:28.

9. An isolated nucleic acid molecule encoding the 4-1BBL trimer-containing antigen binding molecule of claim 1.

10. A vector comprising the isolated nucleic acid molecule of claim 9.

11. The vector of claim 10, wherein said vector is an expression vector.

12. A host cell comprising the nucleic acid of claim 9.

13. A pharmaceutical composition comprising the 4-1BBL trimer-containing antigen binding molecule of claim 1 and at least one pharmaceutically acceptable excipient.

14. The pharmaceutical composition of claim 13, further comprising an additional therapeutic agent.

15. A method of producing a 4-1BBL trimer-containing antigen binding molecule, comprising culturing the host cell of claim 12 under conditions suitable for expression of the 4-1BBL trimer-containing antigen binding molecule.

16. The method of claim 15, further comprising recovering the 4-1BBL trimer-containing antigen binding molecule from the host cell.

17. A 4-1BBL trimer-containing antigen binding molecule produced by the method of claim 15.

* * * * *